United States Patent [19]

Katsube et al.

[11] 4,347,254
[45] Aug. 31, 1982

[54] TRICYCLIC CAGE COMPOUNDS, THEIR SYNTHESIS AND USE AS ANTIVIRAL AGENTS

[75] Inventors: Junki Katsube, Osaka; Hiromi Shimomura, Hyogo; Shun Inokuma, Osaka; Akihiko Sugie, Hyogo, all of Japan

[73] Assignee: Sumitomo Chemical Company, Limited, Osaka, Japan

[21] Appl. No.: 171,109

[22] Filed: Jul. 22, 1980

Related U.S. Application Data

[63] Continuation-in-part of Ser. No. 29,694, Apr. 13, 1979, abandoned.

[30] Foreign Application Priority Data

Apr. 14, 1978 [JP] Japan .................................. 53-44386
Oct. 20, 1978 [JP] Japan ................................ 53-129812
Mar. 7, 1979 [JP] Japan .................................. 54-27170

[51] Int. Cl.$^3$ ...................... A61K 31/38; A61K 31/34; A61K 31/35; C07D 307/92
[52] U.S. Cl. .................................. 424/275; 549/43; 549/46; 549/26; 549/27; 549/12; 424/285; 424/283; 549/263; 549/281; 549/349; 549/386; 549/459
[58] Field of Search ................ 260/346.71, 345.2, 333, 260/345.1, 345.7 R, 345.8 R; 549/43, 46, 26, 27, 12; 424/275, 285, 283

[56] References Cited

U.S. PATENT DOCUMENTS

3,346,596 10/1967 Hoch et al. .................... 260/346.71
3,401,179 9/1968 Wiese et al. .................... 260/346.71

FOREIGN PATENT DOCUMENTS

1474107 7/1966 France ........................... 260/346.71
1498493 8/1966 France ........................... 260/346.71
2305495 3/1976 France ........................... 260/346.71
1446632 9/1973 United Kingdom ........... 260/346.71
1526351 3/1976 United Kingdom ........... 260/346.71

OTHER PUBLICATIONS

Tetrahedron Letters, No. 19, pp. 1165-1170, 1964, Moriarty, et al.
Crundwell, et al., Tetrahedron, vol. 34, pp. 1043-1045, 1978.
J. Org. Chem., vol. 41, No. 7, 1976, pp. 1229-1233.
Tetrahedron Letters, No. 46, pp. 4003-4006, 1970.
J. of Org. Chem., vol. 38, No. 10, 1973, pp. 1803-1806.
J.A.C.S., vol. 89, Jul. 19, 1967, pp. 3927-3929.

Primary Examiner—Henry R. Jiles
Assistant Examiner—Robert C. Whittenbaugh
Attorney, Agent, or Firm—Birch, Stewart, Kolasch & Birch

[57] ABSTRACT

A compound of the formula:

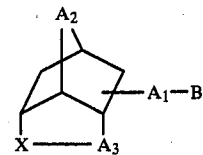

wherein $A_1$ is a single bond or a $C_1$-$C_5$ alkylene group bonding at the 2-, 2'- or 3-position, $A_2$ is a $C_1$-$C_3$ alkylene group, $A_3$ is a $C_1$-$C_4$ alkylene group, X is —O— or —SO$_n$— and B is a carboxy group, a $C_2$-$C_5$ alkoxycarbonyl group, a cyano group, an amino group of the formula:

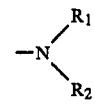

or a carbamoyl group of the formula:

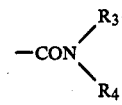

which is useful as an antiviral agent with no side effect.

20 Claims, No Drawings

TRICYCLIC CAGE COMPOUNDS, THEIR SYNTHESIS AND USE AS ANTIVIRAL AGENTS

This is a continuation-in-part application of our co-pending application Ser. No. 29,694 filed on Apr. 13, 1979, now abandoned.

The present invention relates to tricyclic cage compounds and their production and use. More particularly, this invention relates to novel heterotricyclic cage compounds, a pharmaceutical composition containing at least one of them and a process for preparing them.

The novel heterotricyclic cage compounds of this invention are those represented by the following formula (I):

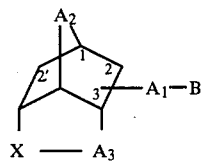
(I)

wherein $A_1$ is a single bond or a $C_1$–$C_5$ alkylene group bonding at the 2-, 2'-, or 3-position, $A_2$ is a $C_1$–$C_3$ alkylene group, $A_3$ is a $C_1$–$C_4$ alkylene group, X is —O— or —SO$_n$— (wherein n is an integer of 0 to 2) and B is a carboxy group, a $C_2$–$C_5$ alkoxycarbonyl group, a cyano group, an amino group of the formula:

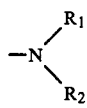

(wherein $R_1$ is a hydrogen atom, a $C_1$–$C_5$ alkyl group, a $C_3$–$C_5$ alkenyl group, a $C_3$–$C_5$ alkynyl group or a $C_7$–$C_9$ aralkyl group and $R_2$ is a hydrogen atom, a $C_1$–$C_5$ alkyl group, a $C_3$–$C_5$ alkenyl group, a $C_3$–$C_5$ alkynyl group, a $C_7$–$C_9$ aralkyl group, a $C_2$–$C_5$ alkoxycarbonyl group, a benzyloxycarbonyl group, a $C_2$–$C_5$ alkanoyl group or a $C_2$–$C_4$ haloalkanoyl group, or when taken together with the adjacent nitrogen atom, $R_1$ and $R_2$ may form a pyrrolidino group, a piperazino group or a morpholino group), a carbamoyl group of the formula:

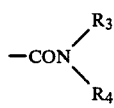

(wherein $R_3$ and $R_4$ are each a hydrogen atom, a $C_1$–$C_5$ alkyl group or a $C_3$–$C_5$ alkenyl group, or when taken together with the adjacent nitrogen atom, $R_3$ and $R_4$ may form a pyrrolidino group, a piperazino group or a morpholino group), and their non-toxic salts.

In the significances as used above, "$C_1$–$C_5$ alkylene" for $A_1$ means an alkylene group having 1 to 5 carbon atoms, (e.g. methylene, ethylene, ethylidene, trimethylene); "$C_1$–$C_3$ alkylene" for $A_2$ means an alkylene group having 1 to 3 carbon atoms (e.g. methylene, ethylene, trimethylene, cyclopropylene, ethylidene, propylidene); "$C_1$–$C_4$ alkylene" for $A_3$ means an alkylene group having 1 to 4 carbon atoms (e.g. methylene, ethylene, ethylidene, trimethylene); and "$C_2$–$C_5$ alkoxycarbonyl" for B means an alkoxycarbonyl group having 2 to 5 carbon atoms (e.g. methoxycarbonyl, ethoxycarbonyl, t-butoxycarbonyl). Further, "$C_1$–$C_5$ alkyl" for $R_1$, $R_2$, $R_3$ and $R_4$ includes methyl, ethyl, n-propyl, isobutyl, etc.; "$C_3$–$C_5$ alkenyl" for $R_1$, $R_2$, $R_3$ and $R_4$ are allyl, crotyl, 3,3-dimethylallyl, etc.; "$C_3$–$C_5$ alkyl" for $R_1$ and $R_2$ means propargyl, 2-butynyl, etc.; "$C_7$–$C_9$ aralkyl" for $R_1$ and $R_2$ includes benzyl, phenethyl, etc.; "$C_2$–$C_5$ alkoxycarbonyl" for $R_2$ are methoxycarbonyl, ethoxycarbonyl, t-butoxycarbonyl, etc.; "$C_2$–$C_5$ alkanoyl" for $R_2$ are acetyl, propanoyl, butanoyl, etc.; and "$C_2$–$C_4$ haloalkanoyl" for $R_2$ are chloroacetyl, bromoacetyl, trifluoroacetyl, etc.

Among the heterocyclic cage compounds (I) of this invention, those of the following formula (Ia) are preferable:

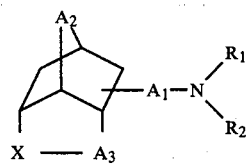
(Ia)

wherein $A_1$, $A_2$, $A_3$, X, $R_1$ and $R_2$ are each as defined above.

Particularly preferred are those of the following formula (Ib):

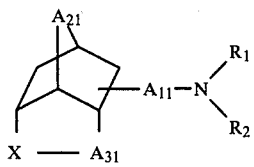
(Ib)

wherein $R_1$, $R_2$ and X are each as defined above, $A_{11}$ is a single bond or a methylene group bonding at the 2-, 2'-, or 3-position, $A_{21}$ is a methylene group or an ethylene group and $A_{31}$ is a methylene group or an ethylene group.

More particularly preferred are those of the following formula (Ic):

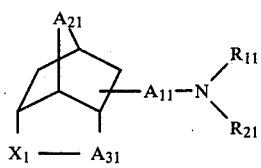
(Ic)

wherein $A_{11}$, $A_{21}$ and $A_{31}$ are each as defined above, $R_{11}$ is a hydrogen atom, an $C_1$–$C_5$ alkyl group, a $C_3$–$C_5$ alkenyl group, a $C_3$–$C_5$ alkynyl group or a $C_7$–$C_9$ aralkyl group, $R_{21}$ is a hydrogen atom, a $C_1$–$C_5$ alkyl group or a $C_2$–$C_5$ alkoxycarbonyl group and $X_1$ is —O— or —S—.

The compounds of the following formula (Id):

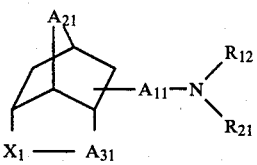
(Id)

wherein $A_{11}$, $A_{21}$, $A_{31}$, $R_{21}$ and $X_1$ are each as defined above and $R_{12}$ is a hydrogen atom or a $C_1$–$C_5$ alkyl group are more preferable.

More preferred are those of the following formula (Ie):

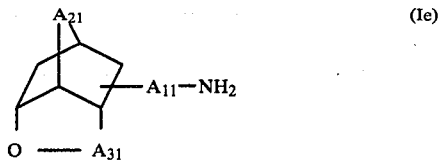
(Ie)

wherein $A_{11}$, $A_{21}$ and $A_{31}$ are as defined above.

When B is a carboxy group or a $C_2$–$C_5$ alkoxycarbonyl group in the formula (I), the compounds of the following formula (If):

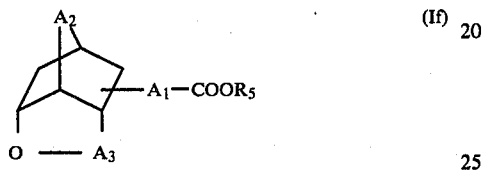
(If)

wherein $A_1$, $A_2$ and $A_3$ are each as defined above and $R_5$ is a hydrogen atom or a $C_1$–$C_4$ alkyl group, are preferable.

Particularly preferred are the compounds of the following formula (Ig):

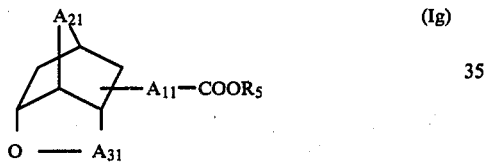
(Ig)

wherein $A_{11}$, $A_{21}$, $A_{31}$ and $R_5$ are each as defined above.

The most preferred are the compounds of the following formula (Ih):

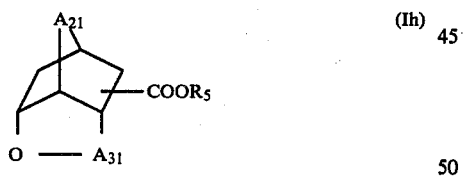
(Ih)

wherein $A_{21}$, $A_{31}$ and $R_5$ are each as defined above, the substituent ($-COOR_5$) bonding at the 2-, 2'- or 3-position.

The structure of the novel heterocyclic cage compounds of this invention is characterized firstly by their tricyclic cage skeleton having a hetero atom linkage represented by the general formula (I'):

(I')

wherein $A_2$, $A_3$ and X are each as defined above, and secondly by their amino or carboxyl group or its related substituent thereof represented by the general formula: $-A_1-B$ (wherein $A_1$ and B are each as defined above) bonding at the 2-, 2'- or 3-position.

Concerning the heterotricyclic cage compounds having the said skeleton (I'), only a few compounds have hitherto been described, and a small amount of study on their chemistry or synthesis has hitherto been done. That is, the following compounds were synthesized previously:

(A) French Pat. No. A-1474107 (1966) discloses the formation of the compounds of the following formulae:

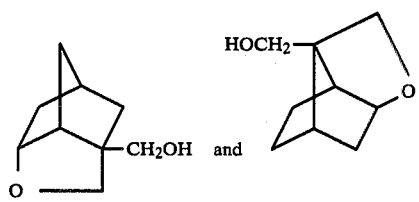

by acid catalized isomerization of 2,2-bishydroxymethyl-5-norbornene and their use as intermediates for plasticizers or lubricant stabilizers.

French Pat. No. A-1498493 (1966) also discloses the acylates of the said compound of the formula:

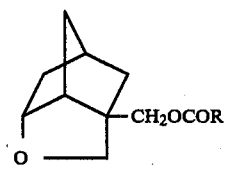

as intermediates for plasticizers or lubricant stabilizers.

(B) M. Nakazaki, K. Naemura and Y. Kondo., J. Org. Chem., 41, p. 1229 (1979) report the preparation of the compound of the formula:

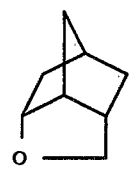

(C) R. M. Moriarty and K. Kapadia., Tetrahedron Letters, p. 1165 (1964) report the preparation of the compounds of the formulae:

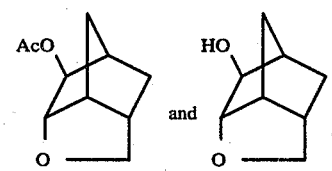

(D) R. M. Moriarty, H. Gopal and T. Adams., Tetrahedron Letters, p. 4003 (1970) report the preparation of the compounds of the formulae:

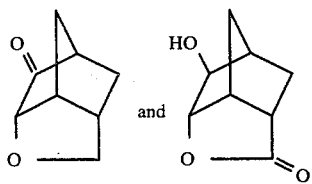

(E) R. M. Moriarty, C. R. Romain and T. O. Lovett., J. Am. Chem. Soc., 89, p. 3927 (1967) report the preparation of the compounds of the formulae:

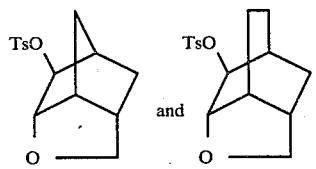

(F) C. R. Johnson and W. D. Kingsbury., J. Org. Chem., 38, p. 1803 (1973) report the preparation of the compounds of the formulae:

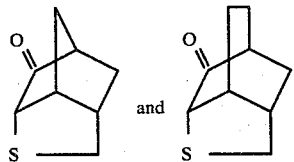

Under the situation as described above, the present inventors have studied and developed the synthesis of the said heterotricyclic cage compounds and also made search on their useful biological activities. As the result, it has now been found that the novel heterotricyclic cage compounds (I) of the invention exhibit excellent antiviral activity.

As reviewed by L. Weinstein in "Pharmacological Basis of Therapeutics" (L. S. Goodman & A. Gilman, McMillan Company) p. 1305-1307 (1970), very few agents have been found to have clinical applicability for antiviral drug although the search for substances that might be of use in the management of viral infections has been long and intensive. Idoxuridine, amantadine and methiazone, synthetic antivirals for clinical use, are described in said text.

The heterotircyclic cage compound (I) of the invention may be employed to control, namely to treat and prevent viral infections caused by RNA type viruses such as Myxo group.

As a clinically useful anti-influenza A viral agent with a cage structure, amantadine of the following formula is already known (Merck Index 9th, p. 367-368).

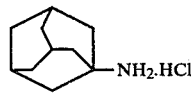

The amantadine is now marketed in U.S.A. as an anti-influenza A viral agent. However, it possesses not only an antiviral activity but also strong effects on a central nervous system (CNS). Based on such CNS-effects, amantadine is now marketed as an anti-parkinsonism agent in several countries including Japan, West Germany, United Kingdom or France. For antiviral agents, the CNS-effects of amantadine is deemed as undesirable side effects.

The heterotricyclic cage compounds (I) of the present invention are found to be very effective to inhibit the growth of influenza virus, but surprisingly, exerting no or almost no CNS-effects. In addition, the toxicities of the heterotricyclic cage compound (I) are found to be significantly lower than those of amantadine. Thus, the heterotricyclic cage compounds (I) are very useful as antiviral agents with no or weak side effects or toxicities.

Some of the heterotricyclic cage compounds (I) of the invention are also useful as intermediates for another type of the heterotricyclic cage compounds (I).

The heterotricyclic cage compounds (I) and their non-toxic salts can be used for treatment of the viral infection of mammals caused by influenza virus or for prevention thereof. For this purpose, they can be administered either alone or in combination with pharmaceutically acceptable carriers. The proportion of the agent administered is determined by the solubility and chemical nature of the compound, chosen route of administration and standard biological practice. For example, they may be administered orally in solid forms, such as starch, mild sugar and so forth. They may be also administered orally in the form of solutions or injected parenterally. For parenteral administration, they may be used in the form of sterile solutions containing other solutes, for example, enough saline or glucose to make the solutions isotonic.

For example, these compounds (I) can inhibit the influenza virus multiplication in tissue culture method. Furthermore, they are very low cytotoxic.

For instance, Compound No. 27-2 cited in Table IV has values of 25 µg/ml in the minimum effective concentration (MEC) and of 200 µg/ml in the minimum cytotoxic concentration (MCC). Therefore, a chemotherapeutic index (MCC/MEC) of Compound No. 27-2 is 8. As MEC of amantadine, commercially available as an antiviral drug for small Myxo virus (classified as the same Myxo virus groups as influenza virus) infections, is 12.5 and its MCC is 12.5, its chemotherapeutic index is 1. Compared with these values, Compound No. 27-2 is proved to be 8 times as safe as amantadine.

Antiviral effects of these compounds (I) are also confirmed by in vivo experiments. When mice are infected by inhalation of influenza virus, the grade of virus-induced lung consolidation is observed, and the antiviral effects of the compounds (I) are determined by the supressing effects on the said lung consolidation.

As indicated in Table III, for example, the efficacy of Compound No. 29-1 or 12-3 is comparable to that of amantadine. Low toxicities of the compounds (I) of the invention are also demonstrated in Table I. That is, the acute toxicities of the compounds (I) of the invention are much weaker than that of amantadine as shown in Table I.

Moreover, it is shown in Table II that the compounds (I) of the invention do not have any strong antagonizing effect on the haloperidol induced catalepsy. That is, for example, most of the compounds (I) of the invention have no or very weak effect on the catalepsy at doses up to 500 mg/kg, whereas amantadine itself antagonizes the catalepsy at 50 mg/kg. This means that the compounds (I) of the invention do not have any strong effect on CNS-system: high correlation between the anti-catalepsy effect and CNS-stimulating effect is already revealed; see "P. Siwou et al., J. Pharm. Pharmcol., 22, 546–547 (1970)" or "J. May et al., Psychopharmcol., 24, 296–307 (1972)".

In addition, no side effects were observed in mice treated by these compounds (I).

Therefore, the compounds (I) of the invention are superior to amantadine as an antiviral agent. Thus, the compounds of the invention are epochmaking antiviral agents in terms of their remarkable effectiveness and very low toxicity.

The compounds (I) of the invention may be used in the form of pharmaceutical preparations appropriate for enteral or parenteral administration. Preferable excipients used therein are those which do not react with the compounds mentioned above, for example, water, gelatine, lactose, starch, stearic acid, magnesium stearate, talc, white petroleum jelly, vegitable oils, alcohol, benzyl alcohol, gums, polyalkylene glycols, or other known excipients for medicines. The pharmaceutical preparations may be in the form of tablets, powder, dragees (sugar coated tablets), capsules, suppositories, liquids, elixirs, emulsions, suspensions, syrups, chocolate, candy, waters, chewing gum or the like. If desired, they are sterilized and/or contain auxiliary substances such as preservatives, stabilizers, wetting agents, detergents or buffers. They may also additionally contain other therapeutically valuable substances (e.g. other antiviral agents, chemotherapuetic agents, antibiotics, anti-inflammatory agents, anti-pyretics, analgesics, enzyme preparations or the like).

The pharmaceutical preparations are formulated by usual methods. They may be conjointly administered with a viral inhibitor such as interferon, interferon inducer or the like. The compositions and preparations should contain at least 0.1% of active component.

The compositions of this invention may be administered enterally, parenterally or in the form of nasal and oral aerosol spray. The compositions of this invention are also effective in resisting as well as combatting viral infections when administered topically to the site of the infection or potential infection in the form of ointments, salves, lotions, creams, sprays, drops, etc. The amount of the active component in such useful compositions or preparations is such that a suitable dosage of 0.5 mg to 50 mg/Kg/day will be obtained.

These compounds may be used systemically, more concretely, parenterally and non-parenterally, etc. and by a local application such as inhalation, topical application and dropping in the eye, etc., in the preparation form suitable for application such as liquid, ointment, powder, granule, mush, pellet, capsule, tablet, etc. by the addition of afore-mentioned solvent, additives, carriers, etc.

The heterotricyclic cage compounds (I) of this invention can be prepared by the following methods:

Method A

The compound of the formula (Ii):

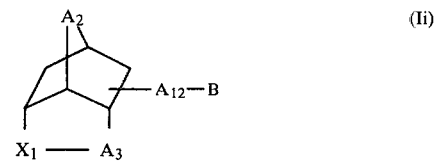

wherein $A_2$, $A_3$ and B are each as defined above, $A_{12}$ is a single bond or a $C_1$–$C_5$ alkylene group bonding at the 2- or 3-position and $X_1$ is —O— or —S—, can be prepared by cyclizing the compound of the formula (IIa):

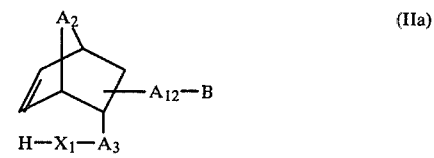

wherein $A_{12}$, $A_2$, $A_3$, B and $X_1$ are each as defined above.

The reaction may generally be carried out in an inert solvent (e.g. tetrahydrofuran, benzene, dioxane, water, dimethylformamide) at a temperature ranging from $-20°$ C. to the boiling point of the solvent used in the presence of a suitable catalyst.

When the compounds of the formula (Ii) wherein $X_1$ is —O— are to be prepared, the reaction may preferably be conducted in the presence of an acid catalyst such as sulfuric acid, alumina, silica-alumina or zeolite at a temperature from room temperature (about 20° C.) to the boiling point of the solvent used. On the other hand, when the compounds of the formula (Ii) wherein X is —S— are to be prepared, the reaction may preferably be carried out in the presence of such catalysts as tertiary amines or caustic alkalis.

The heterotricyclic cage compound thus obtained can be separated from the reaction mixture and purified by conventional procedures.

Method B

The compound of the formula (Ii):

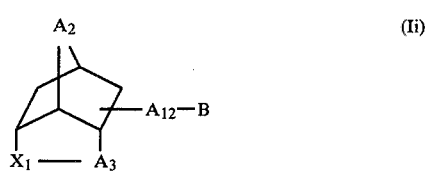

wherein $A_{12}$, $A_2$, $A_3$, B and $X_1$ are each as defined above, can be prepared by reducing the compound of the formula (IIb):

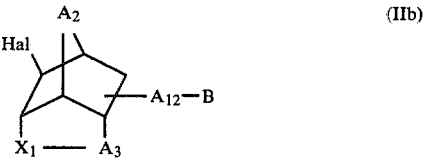

wherein $A_{12}$, $A_2$, $A_3$, B and $X_1$ are each as defined above and Hal is a halogen atom, in an inert solvent.

The reducing reaction may be carried out by treating the compound of the formula (IIb) with a suitable reducing agent in an inert solvent at a temperature ranging from $-78°$ C. to the boiling point of the solvent used, preferably from room temperature to the boiling point of the solvent used. Examples of such reducing agent are metal hydride compounds such as lithium aluminum hydride, sodium trialkoxyaluminum hydride, sodium diethylaluminum hydride, sodium bis(methoxyethoxy)aluminum hydride, sodium borocyanohydride, tributyltin hydride, dibutyltin hydride and triphenyltin hydride. As the solvent, there may be exemplified ether, tetrahydrofuran, dimethoxyethane, methanol, ethanol, benzene, toluene, etc.

When the compound of the formula (IIb) having a functional group susceptible to reduction (e.g. carboxy, $C_2$–$C_5$ alkoxycarbonyl, cyano, amino, carbamoyl) is to be used as the starting material, the reducing reaction may preferably be conducted by using an alkyltin hydride with a suitable radical initiator such as azobisisobutyronitrile. The reaction may also be achieved by hydrogenation in the presence of a suitable catalyst such as palladium charcoal (Pd-C), platinum oxide ($PtO_2$) or Raney-Ni. The hydrogenation is generally carried out in an inert solvent, preferably at a temperature of from room temperature to the boiling point of the solvent used. As the solvent, those as exemplified above may also be used.

The heterotricyclic cage compound thus obtained can be separated from the reaction mixture and purified by the conventional procedures.

Method C

The compound of the formula (Ij):

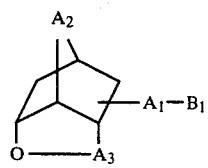

(Ij)

wherein $A_1$, $A_2$ and $A_3$ are each as defined above and $B_1$ is a cyano group, a carbamoyl group of the formula:

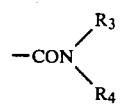

wherein $R_3$ and $R_4$ are each as defined above, or an amino group of the formula:

wherein $R_{11}$ is as defined above and $R_{22}$ is a $C_2$–$C_5$ alkoxycarbonyl group, a benzyloxycarbonyl group, a $C_2$–$C_5$ alkanoyl group or a $C_2$–$C_4$ haloalkanoyl group, can be prepared by reacting the compound of the formula (IIc):

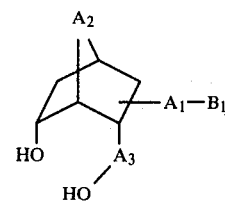

(IIc)

wherein $A_1$, $A_2$, $A_3$ and $B_1$ are each as defined above, with a dehydrating agent.

As the dehydrating agent, a hydroxy-activating reagent such as p-toluenesulfonyl chloride, mesyl chloride, thionyl chloride or phosphorus oxychloride may be used. The reaction may be carried out in the presence of an inert solvent (e.g. ether, benzene, toluene, pyridine, triethylamine). The reaction temperature may vary from $-20°$ C. to the boiling point of the solvent used.

The heterotricyclic cage compound thus obtained can be separated from the reaction mixture and purified by the conventional procedures.

Method D

The compound of the formula (Ik):

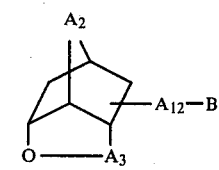

(Ik)

wherein $A_{12}$, $A_2$, $A_3$ and B are each as defined above, can be prepared by cyclizing the compound of the formula (IId):

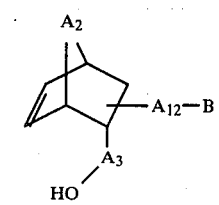

(IId)

wherein $A_{12}$, $A_2$, $A_3$ and B are each as defined above, according to the oxymercuration-demercuration reaction.

The oxymercuration-demercuration reaction may be carried out by treating the compound of the formula (IId) with a mercuric salt (e.g. $Hg(OCOCH_3)_2$, $Hg(OCOCCl_3)_2$, $Hg(OCOCF_3)_2$, $Hg(NO_3)_2$) and reducing the resulting product (oxymercuration adduct) with a reducing agent such as sodium borohydride. The reaction may be carried out in the presence of an inert solvent (e.g. water, tetrahydrofuran, dioxane, dimethylformamide). The reaction temperature may be from 0° C. to the boiling point of the solvent used.

The heterotricyclic cage compound thus obtained can be separated from the reaction mixture and purified by the conventional procedures.

Method E

The compound of the formula (Il):

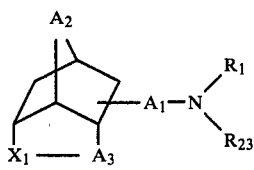

wherein $A_1$, $A_2$, $A_3$, $R_1$ and $X_1$ are each as defined above and $R_{23}$ is a hydrogen atom, a $C_1$-$C_5$ alkyl group, a $C_3$-$C_5$ alkenyl group, a $C_3$-$C_5$ alkynyl group or a $C_7$-$C_9$ aralkyl group, or when $R_1$ and $R_{23}$ are taken together with the adjacent nitrogen atom, they may form a pyrrolidino group, a piperazino group or a morpholino group, can be prepared from the corresponding tricyclic cage compound having a suitable substituent by the following methods thereby converting the substituent into an amino group represented by

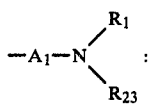

(Ea) via Reduction

(1)

(wherein $A_{13}$ is a single bond or a $C_1$—$C_4$ alkylene group bonding at the 2-, 2'- or 3-position)

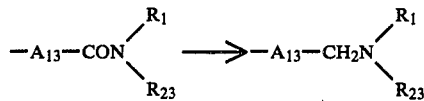

(2)

(wherein $A_{13}$, $R_1$ and $R_{23}$ are each as defined above)

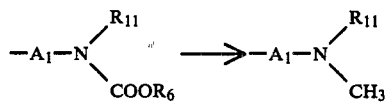

(3)

(wherein $R_6$ is a $C_1$—$C_4$ alkyl group, and $A_1$ and $R_{11}$ are each as defined above)

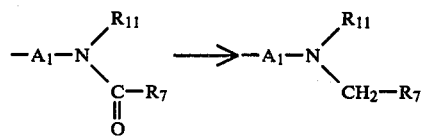

(4)

(wherein $R_7$ is a hydrogen atom, a $C_1$—$C_4$ alkyl group or a $C_2$—$C_4$ alkenyl group)

(5)

wherein $R_5$ and $A_{13}$ are each as defined above)

(6)

(wherein $A_1$ is as defined above)

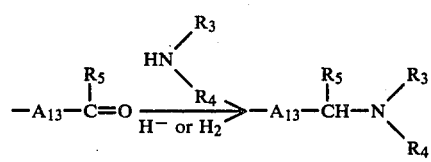

(7)

-continued
(wherein $A_{13}$, $R_3$, $R_4$ and $R_5$ are each as defined above)

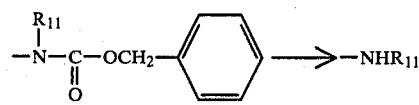

(8)

(wherein $R_{11}$ is as defined above).

The reduction (1), (2), (3), (4), (5) or (6) may preferably be carried out by treatment with a metal hydride compound such as lithium aluminum hydride, sodium trialkoxyaluminum hydride, sodium diethylaluminum hydride or sodium bis(methoxyethoxy)aluminum hydride in an inert solvent such as ether, tetrahydrofuran or toluene.

The reaction (7) is known as the reductive amination and it may be effected by reacting the carbonyl compound with ammonia or an amine in the presence of a reducing agent such as a metal borohydride, an active metal and an acid or formic acid or its derivative in a solvent such as methanol, ethanol, benzene toluene and the like.

The reduction (1), (5), (6) or (8) may be also effected by hydrogenation in the presence of a catalyst such as palladium charcoal, platinum oxide or Raney-Ni in an inert solvent such as methanol, ethanol, benzene or toluene. The temperature for the above reduction may vary depending on the type of reduction or reducing agent to be used therein, but these reactions (1) to (8) may generally be carried out at a temperature of from $-20°$ C. to the boiling point of the solvent to be used therein.

(Eb) via Substitution

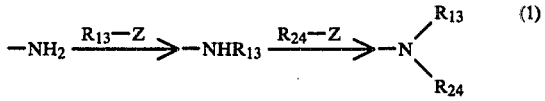

(1)

wherein Z is the residue of a strong acid, $R_{13}$ is the same as $R_1$ excluding a hydrogen atom and $R_{24}$ is the same as $R_2$ excluding a hydrogen atom)

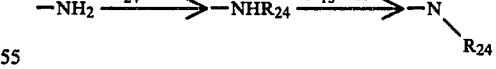

(2)

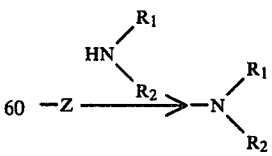

(3)

The reaction (1) or (2) may be effected by reacting the amine compound (—$NH_2$, —$NHR_{13}$ or —$NHR_{24}$) with the activated radical such as $R_{13}$-Z or $R_{24}$-Z. The reaction (3) may also be achieved by reacting the compound of the formula (Im):

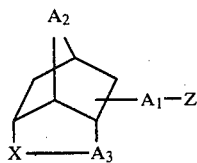 (Im)

wherein $A_1$, $A_2$, $A_3$, X and Z are each as defined above, with the amine

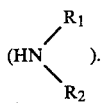

Examples of the residue of a strong acid represented by Z are chloride (—Cl), bromide (—Br), p-toluenesulfonate

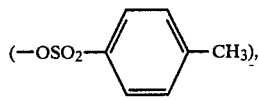

methanesulfonate (—$OSO_2$—$CH_3$), sulfate (—O—$SO_2$—O—) and so on. The reaction (1), (2) or (3) may preferably be carried out by using an organic or inorganic base.

A variety of bases can be used in these reactions (1) to (3) (e.g. NaH, NaOMe, t-BuOK, NaOH, KOH, $Na_2CO_3$, $K_2CO_3$, $NaHCO_3$, triethylamine, pyridine, dimethylaniline). The base may preferably be used from 1 to 3 equivalent to the activated radical to be used therein.

In the reaction (1) or (2), the activated radical $R_{13}$-Z, $R_{24}$-Z may preferably be used from 1 to 3 equivalent to the amine to be used therein, and in the reaction (3), the amine

may preferably be used in an excess to the compound of the formula (Im).

The reactions (1) to (3) can be carried out in the presence of an inert solvent (e.g. benzene, toluene, tetrahydrofuran, ether, dimethoxyethane, methanol, ethanol). The reaction conditions may vary depending upon the reaction temperature and the activated radicals to be used therein. The reaction temperature may be from 0° C. to boiling point of the solvent used.

When each of $R_{13}$ and $R_{24}$ means an alkyl group, an alkenyl group, an alkynyl group or an aralkyl group, oversubstitution may often occur giving a mixed product, and therefore in these cases, milder conditions may preferably be employed.

(Ec) via Hydrolysis

-continued
(Ec) via Hydrolysis

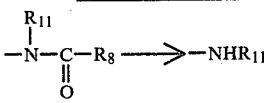 (1)

(wherein $R_8$ is a hydrogen atom, a $C_1$-$C_4$ alkyl group, a $C_1$-$C_3$ haloalkyl group, a $C_1$-$C_4$ alkoxy group or a benzyloxy group)

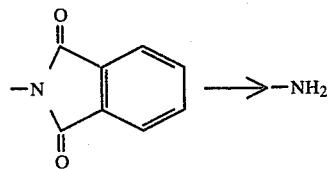 (2)

The reaction (1) or (2) may be effected by treating the amide, the urethane or the phthalimide under a basic or acidic aqueous medium.

Caustic alkalis such as sodium hydroxide, potassium hydroxide and barium hydroxide may preferably be used for these reactions, and hydrohalogenic acids such as hydrochloric acid, hydrobromic acid and hydroiodic acid may also preferably be used.

The reactions (1) and (2) may be carried out using a co-solvent such as methanol, ethanol, butanol, ethyleneglycol, dimethylformamide or dimethylsulfoxide. The reactions (1) and (2) may mostly be carried out by heating the reaction mixture at a temperature from room temperature to the refluxing temperature of the reaction system in order to complete the hydrolysis.

The reaction (2) may also be achieved by the modified method of Manske (J. Chem. Soc., 1926, 2348); namely, treatment of the phthalimide with hydrazine hydrate may afford the phthalhydrazide, and the resulting phthalhydrazide may easily be hydrolyzed by treatment with hydrochloric acid.

(Ed) via Rearrangement

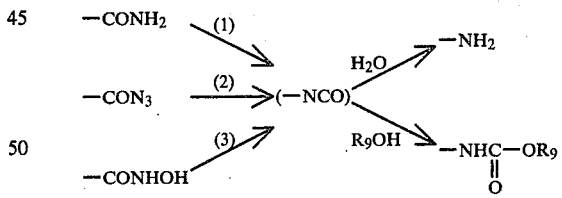

(wherein $R_9$ is a $C_1$-$C_4$ alkyl group or a benzyl group).

The types of the reactions (1), (2) and (3) are all well known rearrangement reactions; the reaction (1) is Hofmann rearrangement (Org. Reactions, 3, 267); the reaction (2) is Curtius rearrangement (Org. Reactions, 3, 337); and the reaction (3) is Lossen rearrangement (Chem. Review, 33, 209 (1943)).

By these reactions, the isocyanate may initially be formed, from which the amine may be obtained by hydrolysis, and the urethane may be obtained by treatment with an alcohol ($R_9$-OH).

The reaction (1) may be effected by treatment of the amide with an alkali hypohalite (e.g. sodium hypobromite, sodium hypochlorite). The reaction (2) or (3) may be effected by heating the acyl azide or the hydroxamic acid. The reaction (3) may also be effected by treating the hydroxamic acid with a base (e.g. sodium hydride).

The reactions (1) to (3) may generally be carried out in a suitable solvent (e.g. water, methanol, ethanol, tetrahydrofuran, benzene, toluene) at a temperature from room temperature to the refluxing temperature of the reaction system.

The isocyanate obtained as above may be hydrolyzed into the amine in a conventional way. For example, the hydrolysis can be carried out by treating the isocyanate with an alkali (e.g. NaOH, KOH) or an acid (e.g. HCl, $H_2SO_4$) in water or a mixture of water and an organic solvent (e.g. dioxane, ethyleneglycol, dimethylformamide) at a temperature ranging from room temperature to the refluxing temperature of the reaction system.

When the reaction (1), (2) or (3) is carried out in the presence of an alcohol ($R_9$-OH), the urethane may be obtained as a product of the rearrangement.

The heterotricyclic cage compound thus obtained can be separated from the reaction mixture and purified by the conventional procedures.

Method F

The compound of the formula (In):

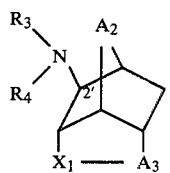

wherein $R_3$, $R_4$, $A_2$, $A_3$ and $X_1$ are each as defined above, can be prepared from the tricyclic cage compound having the formula (IIe):

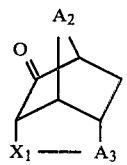

wherein $A_2$, $A_3$ and $X_1$ are each as defined above by the following method:

(Fa) via reduction

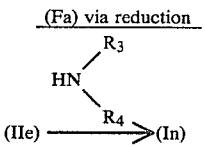

(wherein $R_3$ and $R_4$ are each as defined above)

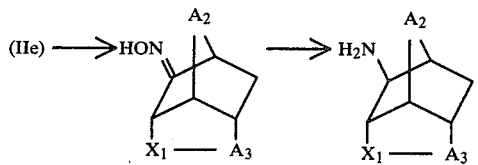

(wherein $A_2$, $A_3$ and $X_1$ are each as defined above).

The reaction (1) is known as the reductive amination and it may be effected by reacting the carbonyl compound with ammonia or an amine in the presence of a reducing agent such as a metal borohydride, an active metal and an acid or formic acid or its derivative in a solvent such as methanol, ethanol, benzene, toluene, and the like.

The reaction (2) is carried out by reacting the carbonyl compound with hydroxylamine, followed by reduction of the resulting oxime. This reduction may be preferably be carried out by treatment with a metal hydride compound such as lithium aluminum hydride, sodium trialkoxyaluminum hydride, sodium diethylaluminum hydride or sodium bis(methoxyethoxy)aluminum hydride in an inert solvent such as ether, tetrahydrofuran or toluene.

The reduction in the reaction (1) or (2) may be also effected by hydrogenation in the presence of a catalyst such as palladium charcoal, platinum oxide or Raney nickel in an inert solvent such as methanol, ethanol, benzene or toluene.

The temperature for the above reduction may vary depending on the type of reduction or reducing agent to be used therein, but these reactions (1) and (2) may generally be carried out at a temperature of from $-20°$ C. to the boiling point of the solvent to be used therein.

Method G

The compound of the formula (Io):

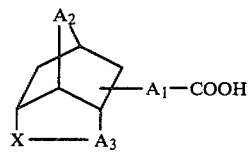

wherein $A_1$, $A_2$ and $A_3$ are each as defined above and X is —O— or —SO— (wherein n is 0, 1 or 2), can be prepared by hydrolysis of the compound of the formula (Ip):

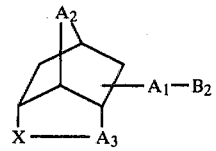

wherein $A_1$, $A_2$, $A_3$ and X are each as defined above and $R_2$ is a cyano group, a $C_2$-$C_5$ alkoxycarbonyl group or a carbamoyl group of the formula:

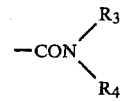

wherein $R_3$ and $R_4$ are each as defined above.

The hydrolysis may preferably be carried out by heating the compound of the formula (Ip) with a caustic alkali (e.g. sodium hydroxide, potassium hydroxide, barium hydroxide) in water or a mixture of water and an organic solvent at room temperature to the refluxing point of the reaction system. The objective compound of the formula (Io) can be isolated by acidifying the resulting reaction mixture. As the organic solvent, methanol, ethanol, butanol, ethyleneglycol, dimethylformamide, dimethylsulfoxide or the like may be used for this reaction.

The heterotricyclic cage compound thus obtained can be separated from the reaction mixture and purified by the conventional procedures.

Method H

The compound of the formula (Iq):

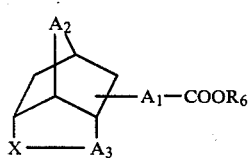

wherein $A_1$, $A_2$, $A_3$, X and $R_6$ are each as defined above, can be prepared by forming the alkoxycarbonyl group represented by —$COOR_6$ on the tricyclic ring by the following procedure:

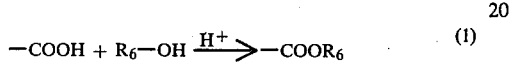

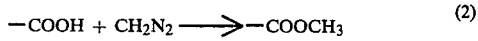

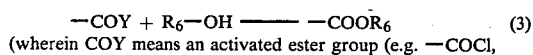

(wherein COY means an activated ester group (e.g. —COCl,

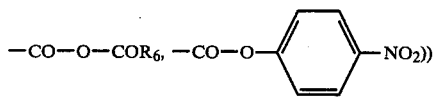

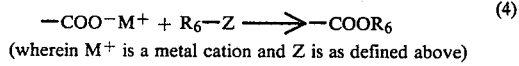

(wherein $M^+$ is a metal cation and Z is as defined above)

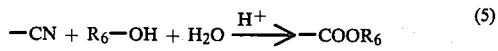

The reactions (1), (2), (3), (4) and (5) may be carried out in a usual manner. That is, the reaction (1) can be effected by heating the carboxy compound with the alcohol in the presence of an acid catalyst. The reaction (2) may be carried out by treating the carboxy compound with diazomethane at room temperature in an inert solvent such as ether or ethyl acetate. The reaction (3) may be effected by reacting the activated acid compound with the alcohol. In this reaction, some bases such as triethylamine, pyridine or dimethylaniline may preferably be used as a condensing agent. The reaction (4) can be effected by reacting the metal salt (M being, for instance, $Na^+$, $K^+$, $Mg^{++}$ or $Ag^+$) of the acid with the activated radical ($R_6$-Z). The reaction (5) can be effected by treatment of the cyano group with the alcohol and water in the presence of an acid catalyst.

The reaction (1), (3), (4) or (5) may be carried out in a suitable solvent such as methanol, ethanol, benzene, toluene, xylene, tetrahydrofuran or dimethylsulfoxide and the like at a temperature ranging from 0° C. to the refluxing temperature of the reaction system, preferably above room temperature.

The heterotricyclic cage compound thus obtained can be separated from the reaction mixture and purified by the conventional procedures.

Method I

The compound of the formula (Ir):

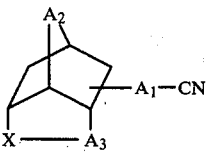

wherein $A_1$, $A_2$, $A_3$ and X are each as defined above, can be prepared by reacting the compound of the formula (Im):

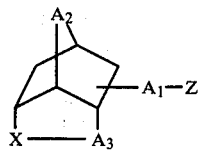

wherein $A_1$, $A_2$, $A_3$, X and Z are each as defined above, with a cyanide compound.

Examples of such cyanide compound are sodium cyanide, potassium cyanide, etc. The reaction may preferably be carried out in an inert solvent such as methanol, ethanol, tetrahydrofuran, benzene, toluene, dimethylformamide or dimethylsulfoxide. The temperature may be from room temperature to the boiling point of the solvent to be used therein.

The heterotricyclic cage compound thus obtained can be separated from the reaction mixture and purified by the conventional procedures.

Method J

The compound of the formula (Is):

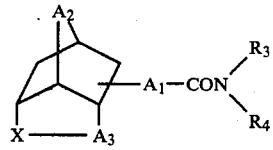

wherein $A_1$, $A_2$, $A_3$, X, $R_3$ and $R_4$ are each as defined above, can be prepared by forming the carbamoyl group via the following procedure:

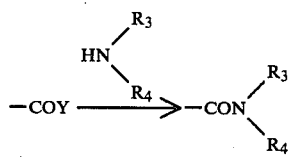

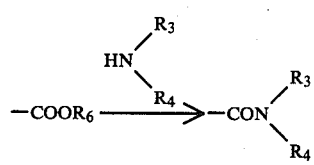

(wherein —COY and $R_6$ are each as defined above).

The reaction (1) may be carried out by reacting the activated acid radical with the amine

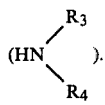

This reaction is preferably be carried out by using the amine in an excess amount, preferably in the presence of a solvent such as water, dioxane, ether, benzene or tetrahydrofuran.

The reaction (2) may be carried out by reacting the alkoxycarbonyl group with the amine, preferably in the presence of a solvent such as dioxane, water or tetrahydrofuran. These reactions may generally be conducted at a temperature from room temperature to the boiling point of the solvent used.

The heterotricyclic cage compound thus obtained can be separated from the reaction mixture and purified by the conventional procedures.

Method K (a) The compound of the formula (It):

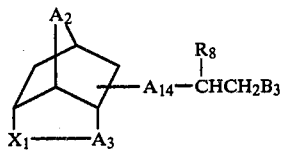

wherein $A_2$, $A_3$ and $X_1$ are each as defined above, $A_{14}$ is a single bond or a $C_1$-$C_3$ alkylene group bonding at 2-, 2'- or 3-position, $R_8$ is a hydrogen atom, a methyl group or an ethyl group and $B_3$ is a carboxy group, a $C_2$-$C_5$ alkoxycarbonyl group or a cyano group, can be prepared by hydrogenation of the compound of the formula (IIf):

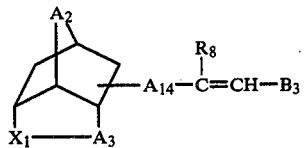

wherein $A_2$, $A_3$, $X_1$, $A_{14}$, $R_8$ and $B_3$ are each as defined above.

(b) The compound of the formula (Iu):

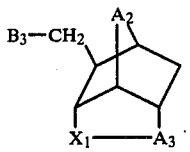

wherein $A_2$, $A_3$, $X_1$ and $B_3$ are each as defined above, can be prepared by hydrogenation of the formula (IIg):

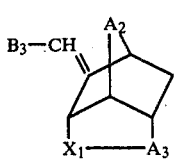

wherein $A_2$, $A_3$, $X_1$ and $B_3$ are each as defined above.

Hydrogenation may be carried out in the presence of a catalyst such as palladium on charcoal, platinum oxide or Raney nickel, and preferably with an inert solvent such as water, methanol, ethanol or toluene.

The temperature for the hydrogenation may vary depending on the catalyst to be used therein, but this reaction may generally be carried out at a temperature of from $-20°$ C. to the boiling point of the solvent to be used therein.

Method L

The compond of the formula (Iv):

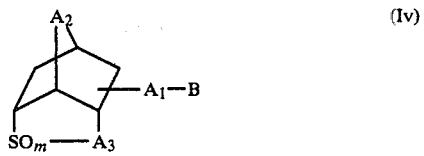

wherein $A_1$, $A_2$, $A_3$ and B are each as defined above and m is an integer of 1 or 2, can be prepared by reacting the compound of the formula (Iw):

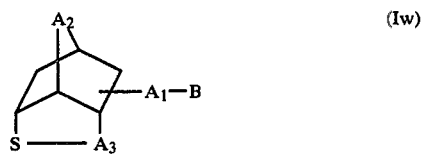

wherein $A_1$, $A_2$, $A_3$ and B are each as defined above, with an oxidizing agent.

Examples of the oxidizing agent are hydrogen peroxide, peracids (e.g. peracetic acid, perbenzoic acid, m-chloroperbenzoic acid), potassium permanganate, potassium persulfate, sodium hypochlorite, sodium metaperiodate, etc. The reaction may preferably be carried out in a solvent such as water, acetic acid, chloroform, dichloroethane, methanol, ethanol or benzene.

The oxidation may proceed in two steps: oxidation of the sulfide into the sulfoxide and that of the sulfoxide into the sulfone. The first step may proceed under milder conditions, e.g. at a low temperature ($-50°$ C. to room temperature) or with a low molar ratio of the oxidizing agent toward the substrate. Thus, the objective sulfoxide can substantially be obtained as a sole reaction product.

The oxidation of the sulfide or the sulfoxide into the sulfone may preferably be effected by using an excess amount of the oxidizing agent under a relatively high temperature, i.e. from room temperature to the boiling point of the solvent to be used.

The heterotricyclic cage compound thus obtained can be separated from the reaction mixture and purified by the conventional procedures.

The key intermediates of this invention can be prepared by the following methods:

Method M

The compound of the formula (IIb) (i.e. the starting compound for Method B):

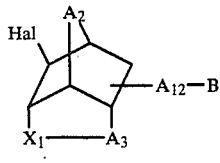

wherein $A_{12}$, $A_2$, $A_3$, $X_1$, B and Hal are each as defined above, can be prepared by reacting the compound of the formula (IIa):

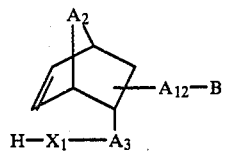

wherein $A_{12}$, $A_2$, $A_3$, $X_1$ and B are each as defined above, with a halogen compound.

Examples of the halogen compound are bromine, iodine, N-bromosuccinic imide (NBS) and so on. The reaction may preferably be carried out in an inert solvent such as water, carbon tetrachloride, chloroform, dichloroethane or tetrahydrofuran. The reaction proceeds generally at a temperature from 0° C. to room temperature.

Method N

The compound of the formula (IIc) (i.e. the starting compound in Method C):

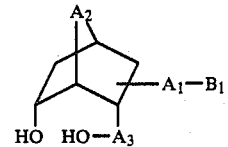

wherein $A_1$, $A_2$, $A_3$ and $B_1$ are each as defined above, can be prepared by reducing the compound of the formula (Ix):

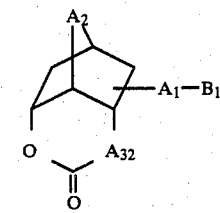

wherein $A_1$, $A_2$ and $B_1$ are each as defined above and $A_{32}$ is a single bond or a $C_1$-$C_3$ alkylene group, with a metal hydride compound.

A variety of metal hydride compounds which have a reducing capability toward a lactone moiety can be widely used (e.g. lithium aluminum hydride, sodium trialkoxyaluminum hydride, sodium diethylaluminum hydride, calcium borohydride, lithium borohydride). The metal hydride compound to be used therein may preferably be selected depending on the type of the side chain group ($B_1$) involved in the molecule of the compound (Ix). That is, when $B_1$ is susceptible toward a strong reducing agent such as lithium aluminum hydride, a milder reducing agent such as calcium borohydride or lithium borohydride may preferably be used.

The reaction is usually effected in an inert solvent such as ether, tetrahydrofuran, toluene or dimethoxyethane. The reaction temperature may vary depending on the type of the substrate or the reducing agent to be used therein, but may mostly be from −20° C. to the boiling point of the solvent to be used.

Method O

The compounds of the following formulae (the starting compounds for Method E):

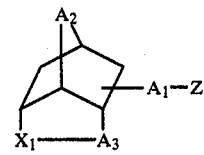

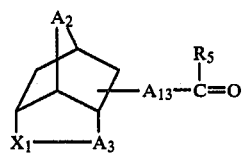

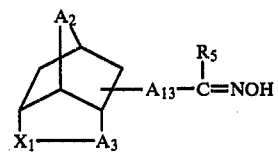

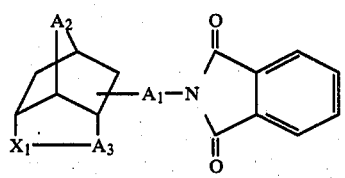

wherein $A_1$, $A_2$, $A_3$, $A_{13}$, $X_1$, Z and $R_5$ are each as defined above, can be prepared by formation of their functions according to conventional procedures.

Typical examples are illustrated as follows:

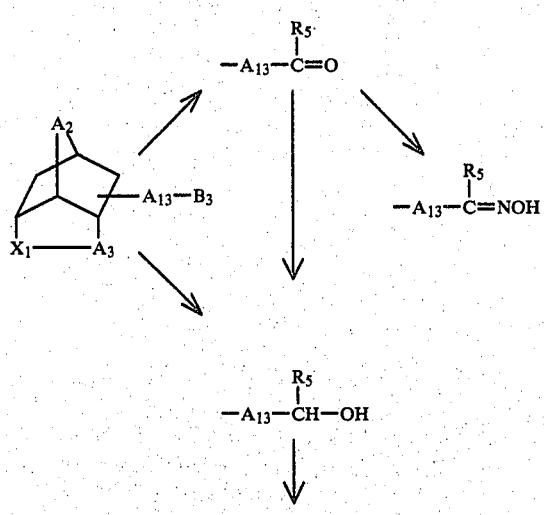

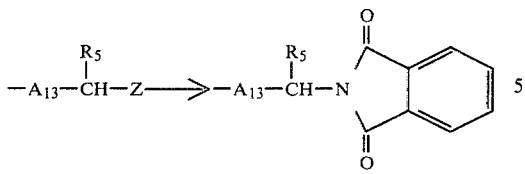

wherein B₃ is as defined above.

Method P

The compounds of the following formulae (IIe), (IIi) and (IIh), which are the starting compounds for Methods E, F and I, can be prepared by the series of the following reactions.

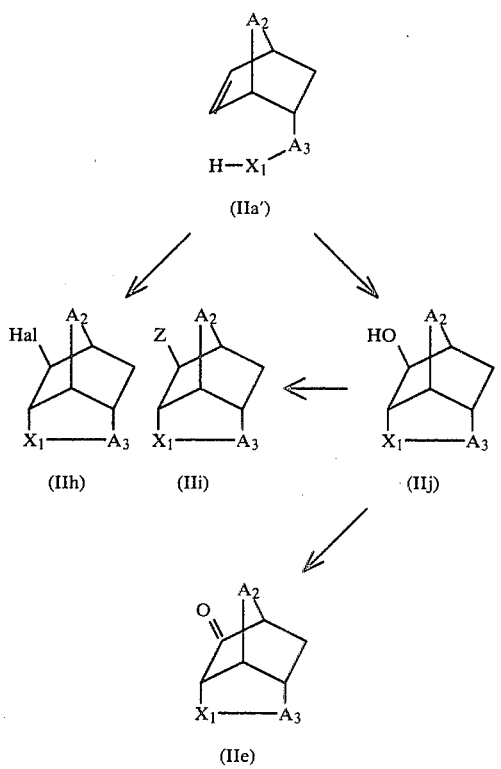

wherein A₂, A₃, X₁, Z and Hal are each as defined above.

The compound (IIh) can be prepared by reacting the compound (IIa′) with a halogen compound.

Examples of the halogen compound are bromine, iodine, N-bromosuccinic imide (NBS) and so on. The reaction may be preferably be carried out in an inert solvent such as water, carbon tetrachloride, chloroform, dichloroethane or tetrahydrofuran. The reaction proceeds generally at a temperature from 0° C. to room temperature.

Conversion of the compound (IIj) into the compound (IIi) may be carried out in a conventional way. That is, the compound (IIi) can be prepared by reacting the compound (IIj) with thionyl chloride, phosphorous halide, phosphorous oxyhalide, p-toluenesulfonyl chloride or metanesulfonylchloride. Examples of the residue of a strong acid represented by Z are chloride (—Cl), bromide (—Br), p-toluenesulfonate

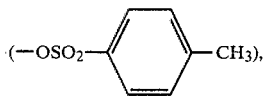

methanesulfonate (—OSO₂—CH₃), sulfate (—O—SO₂—O—) and so on. The reaction may preferably be carried out by using an organic or inorganic base.

The compound (IIe) can be prepared by reacting the compound (IIj) with an oxidizing agent. Examples of an oxidizing agent are dimethylsulfoxide, pyridimium chlorochromate, potassium permanganate, chromium trioxide, etc. The reaction may preferably be carried out in a solvent such as water, acetic acid, chloroform, dichloroethane or benzene.

The compound (IIj) can be prepared by oxidative cyclization of the compound (IIa′). That is, treatment of the compound (IIa′) with an oxidizing agent such as lead tetraacetate, mercuric salt (e.g. Hg(OCOCH₃)₂, Hg(OCOCCl₃)₂, Hg(OCOCF₃)₂, Hg(NO₃)₂), followed by oxidizing the resulting product with an ozone. The reaction may be carried out in the presence of an inert solvent (e.g. water, acetic acid, benzene, tetrahydrofuran, dioxane, dimethylformamide).

The heterotricyclic cage compound thus obtained can be separated from the reaction mixture by the conventional procedures.

Method Q

The compound of the formulae (IIf) and (IIg), which are the starting compounds for Method K, can be prepared by reacting the carbonyl compound shown below with the Witting reagent of the formula: (C₆H₅)₃P=CH-B₃ or

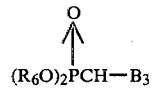

(wherein B₃ and R₆ are each as defined above).

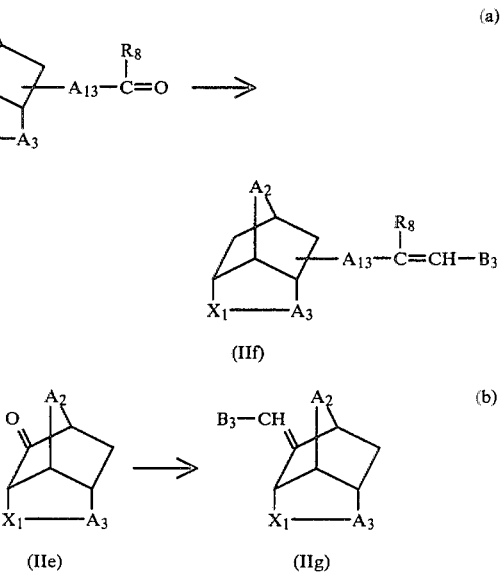

The reaction may be carried out in an inert solvent such as benzene, ether, tetrahydrofuran, methylene chloride, dimethylformamide, dimethylsulfoxide, alcohol or water at a temperature ranging from 0° C. to the boiling point of the solvent.

The starting materials used in the production of the compounds of the present invention can be prepared as follows:

Production of the Compounds (IIa)

The compounds of the formulae (IIa) and (IIa'), i.e. the common intermediates for the synthesis of the compound (I) of the present invention:

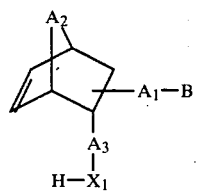
(IIa)

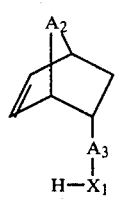
(IIa')

wherein $A_1$, $A_2$, $A_3$, $X_1$ and B are each as defined above, can be prepared by the Diels-Alder reaction, optionally followed by appropriate functional modifications.

[step 1] The Diels-Alder reaction

The first step for the synthesis of the compound (IIa) or (IIa') is the Diels-Alder reaction using an alicyclic diene compound of the formula (IIIa):

(IIIa)

wherein $A_2$ is as defined above with a dienophile of the formula (IIIb) or (IIIc):

(IIIb)

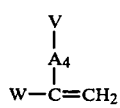
(IIIc)

wherein W is a carboxyl group, an alkoxycarbonyl group, a cyano group, a formyl group, an acyl group or a carbamoyl group, V is a hydrogen atom, a carboxyl group, an alkoxycarbonyl group, a cyano group, a formyl group, an acyl group, a halogen atom or a hydroxyl group and $A_4$ is a single bond or a lower alkylene group.

The products, i.e. the diene adducts (IIk) and (III), obtained by this reaction are shown as follows:

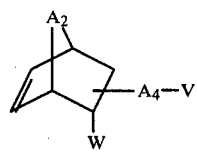
(IIk)

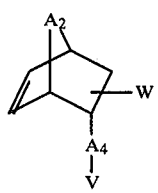
(III)

wherein $A_2$, $A_4$, W and V are each as defined above.

This process can be carried out in a conventional manner as disclosed, for example, in H. Wollweber in "Methoden der Organischen Chemie (Houben-Wyle)", Band V/IC, Kohlenwasserstoffe III, Georg Thieme (1970), p. 977–1139, M. P. Kloetzel, Org. React., 4, 1–59 (1948); H. L. Holmes, ibid., 4, 60–173 (1948); L. W. Butz, A. W. Rytina, ibid., 5, 136–192 (1949).

The diene adducts (IIk) and (III) thus prepared can be separated from each other by a conventional procedure such as chromatography or recrystallization.

[step 2] Functional modification

The second step for the synthesis of the compound (IIa) or (IIa') is the transformation of the group with the endo-orientation of the diene adduct obtained above into the group ($—A_3—X_1—H$) of the compound (IIa) or (IIa'):

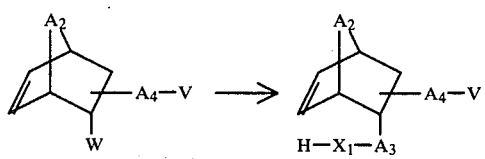

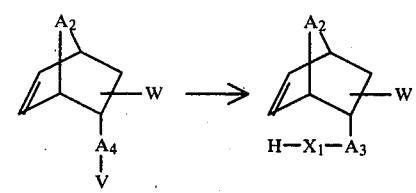

The transformation of the other group of the diene adduct into the group ($—A_1—B$) of the compound (IIa) may be carried out before, after or during the aforesaid transformation of the endo group:

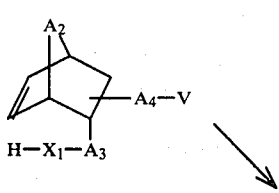

-continued

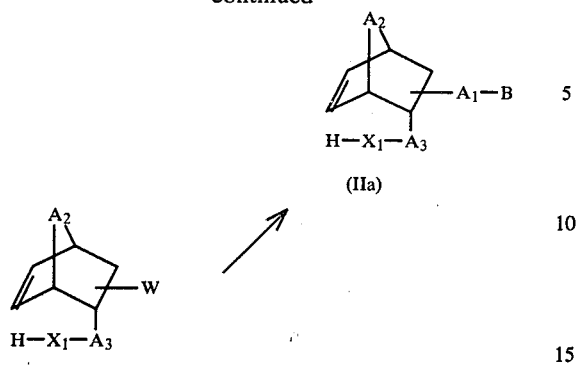

The modification of the functional groups of the diene adducts may be carried out by using a conventional procedure such as hydrolysis, reduction or thiolation.

For example, the compounds (IIa) wherein $-A_3-X_1-H$ is hydroxymethyl, β-hydroxyethyl, thiolmethyl or carboxy may be obtained from alkoxycarbonyl, alkoxycarbonylmethyl, halomethyl by reduction, thiolation or hydrolysis.

The diene (IIIa) to be used is such an alicyclic diene compound as cyclopentadiene, 1,3-cyclohexadiene or cycloheptatriene.

The followings are the typical examples of the diene adducts to be used in the production of the compound (IIa):

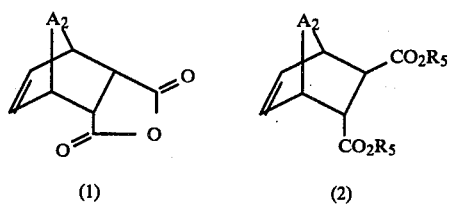

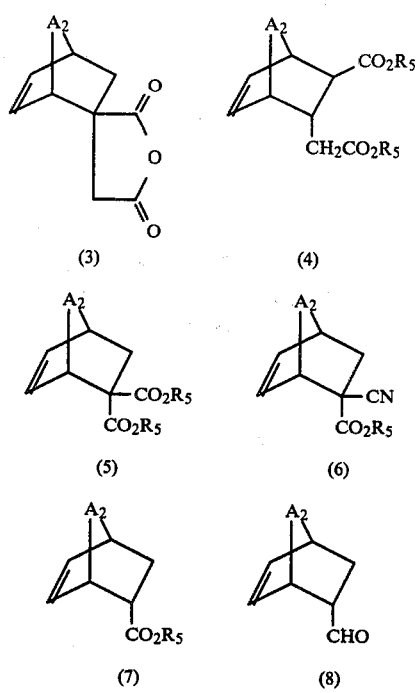

wherein $A_2$ and $R_5$ are each as defined above.

Among the diene adducts, those of the formulae (1) ($A_1=CH_2$, $CH_2CH_2$, cyclopropylene), (2) ($A_1=CH_2$, $CH_2CH_2$), (3) ($A_1=CH_2$), (7) ($A_1=CH_2$, $CH_2CH_2$) and (8) ($A_1=CH_2$, $CH_2CH_2$) are already known.

Some of the typical transformation starting from the diene adduct into the objective compound (I) of the present invention are illustrated in Charts A to E.

Chart A

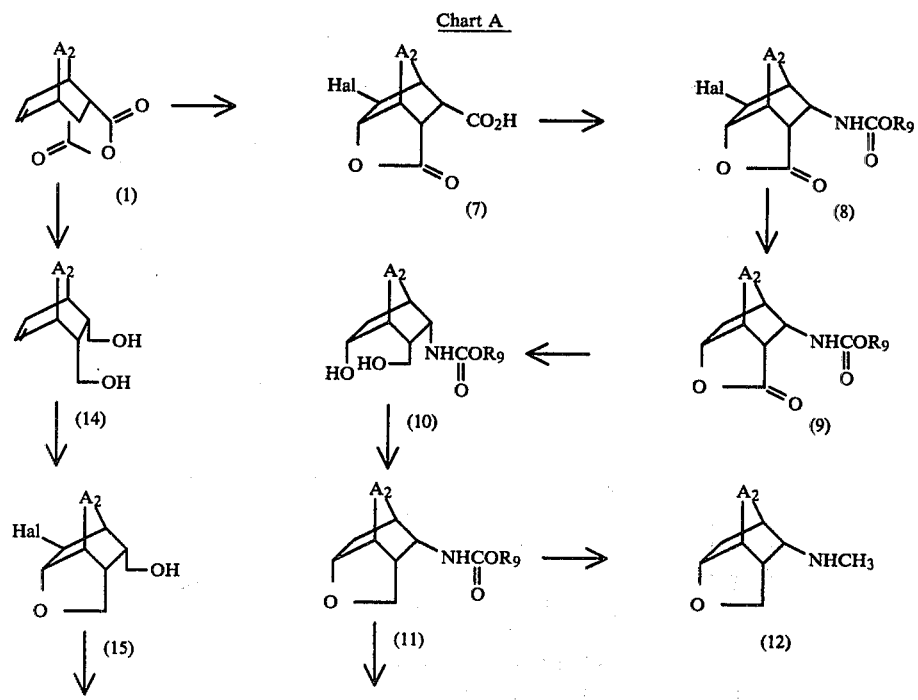

Chart A

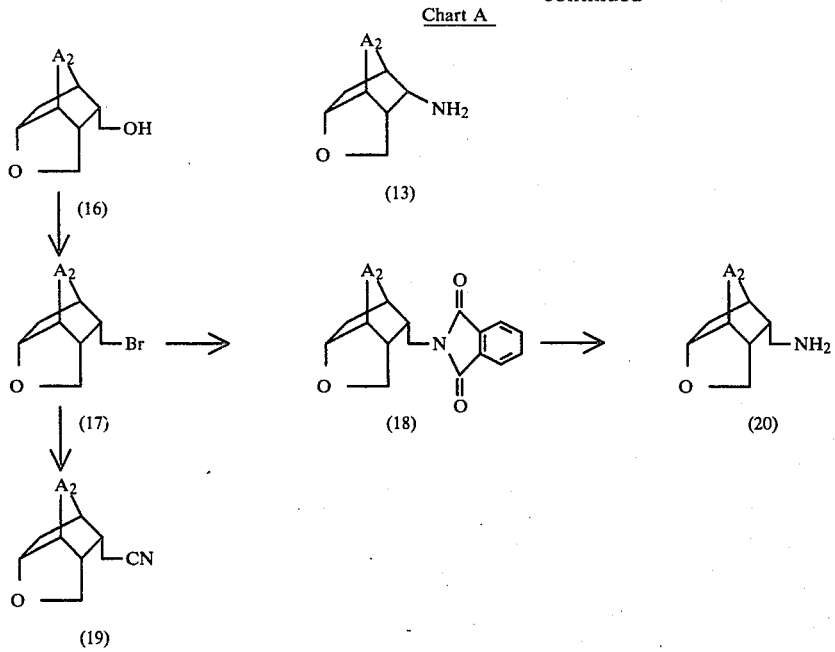

wherein Hal, $A_2$ and $R_9$ are each as defined above.

a-1

The compound (1: $A_2$=$CH_2CH_2$) was obtained by the method of J. O. C., 26, 2025 (1961).

The compound (7) can be obtained from the compound (1) by hydrolysis and iodo-lactonization.

Compound (1: $A_2$=$CH_2CH_2$)→Compound (3-5) (Example 3)

The acid azide of the compound (7), which can be obtained by reacting the acid chloride or mixed-anhydride of the compound (7) with sodium azide, can be transformed to the compound (8) with an alcohol under heating.

Compound (3-5)→Compound (4-3) (Example 4)

Dehalogenation of the compound (8) with tributyltin hydride gives the lactone (9).

Compound (4-3)→Compound (7-5) (Example 7)

Reduction of the compound (9) with $LiBH_4$ or $Ca(BH_4)_2$ gives the diol compound (10).

Compound (7-5)→Compound (9-4) (Example 9)

Dehydration of the compound (10) with p-tosyl chloride and pyridine gives the ether (1).

Compound (9-4)→Compound (11-4) (Example 11)

Hydrolysis of the compound (11) gives the amine compound (13) and reduction of the compound (11) with $LiAlH_4$ gives the compound (12).

Compound (11-4)→Compound (12-4) (Example 12)
Compound (11-4)→Compound (18-3) (Example 18)

a-2

Reduction of the compound (1) with $LiAlH_4$ gives the diol compound (14).

(Example 21)

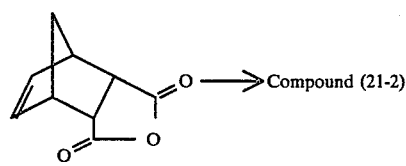→Compound (21-2)

(Example 21)

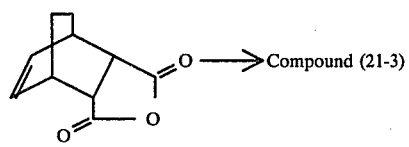→Compound (21-3)

Haloetherization of the compound (14) with NBS gives the ether (15).

Compound (21-2)→Compound (17-2) (Example 17)
Compound (21-3)→Compound (17-3) (Example 17)

Dehalogenation of the compound (15) with tributyltin hydride gives the ether (16).

Compound (17-2)→Compound (8-4) (Example 8)
Compound (17-3)→Compound (8-5) (Example 8)

Oxymercuration-demercuration of the compound (14) with mercuric acetate and sodium borohydride gives the ether (16).

Compound (21-2)→Compound (15-3) (Example 15)
Compound (21-3)→Compound (15-4) (Example 15)

Toxylation and halogenation of the compound (16) with tosyl chloride-pyridine and $LiBr.H_2O$ give the bromide (17).

Compound (8-4)→Compound (22-2) (Example 22)
Compound (8-5)→Compound (22-3) (Example 22)
Compound (22-2)→Compound (23-2) (Example 23)
Compound (22-3)→Compound (23-3) (Example 23)

Phthalimidation of the compound (17) with potassium phthalimide gives the compound (18).

Compound (23-2)→Compound (24-2) (Example 24)
Compound (23-3)→Compound (24-3) (Example 24)

Hydrolysis of the compound (18) gives the amine compound (20).

Compound (24-2)→Compound (25-2) (Example 25)
Compound (24-3)→Compound (25-3) (Example 25)

a-3

Cyanation of the compound (17: $A_2$=$CH_2CH_2$) with potassium cyanide gives the nitrile compound (19).

Compound (23-3)→Compound (57-2) (Example 57).

Chart B

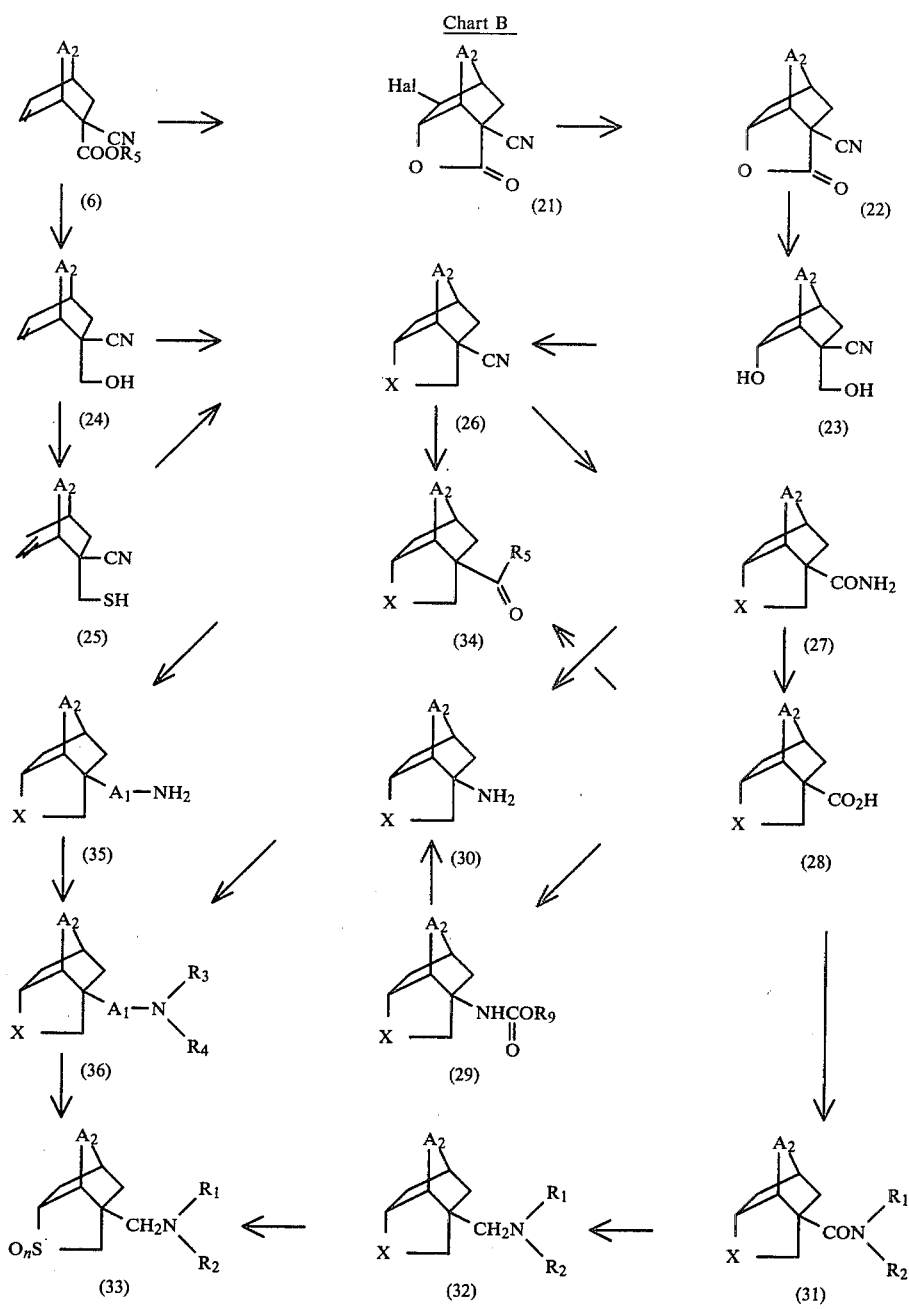

wherein $A_2$, Hal, $R_1$, $R_2$, $R_3$, $R_4$, $R_5$, $R_9$, X and n are each as defined above.

b-1

The compound (6: $A_2$=$CH_2$), which can be obtained from a 1,3-diene compound and α-cyanoacrylate, can be hydrolyzed and iodo-lactonized to afford the compound (21).

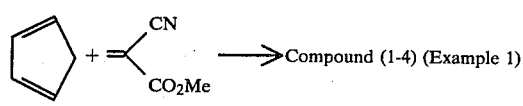→Compound (1-4) (Example 1)

Compound (1-4)→Compound (2-3) (Example 2)
Compound (2-3)→Compound (3-3) (Example 3)

The transformation of the compound (21) to the compound (26) (X=O) can be achieved by the similar procedure to the one as described in Chart A a-1 [cf. the transformation from the compound (8) to the compound (11)].

Compound (3-3)→Compound (7-6) (Example 7)
Compound (7-6)→Compound (10-1) (Example 10)
Compound (10-1)→Compound (11-8) (Example 11)

The compound (26: $A_2$=$CH_2$, $CH_2CH_2$, X=O) can also be obtained from the compound (24) by the oxymercuration-demercuration procedure.

Compound (1-4)→Compound (14-2) (Example 14)
Compound (1-5)→Compound (14-3) (Example 14)
Compound (14-2)→Compound (15-5) (Example 15)
Compound (14-3)→Compound (15-6) (Example 15)

The compound (26: $A_2$=$CH_2$, $CH_2CH_2$, X=O) can also be obtained from the compound (24) by the halo-etherization followed by the reduction.
Compound (14-2)→Compound (17-4) (Example 17)
Compound (14-3)→Compound (17-5) (Example 17)
Compound (17-4)→Compound (8-1) (Example 8)
Compound (17-5)→Compound (8-2) (example 8)

b-2

The compound (25) can be prepared from the compound (24) by halogenation of the hydroxyl group and thiolation of the resulting product with sodium hydrosulfite.

The compound (26) (X=S) can be prepared from the compound (25) by cyclization with a base catalyst (e.g. sodium hydroxide, triethylamine).
Compound (15-2)→Compound (45-2) (Example 45)
Compound (45-2)→Compound (51-1) (Example 51)
Compound (51-1)→Compound (52-1) (Example 52)

Partial hydrolysis of the compound (26) gives the compound (27).
Compound (8-1)→Compound (20-1) (Example 20)
Compound (8-2)→Compound (20-2) (Example 20)

The compound (30) can be prepared from the compound (27) by Hofmann rearrangement or by a sequence of hydrolysis, Curtius reaction and hydrolysis [(27)→(28)→(29)→(30)].
Hofmann rearrangement:
Compound (20-1)→Compound (26-1) (Example 26)
Compound (20-1)→Compound (26-2) (Example 26)
Curtius reaction:
Compound (8-1)→Compound (13-1) (Example 13)
Compound (8-2)→Compound (13-2) (Example 13)
Compound (13-1)→Compound (6-1) (Example 6)
Compound (13-2)→Compound (6-2) (Example 6)
Compound (6-1)→Compound (12-1) (Example 12)
Compound (6-2)→Compound (12-3) (Example 12)

The compound (35) can be prepared from the compound (26) by a sequence of alkylation with Grignard reagent or alkyl lithium, oxidation and reduction.
Compound (8-2)→Compound (43-1) (Example 43)
Compound (43-1)→Compound (43-2) (Example 43)
Compound (43-2)→Compound (44-1) (Example 44)

The compound (34) ($R_5$=H) can be prepared from the compound (28) by a sequence of reduction of the carboxyl group and oxidation of the resulting hydroxyl group.
Compound (13-2)→Compound (21-5) (Example 21)
Compound (21-5)→Compound (31-1) (Example 31)

The compound (35) can be prepared from the compound (34) by a sequence of the Witting reaction with triphenyl cyanomethylene phosphorane, hydrogenation of the resulting double bond and reduction of the cyano group.
Compound (31-1)→Compound (34-1) (Example 34)
Compound (34-1)→Compound (35-1) (Example 35)
Compound (35-1)→Compound (27-4) (Example 27)
Compound (8-1)→Compound (27-1) (Example 27)
Compound (8-2)→Compound (27-2) (Example 27)
Compound (52-1)→Compound (53-1) (Example 53)

The compound (36) can be prepared from the compound (30) or (35) by a sequence of alkylation.
Compound (6-1)→Compound (18-1) (Example 18)
Compound (6-2)→Compound (18-2) (Example 18)
Compound (18-1)→Compound (19-1) (Example 19)
Compound (18-2)→Compound (19-2) (Example 19)
Compound (19-1)→Compound (18-4) (Example 18)
Compound (19-2)→Compound (18-5) (Example 18)
Compound (27-2)→Compound (40-1) (Example 40)
Compound (40-1)→Compound (42-1) (Example 42)
Compound (40-1)→Compound (42-2) (Example 42)
Compound (27-2)→Compound (50-1) (Example 50)
Compound (27-2)→Compound (19-3) (Example 19)
Compound (19-3)→Compound (59-1) (Example 59)
Compound (59-1)→Compound (36-1) (Example 36)

The compound (33) can be prepared from the compound (28) by a sequence of amidation, reduction and oxidation [(28)→(31)→(32)→(33)].
Compound (13-1)→Compound (28-3) (Example 28)
Compound (13-1)→Compound (28-4) (Example 28)
Compound (13-1)→Compound (28-5) (Example 28)
Compound (13-2)→Compound (28-6) (Example 28)
Compound (28-3)→Compound (41-2) (Example 41)
Compound (28-4)→Compound (41-2) (Example 41)
Compound (28-5)→Compound (41-3) (Example 41)
Compound (28-6)→Compound (41-4) (Example 41)
Compound (53-1)→Compound (41-5) (Example 41)
Compound (62-1)→Compound (54-2) (Example 54)
Compound (53-1)→Compound (55-1) (Example 55)
Compound (62-1)→Compound (55-2) (Example 55)

The compound (36) can be prepared from the compound (34) by a reductive amination.
Compound (43-1)→Compound (63-1) (Example 63)

Chart C

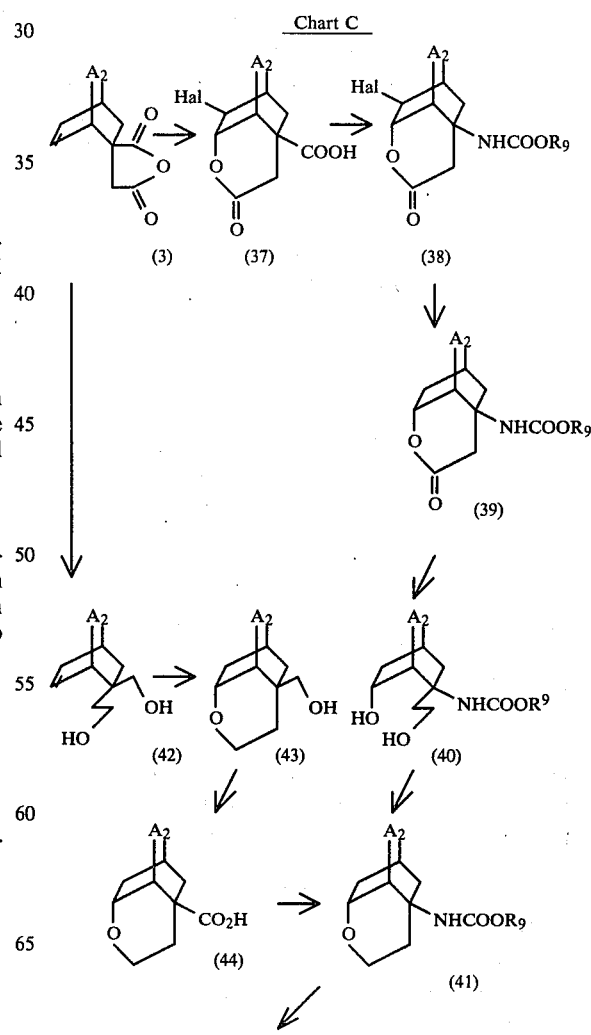

-continued
Chart C

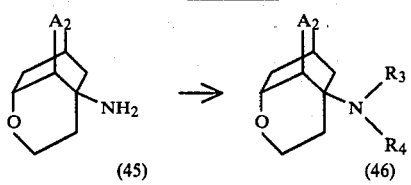

wherein $A_2$, Hal, $R_3$, $R_4$ and $R_9$ are each as defined above.

The compound (3), which can be obtained from a 1,3-diene compound and itaconic acid anhydride, can be hydrolyzed and iodo-lactonized to afford the compound (37).

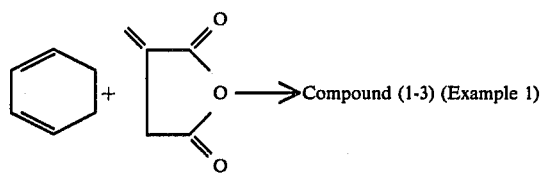

Compound (1-3)→Compound (3-4) (Example 3)

The transformation of the compound (37) to the compound (41) can be achieved by the similar procedure to the one as described in Chart A a-1 [cf. the transformation from the compound (7) to the compound (11)].

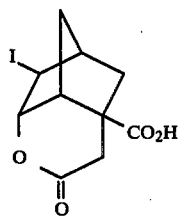

is obtained by the method of J. O. C., 23, 626 (1958).

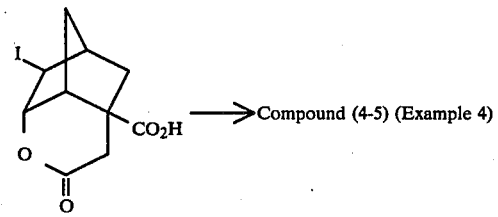

Compound (3-4)→Compound (4-4) (Example 4)
Compound (4-4)→Compound (7-4) (Example 7)
Compound (4-5)→Compound (7-3) (Example 7)
Compound (7-4)→Compound (9-6) (Example 9)
Compound (7-3)→Compound (9-5) (Example 9)
Compound (9-6)→Compound (11-6) (Example 11)
Compound (9-5)→Compound (11-5) (Example 11)

The compound (42) can be obtained from the compound (3) by reducing with LiAlH$_4$.

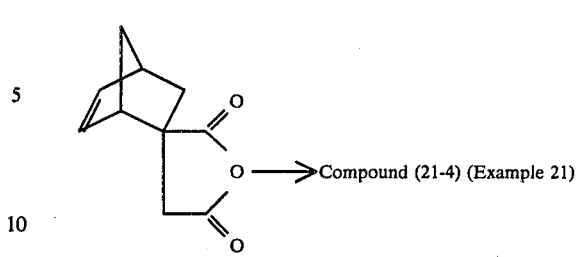

The compound (41) can be prepared from the compound (42) by a sequence of oxymercuration-demercuration, oxidation and Curtius reaction.
Compound (21-4)→Compound (16-2) (Example 16)
Compound (16-2)→Compound (30-1) (Example 30)
Compound (30-1)→Compound (6-3) (Example 6)

The transformation of the compound (41) to the compound (46) can be achieved by the similar procedure to the one as described in Chart B [cf. the transformation from the compound (35) to the compound (36)].
Compound (11-5)→Compound (12-5) (Example 12)
Compound (11-6)→Compound (12-7) (Example 12)

Chart D

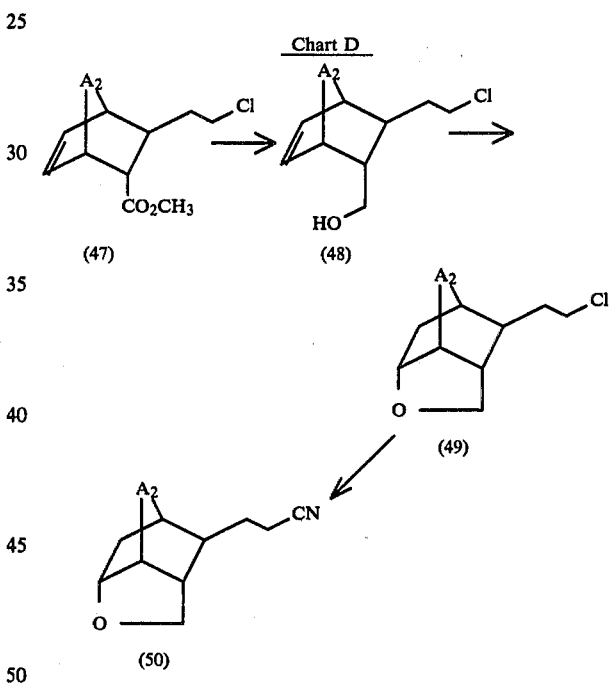

wherein $A_2$ is as defined above.

The compound (47), which can be obtained from a 1,3-diene compound and methyl-2-($\beta$-chloroethyl)acrylate can be reduced, oxymercurated and demercurated to afford the compound (49).

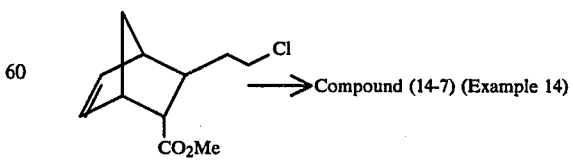

Compound (14-7)→Compound (15-11) (Example 15)
Cyanation of the compound (49) with potassium cyanide gives the cyano compound (50).
Compound (15-11)→Compound (57-1) (Example 58)

Chart E

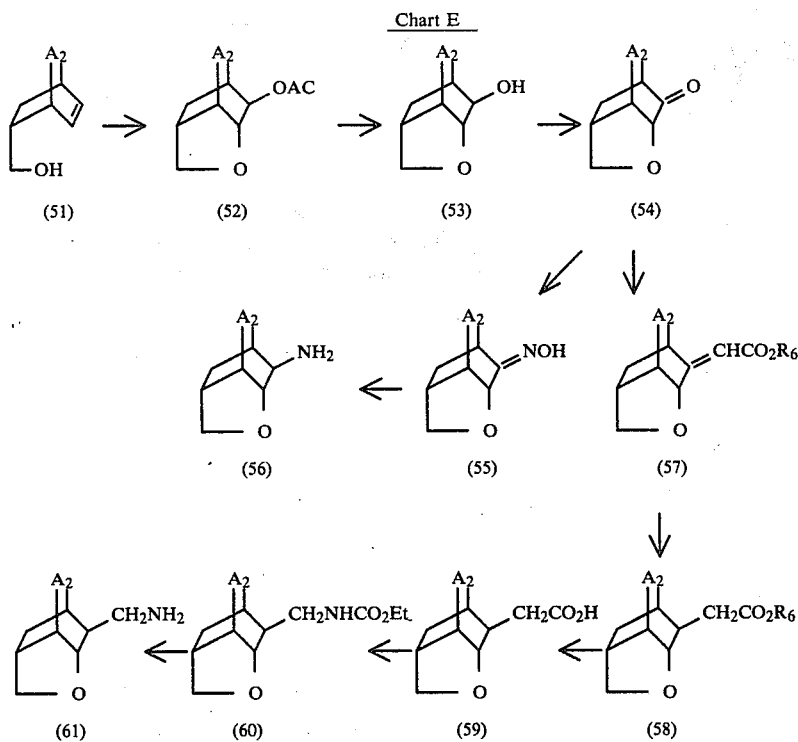

wherein A₂ and R₆ are each as defined above.

e-1

The compound (52: A₂=CH₂CH₂) can be obtained from the compound (51) by oxy-acetoxylation.

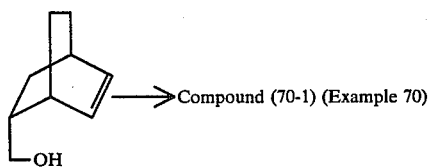

Hydrolysis of the compound (52: A₂=CH₂, CH₂CH₂) gives the alcohol compound (53).
Compound (70-1)→Compound (2-5) (Example 2)

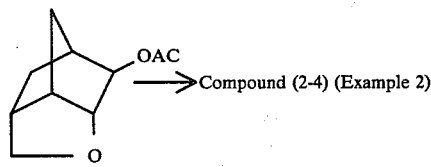

THL., 1165 (1964)

Oxidation of the compound (53) with dimethylsulfoxide-dicyclohexylcarbodiimide gives the ketone (54).
Compound (2-5)→Compound (31-3) (Example 31)
Compound (2-4)→Compound (31-2) (Example 31)
The compound (56) are obtained by reduction of the compound (55) with lithium aluminium hydride.
Compound (31-3)→Compound (68-3) (Example 68)
Compound (68-3)→Compound (44-4) (Example 44)
Compound (31-2)→Compound (68-2) (Example 44)
Compound (68-2)→Compound (44-3) (Example 44)

e-2

The Witting reaction of the compound (54) gives the olefinic ester (57).
Compound (31-3)→Compound (71-1) (Example 71)
The hydrogenation of the compound (57) gives the compound (58).
Compound (71-1)→Compound (35-2) (Example 35)
The compound (61) can be achieved by the similar procedure to the one as described in Chart B b-2.
Compound (35-2)→Compound (2-6) (Example 2)
Compound (2-6)→Compound (4-7) (Example 4)
Compound (4-7)→Compound (12-10) (Example 12)

As to the production of the compounds (I) of the invention, some typical procedures have hereinabove illustrated in detail. However, their production procedures are not restricted to them. Some other typical procedures, which are supported by the working examples as hereinafter set forth, are shown in the following scheme:

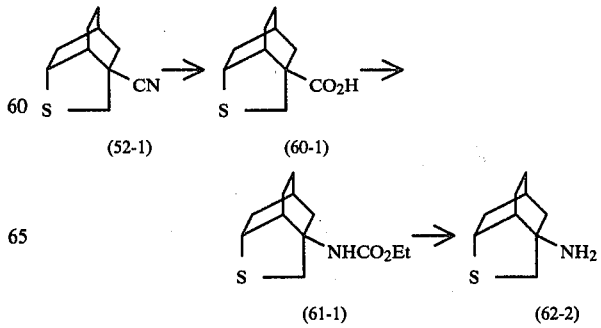

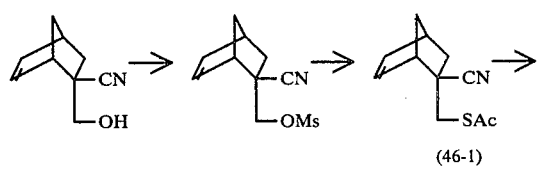
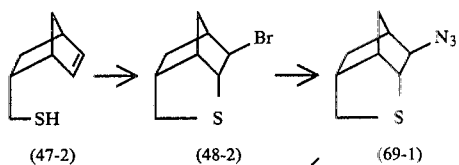
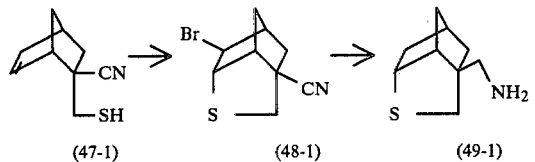
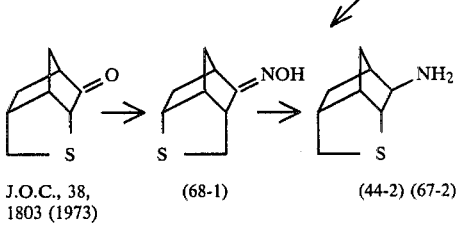
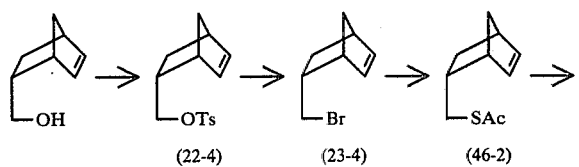
J.O.C., 38, 1803 (1973)
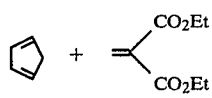
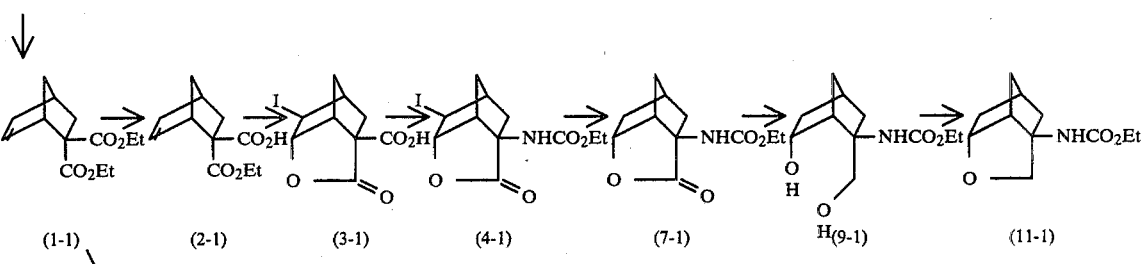
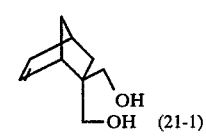
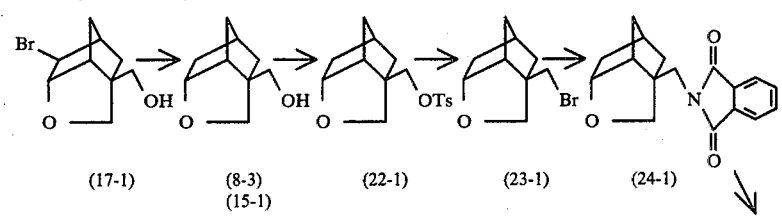
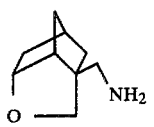
(25-1)
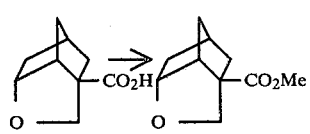

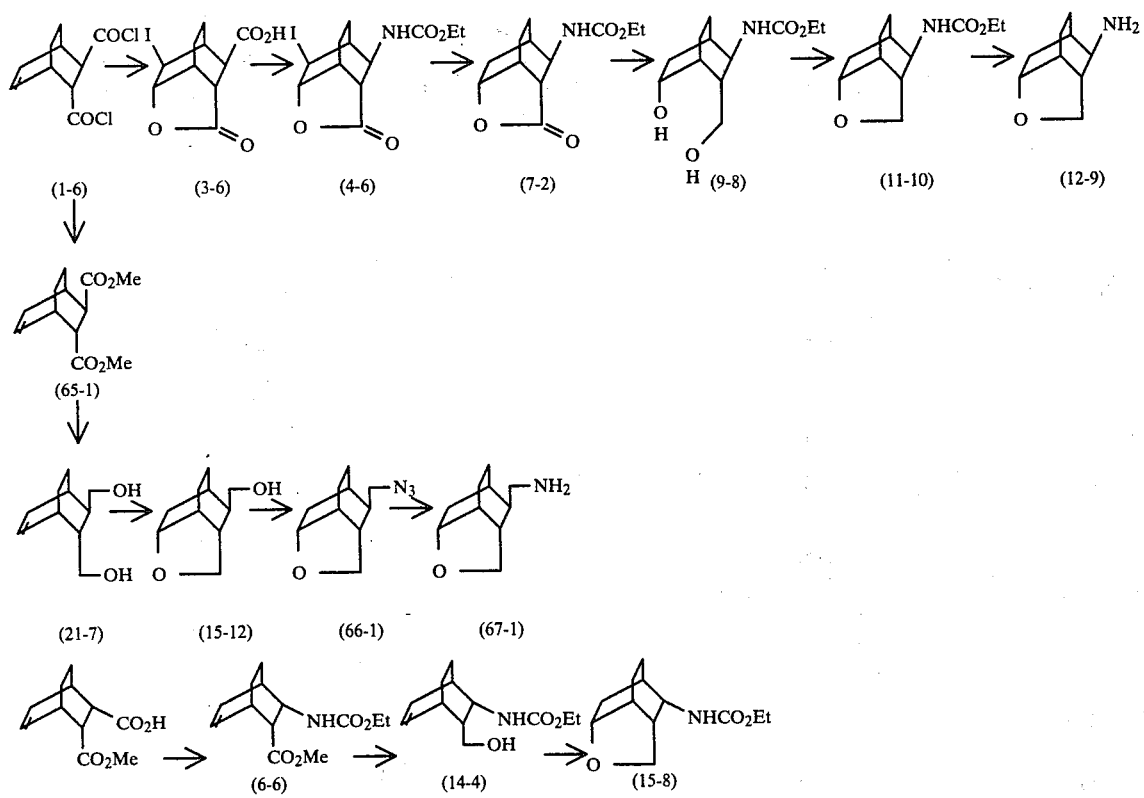
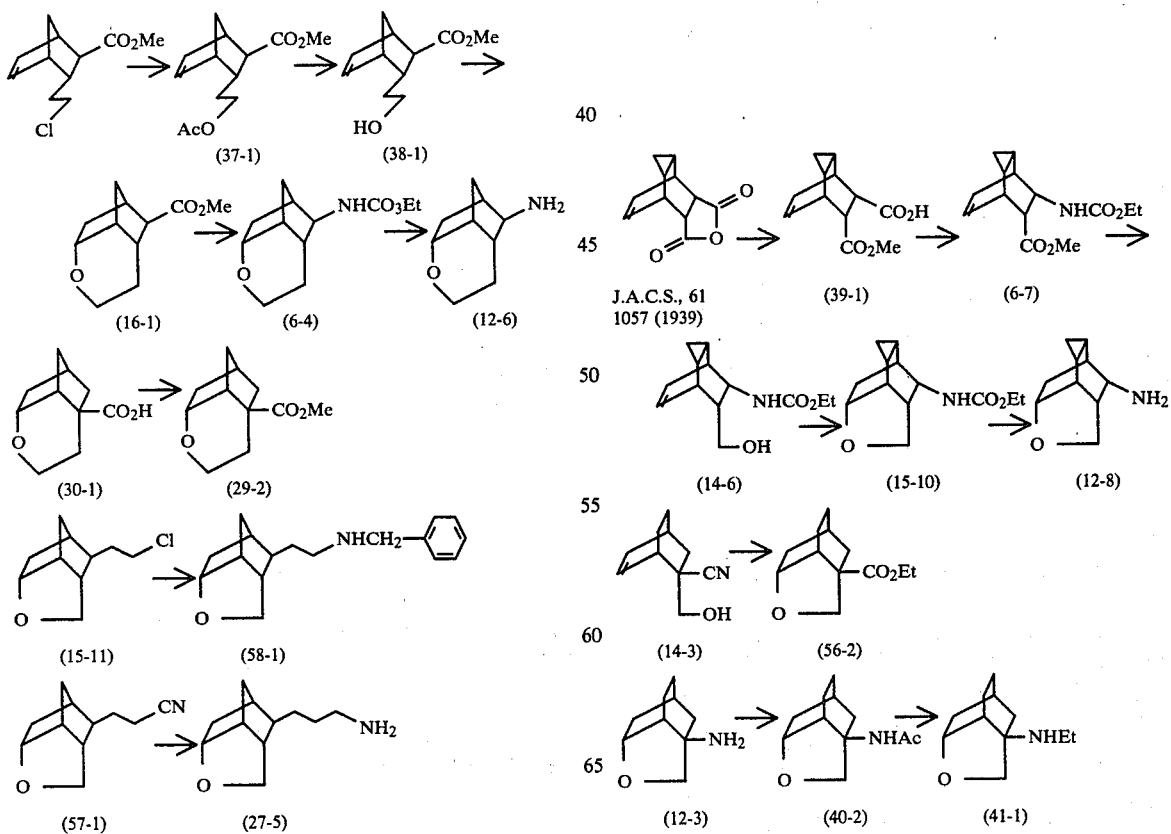

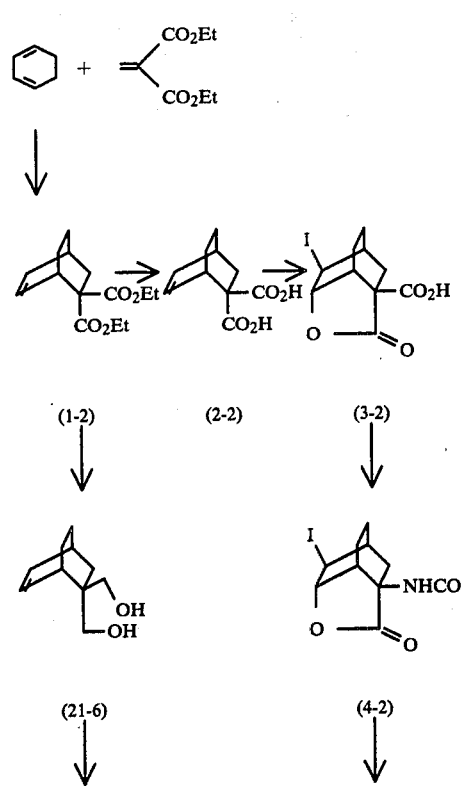
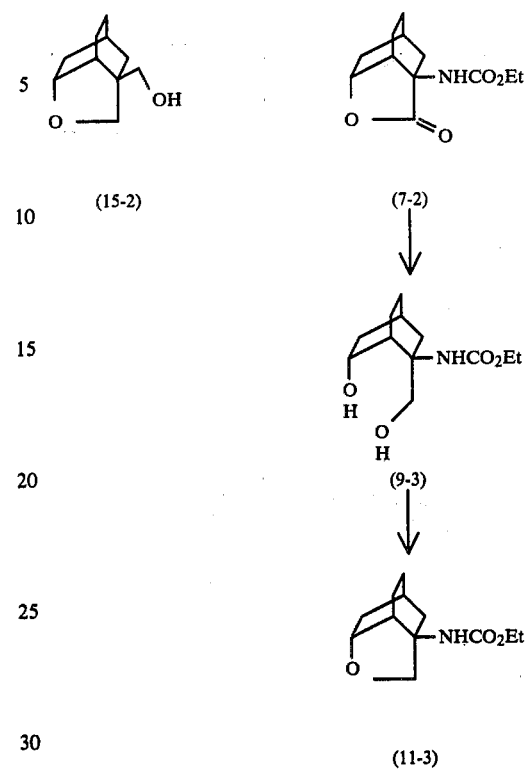

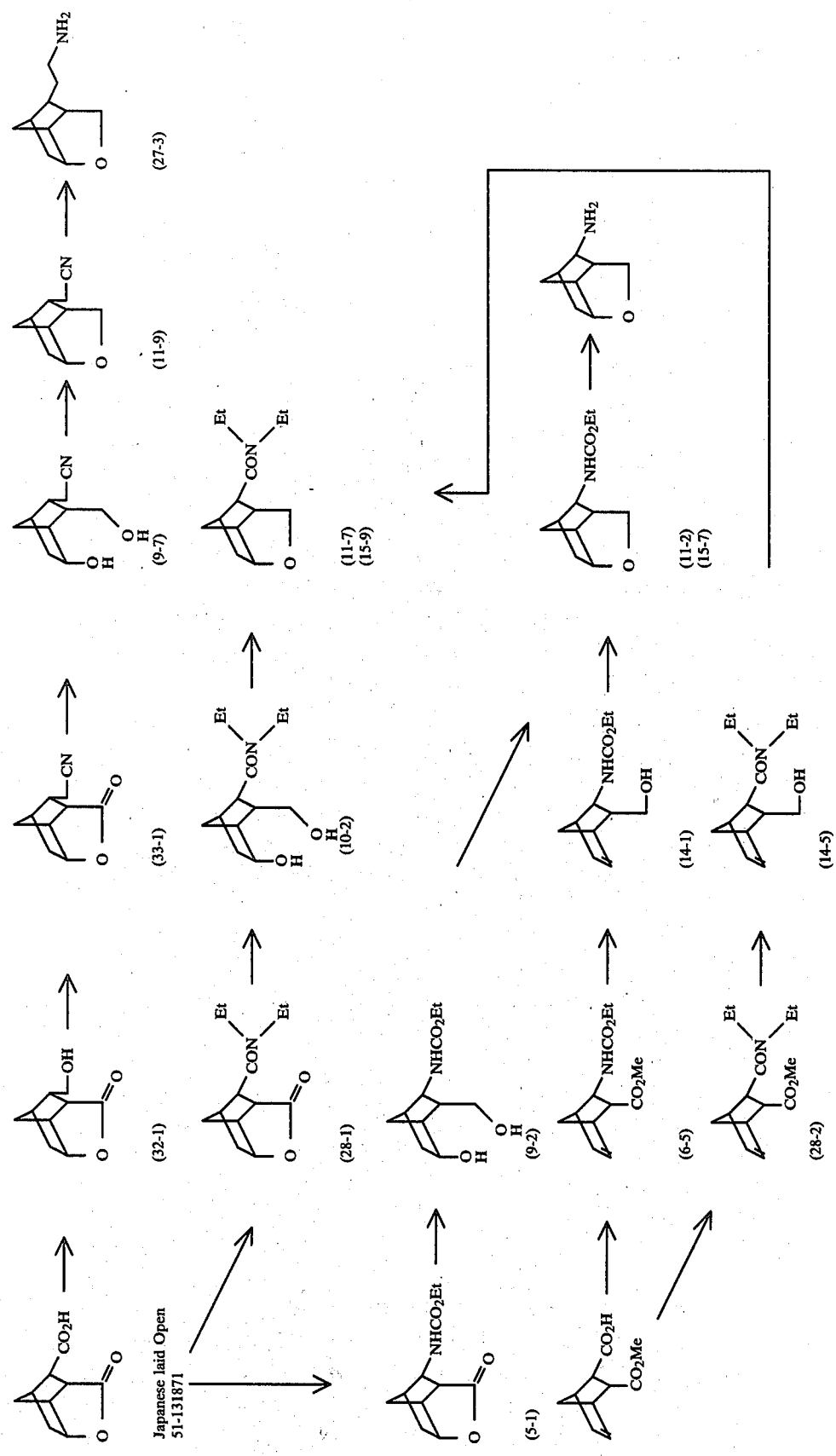

Some of the skeletons of the compounds obtained by the invention are designated according to the following common names, and the others are based on the nomenclature of IUPAC.

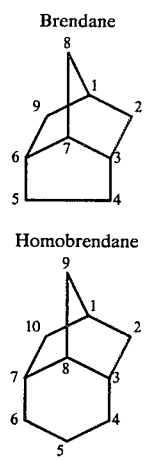

Brendane (a)

Homobrendane (b)

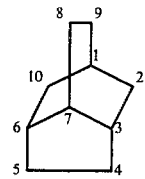

Isotwistane (c)

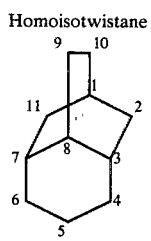

Homoisotwistane (d)

The following examples are given for the purpose of illustration and it is not intended to limit the invention. For better understanding of the correlations among the compounds in these examples, the following scheme are presented:

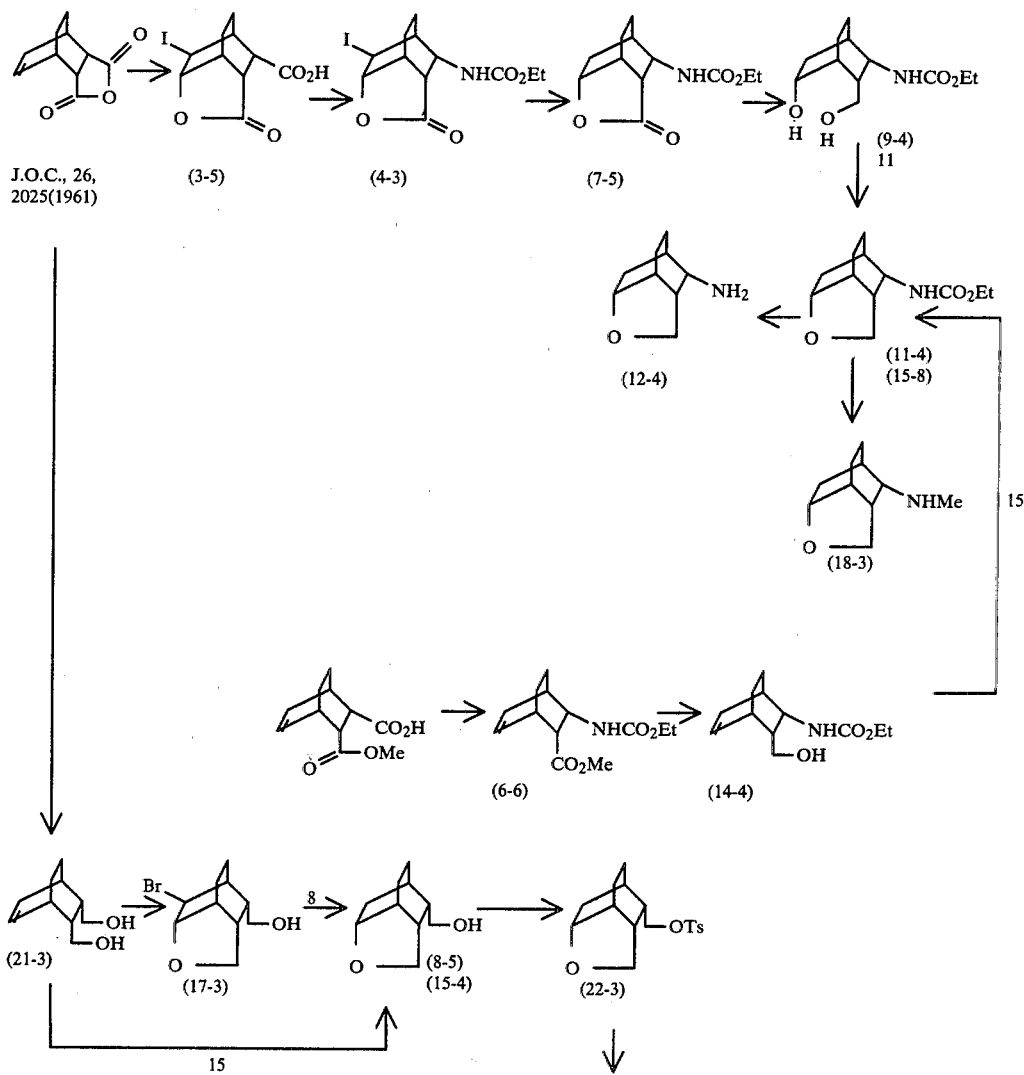

-continued
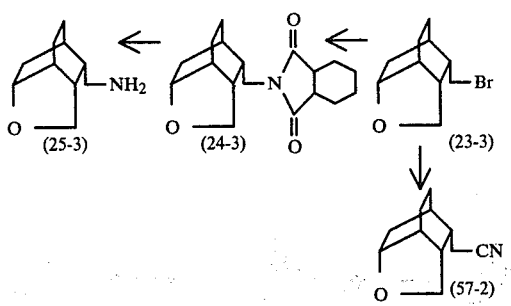
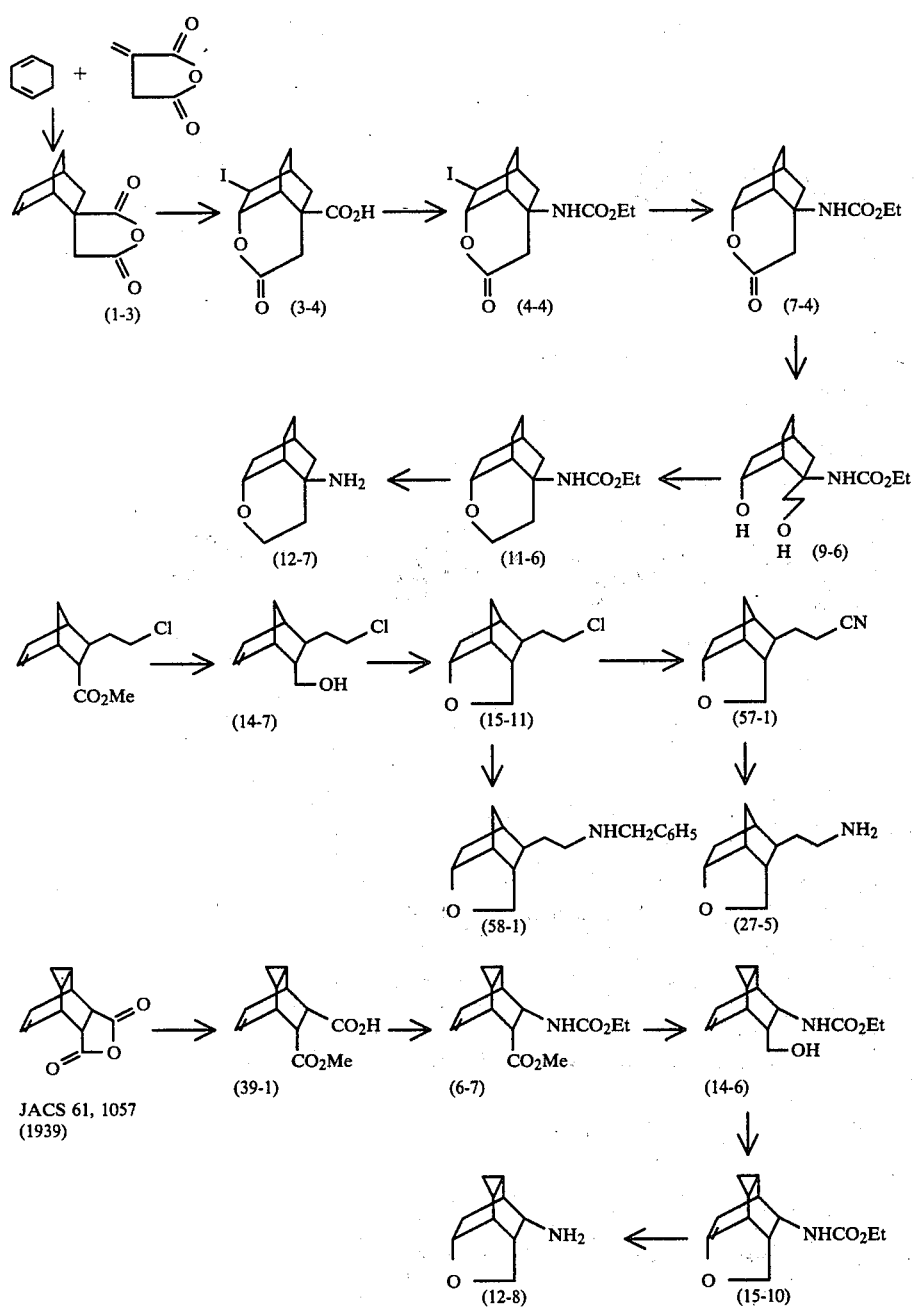

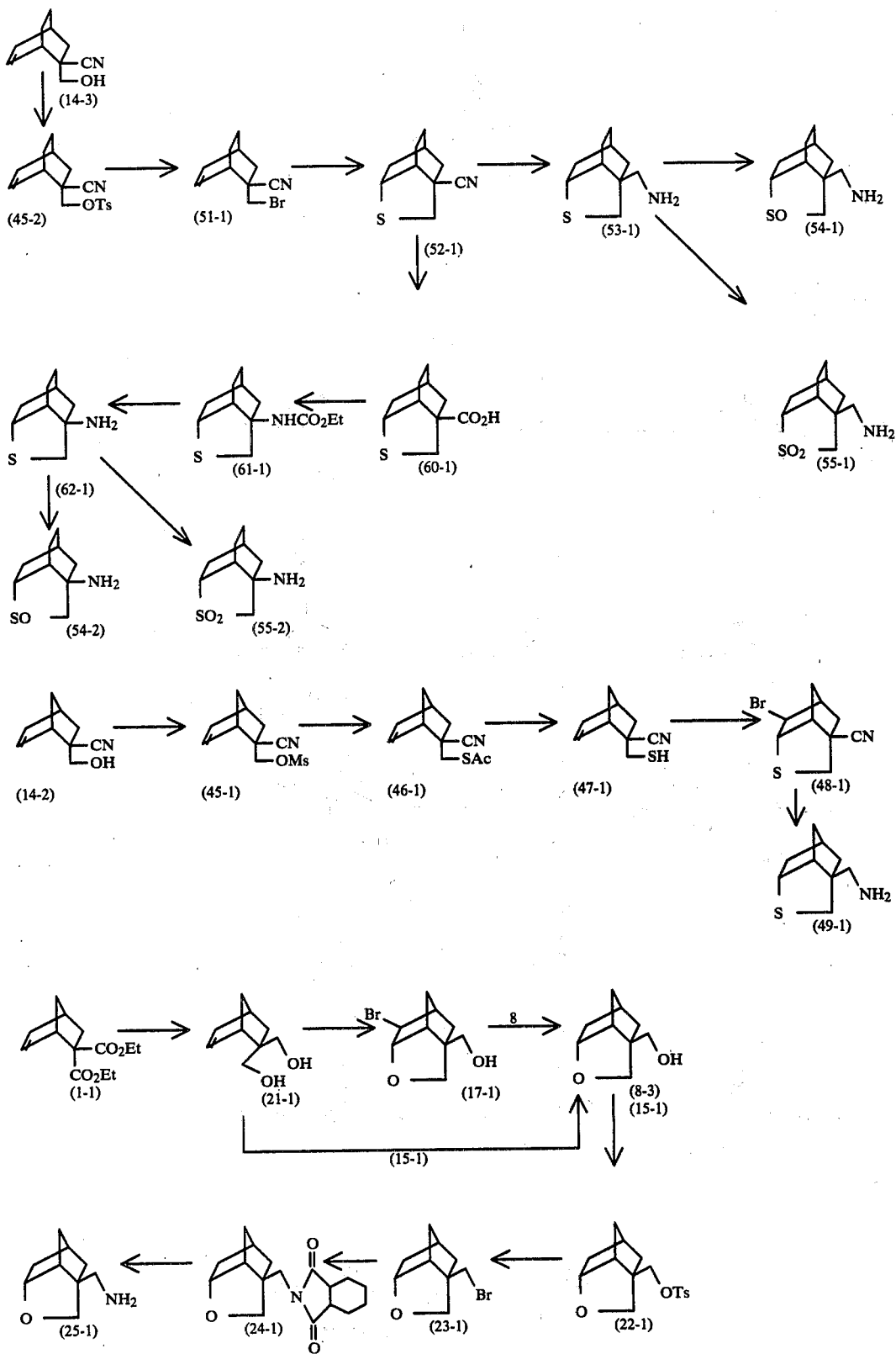

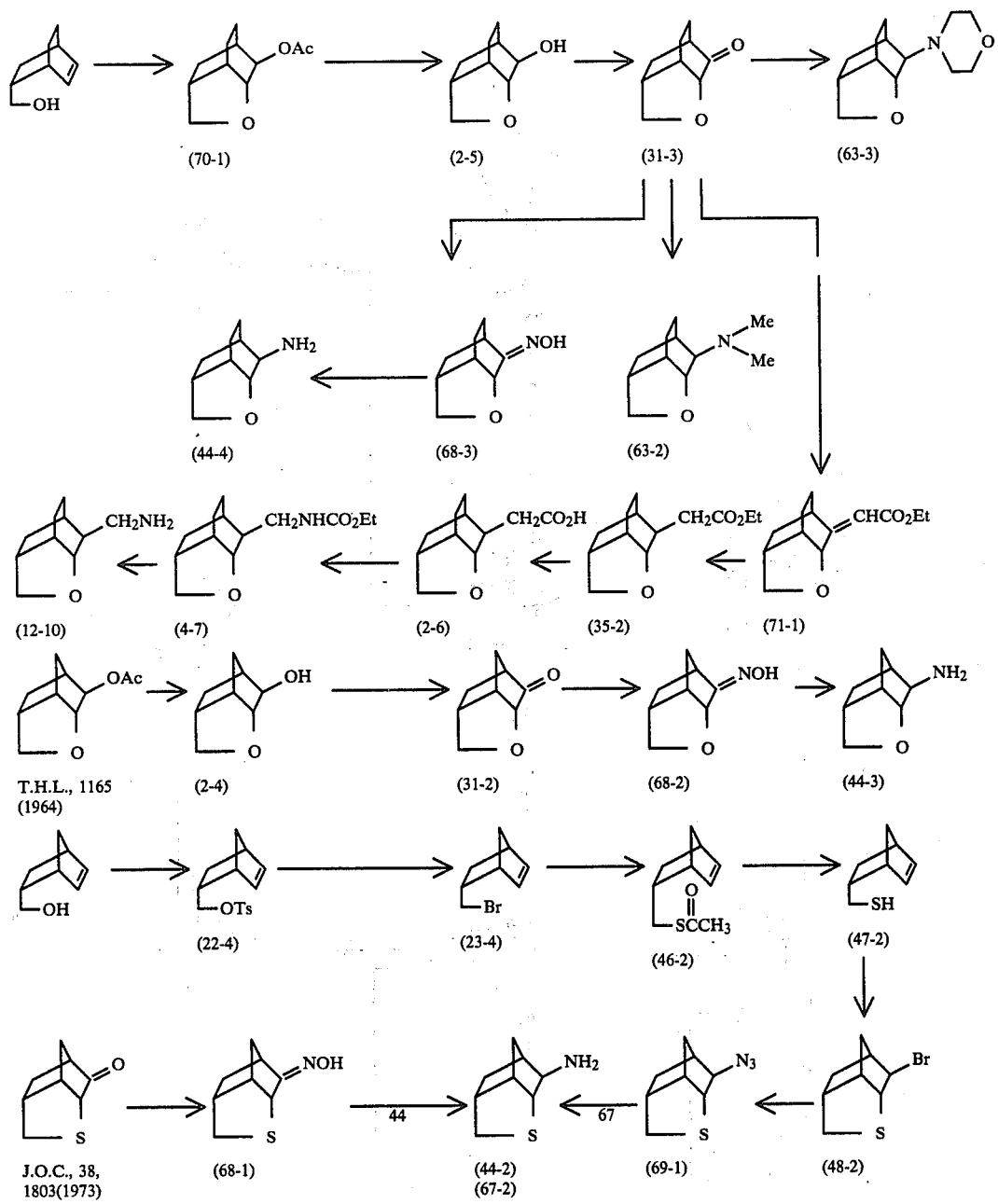

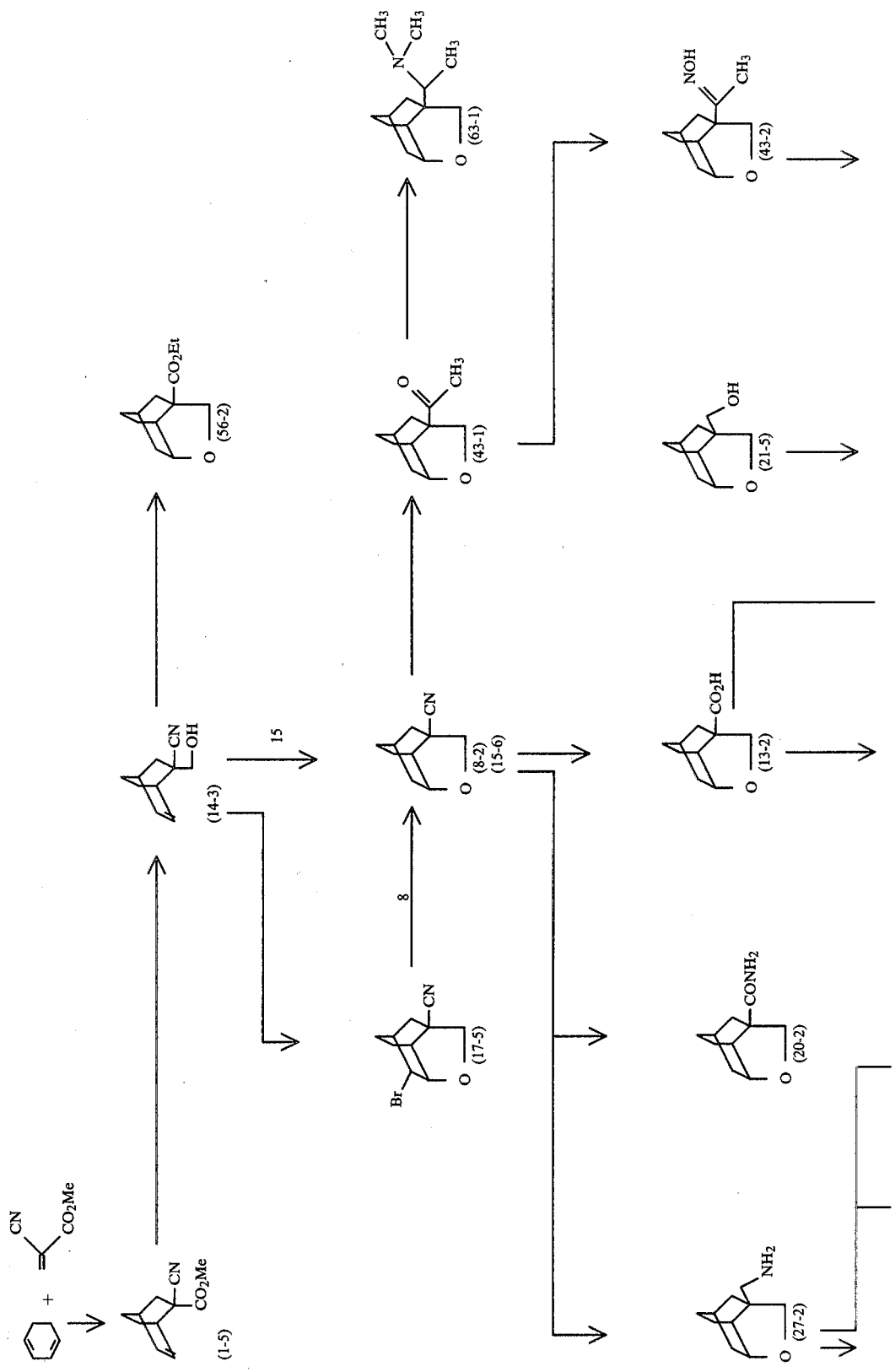

-continued
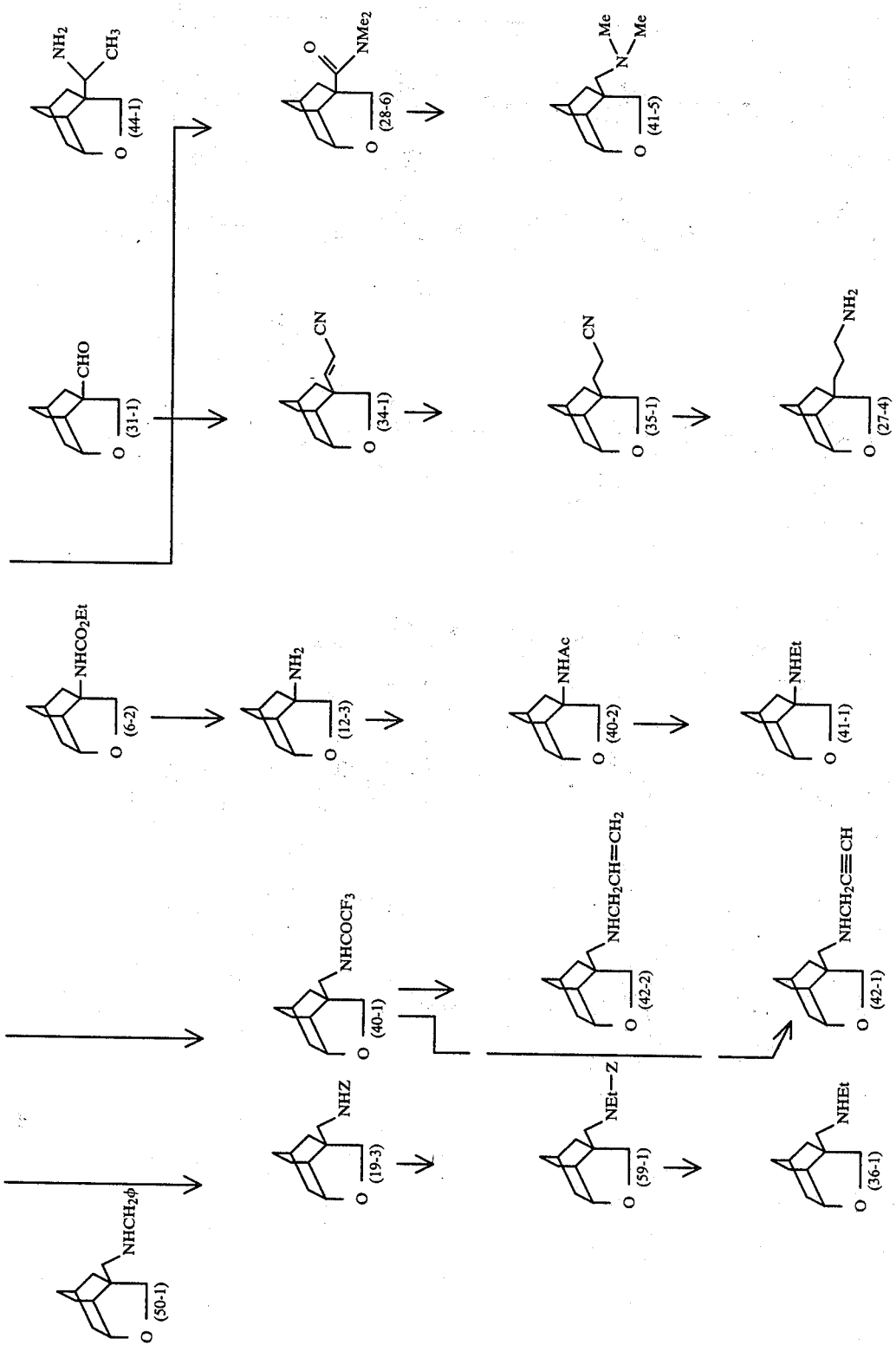

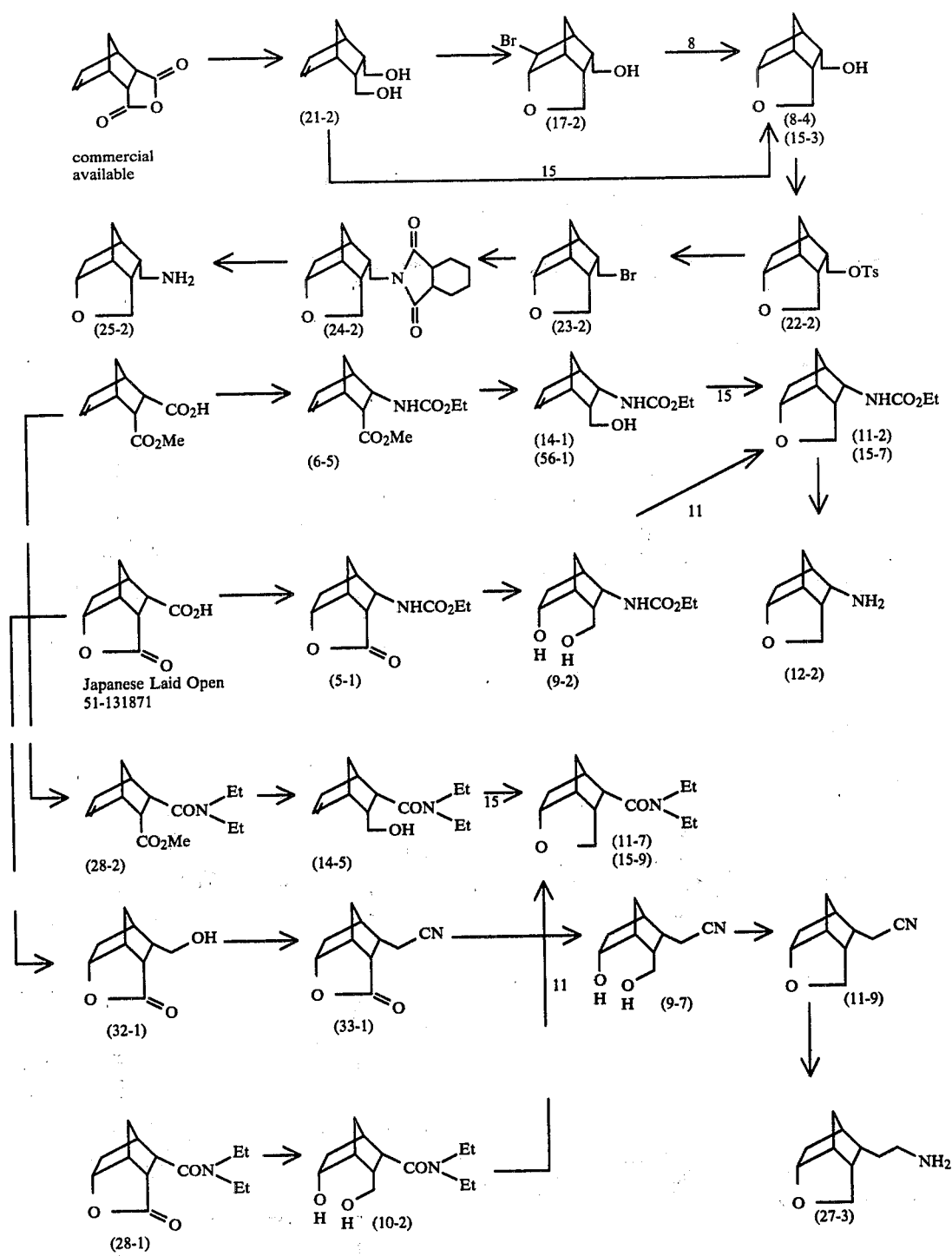

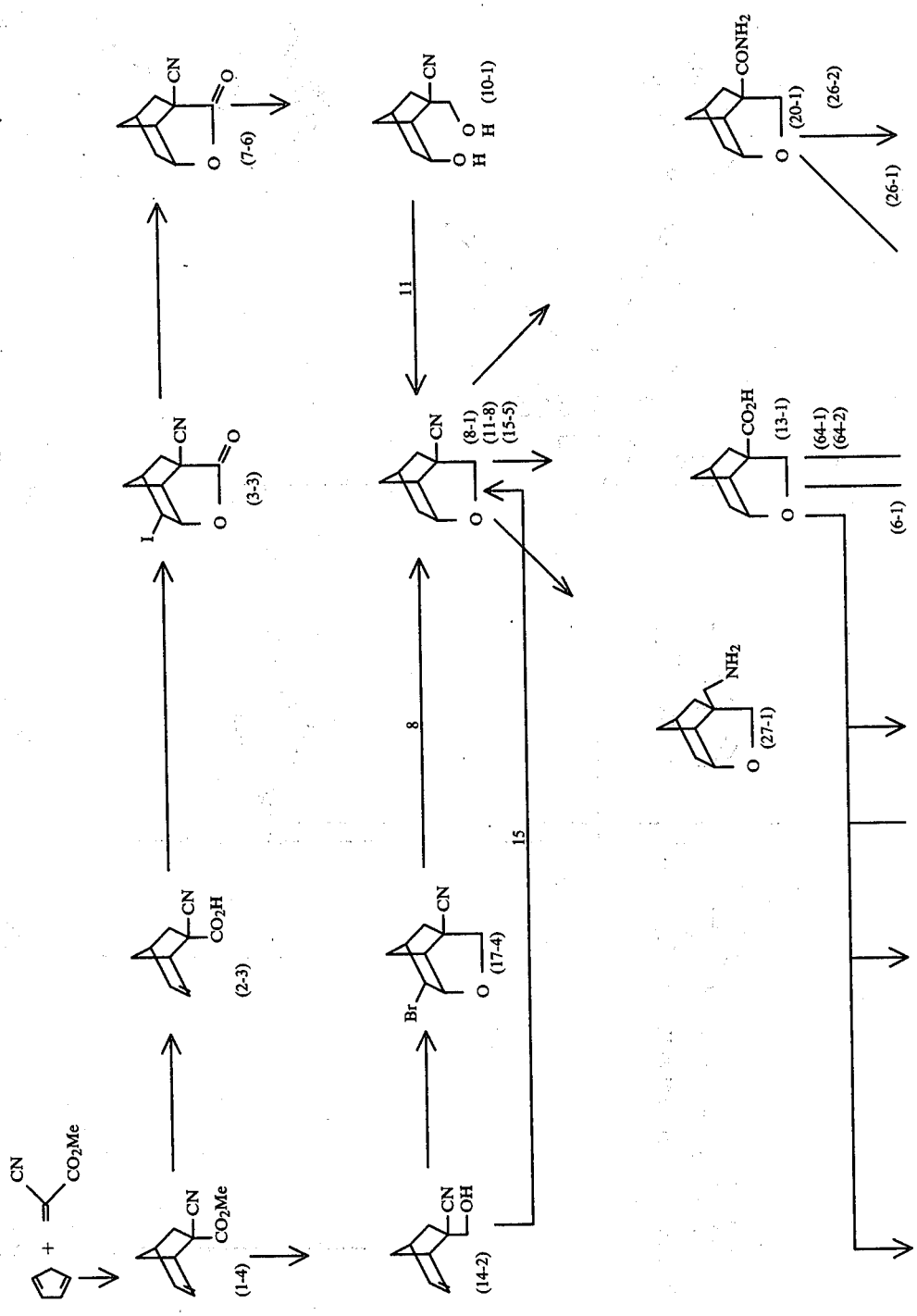

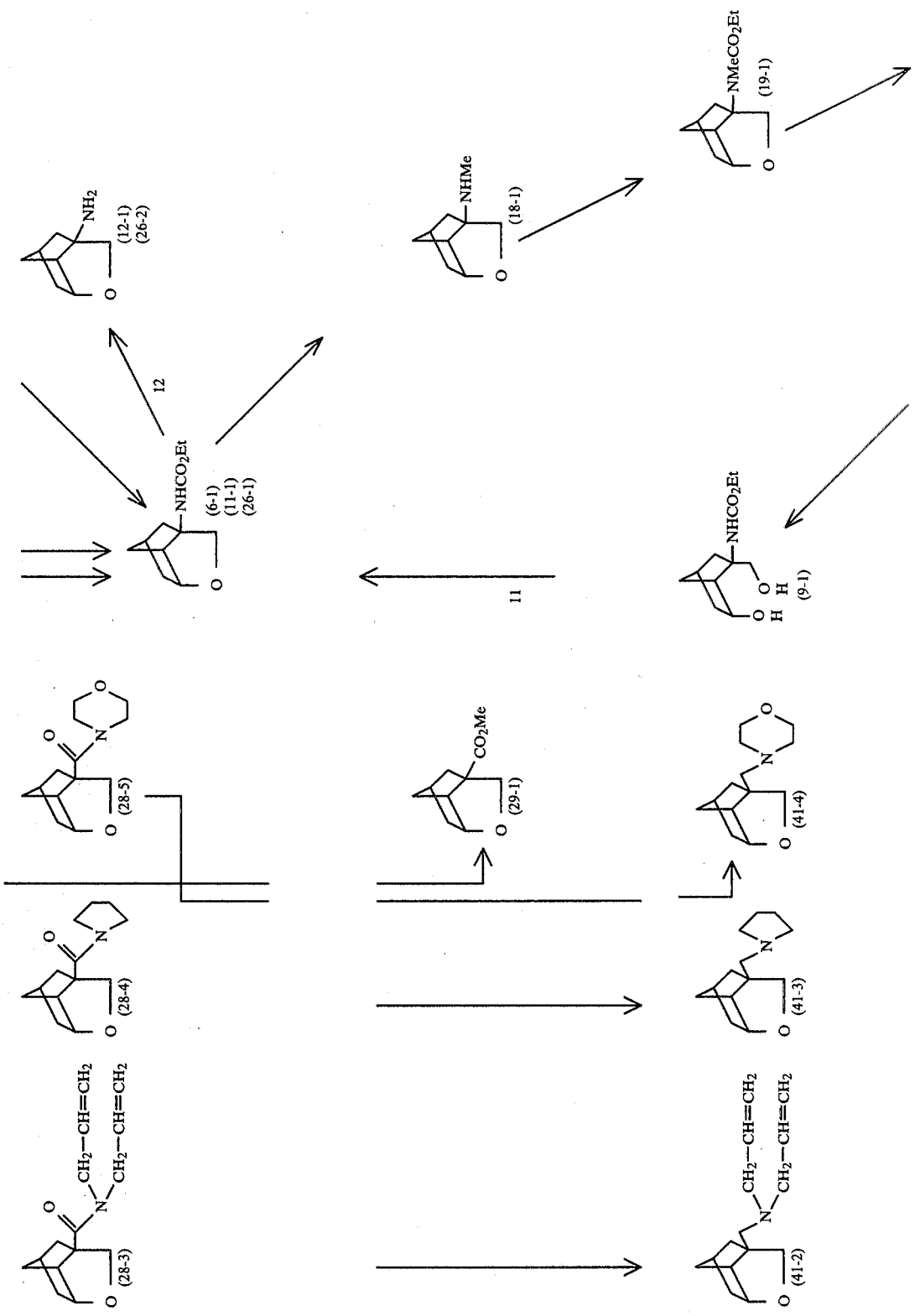

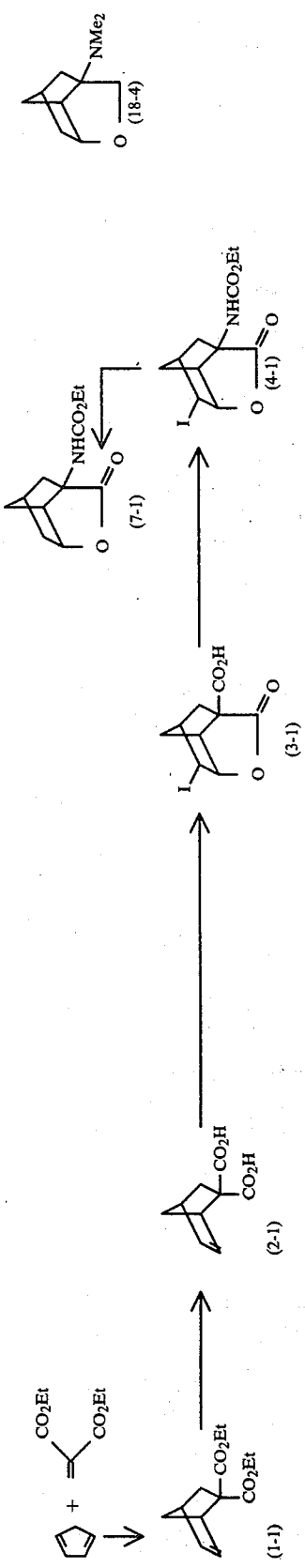

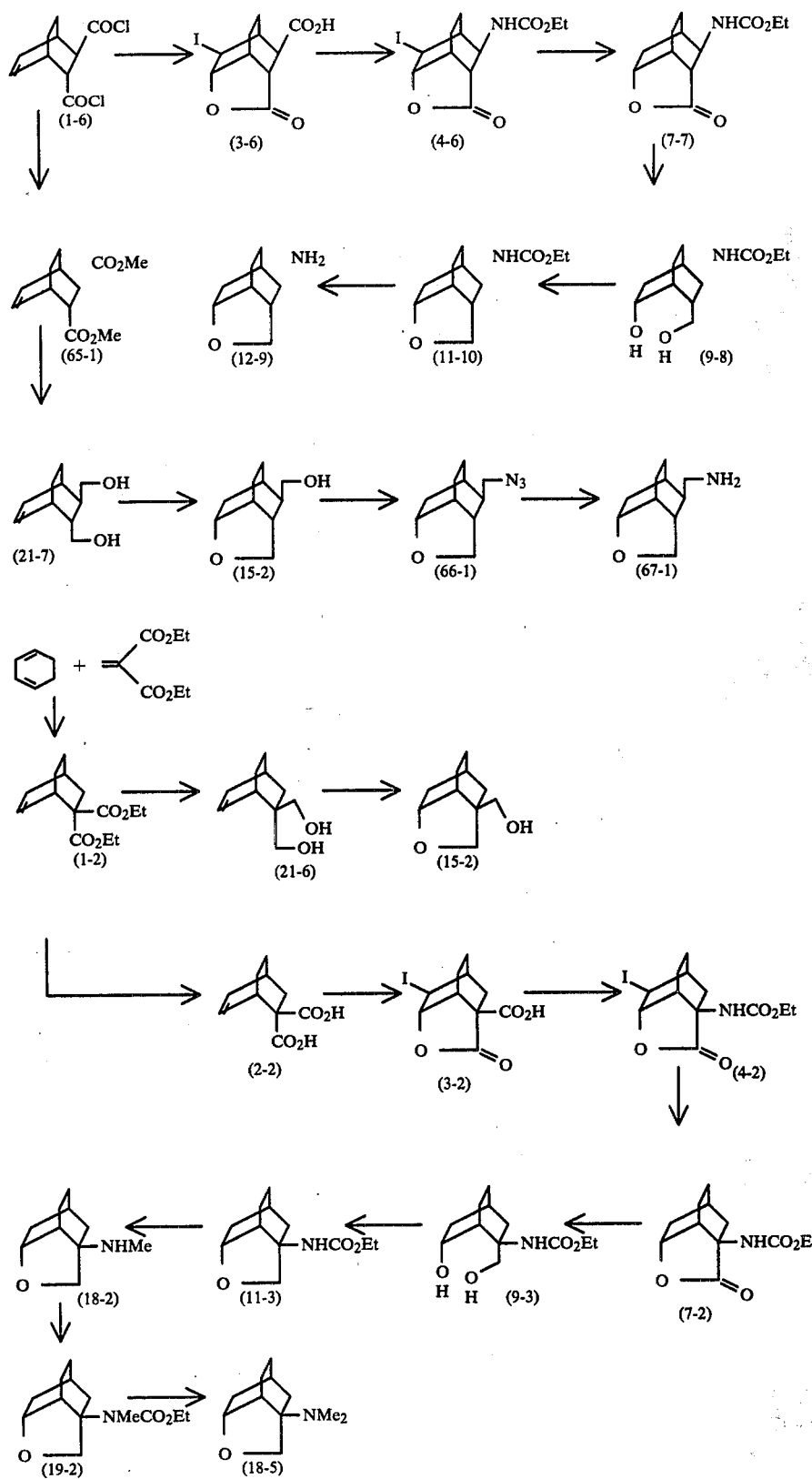

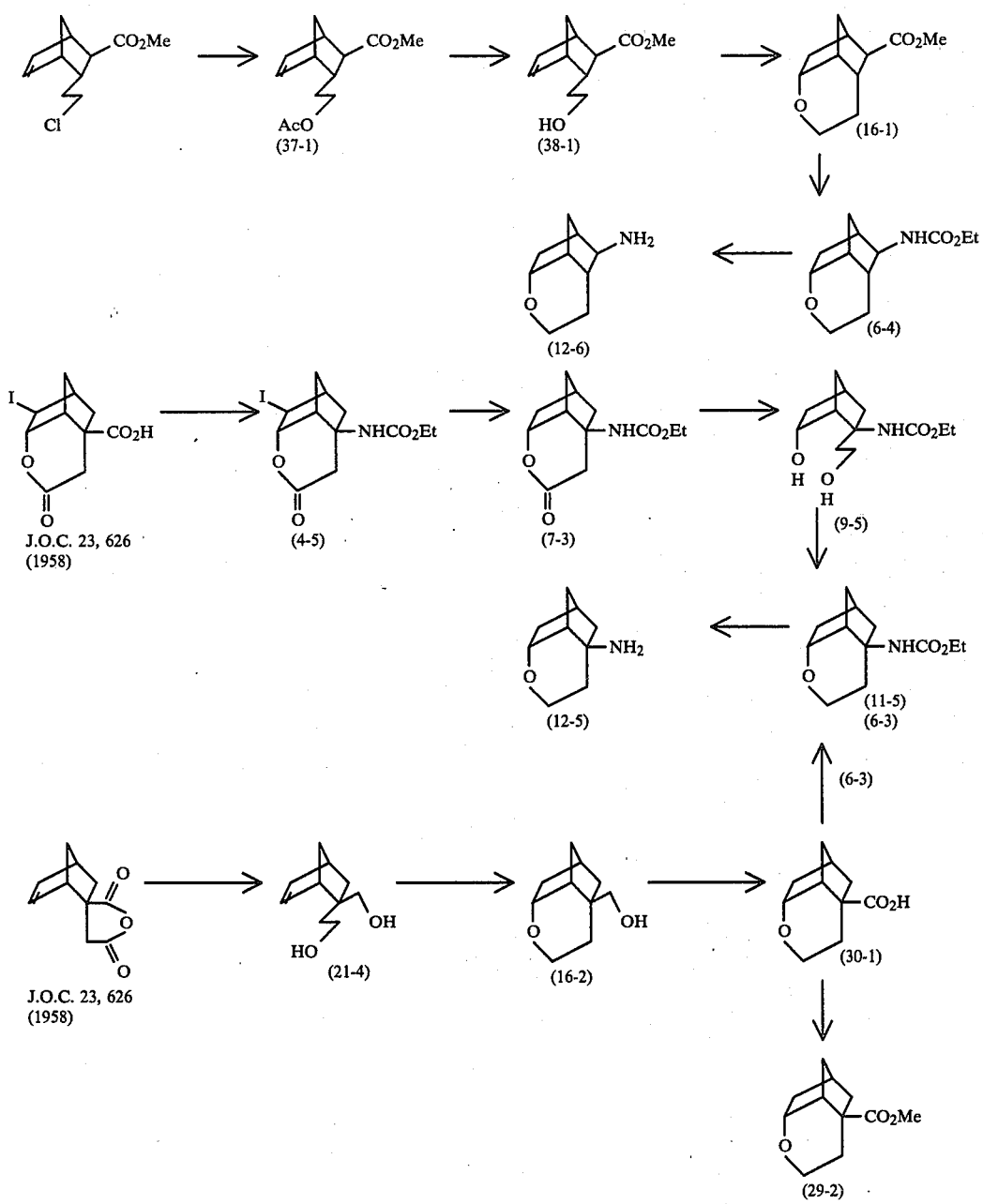

EXAMPLE 1

Into a solution of diethyl methylene malonate (21.5 g) in dry benzene (200 ml), cyclopentadiene (9.8 g) was added at an ambient temperature. The reaction solution was stirred at the same temperature for 1 hour. After evaporation of the solvent, distillation of the residue gave 11.8 g of 2,2-bisethoxycarbonyl-5-norbornene (Compound No. 1-1). B.P., 85°–90° C./0.2 mmHg. IR$\nu_{max}^{film}$ (cm$^{-1}$): 2970, 1740, 1460.

According to the same procedure, using diethylmethylene malonate (47.3 g) and 1,3-cyclohexadiene (20 g) but benzene refluxed, there was obtained oily 2,2-bisethoxycarbonyl-bicyclo[2,2,2]oct-5-ene (Compound No. 1-2) (65.0 g). IR$\nu_{max}^{film}$ (cm$^{-1}$): 2970, 1740, 1450.

According to the same procedure, using itaconic acid anhydride (8.3 g) and 1,3-cyclohexadiene (10 g) but benzene refluxed, there was obtained as a solid exo-2-carboxy-endo-2-carboxymethylanhydride-bicyclo[2,2,2]oct-5-ene (Compound No. 1-3) (10.5 g). M.P., 70°–75° C. (recrystallization from hexane). IR$\nu_{max}^{KBr}$ (cm$^{-1}$): 2950, 1850, 1780, 1240, 1030.

According to the same procedure, using methyl-α-cyanoacrylate (35 g) and cyclopentadiene (20 g), there was obtained as an oil exo-2-cyano-endo-2-methoxycarbonyl-5-norbornene (Compound No. 1-4) (56 g). (This substance contained 10% isomer of exo-2-methoxycarbonyl-endo-2-cyano-5-norbornene.) IR$\nu_{max}^{film}$ (cm$^{-1}$): 2960, 2230, 1750, 1320, 1250.

According to the same procedure, using methyl-α-cyanoacrylate (20 g) and 1,3-cyclohexadiene (14.4 g), there was obtained as an oil exo-2-cyano-endo-2-methoxycarbonylbicyclo[2,2,2]oct-5-ene (Compound No. 1-5) (33 g). (This material contained 20% isomer of exo-2-methoxycarbonyl-endo-2-cyano-bicyclo[2,2,2]oct-5-ene.) IR$\nu_{max}^{film}$ (cm$^{-1}$): 2950, 2250, 1750, 1440, 1270, 1260, 1080.

According to the same procedure, using fumaryl chloride (35.5 g) and 1,3-cyclohexadiene (20 g), there was obtained as an oil endo-2-chlorocarbonyl-exo-3-chlorocarbonyl-bicyclo[2,2,2]oct-5-ene (Compound No. 1-6) (28 g). IR$\nu_{max}^{film}$ (cm$^{-1}$): 2950, 1780, 1440, 1270.

EXAMPLE 2

A mixture of methanol (12 ml), 10% aqueous sodium hydroxide (12 ml), tetrahydrofuran (12 ml) and 2,2-bisethoxycarbonyl-5-norbornene (2.38 g) was stirred at room temperature for 24 hours and concentrated under reduced pressure. The residue was diluted with water, made acidic with 10% hydrochloric acid (HCl) solution and extracted with ether. The extract was washed with water and dried. Removal of the solvent gave as an oil 2,2-dicarboxy-5-norbornene (Compound No. 2-1) (1.63 g). IR$\nu_{max}^{film}$ (cm$^{-1}$): 2990, 1710, 1340.

According to the same procedure, there were obtained the following compounds, for which the starting materials were obtained by the method of Example 1:

2,2-Dicarboxy-bicyclo[2,2,2]oct-5-ene (Compound No. 2-2), oily substance. IR$\nu_{max}^{film}$ (cm$^{-1}$): 2990, 1710, 1350;

Exo-2-cyano-endo-2-carboxy-5-norbornene, oily substance (Compound No. 2-3). IR$\nu_{max}^{film}$ (cm$^{-1}$): 2980, 2600, 2240, 1720.

According to the same procedure, there was obtained the following compound, for which the starting material was obtained by the method of R. M. Moriarty THL., 1165 (1964):

Exo-2-hydroxy-4-oxa-brenedane (Compound No. 2-4), oily substance. IR$\nu_{max}^{film}$ (cm$^{-1}$): 3300, 2950, 2850, 1240, 1080.

According to the same procedure, there was obtained the following compound, for which the starting material was obtained by the method of Example 70-1:

Exo-2-hydroxy-4-oxa-isotwistane (Compound No. 2-5), oily substance. IR$\nu_{max}^{film}$ (cm$^{-1}$): 3500, 3000-2800, 1460, 1420, 1380, 1240, 1190, 1080.

According to the same procedure, there was obtained the following compound for which the starting material was obtained by the method of Example 35-2:

2-Carboxymethyl-4-oxa-isotwistane (Compound No. 2-6), solid substance. IR$\nu_{max}^{film}$ (cm$^{-1}$): 2930, 2870, 2650, 1700, 1410, 1240.

EXAMPLE 3

2,2-Dicarboxy-5-norbornene (1.63 g) was dissolved with warming in a solution of 0.5 N sodium bicarbonate (60 ml). After cooling to room temperature, a solution of iodine (I$_2$, 2.54 g) and potassium iodide (KI, 5.08 g) in 30 ml of water was added, and the mixture was kept in the dark for 24 hours. It was then filtered, the filtrate was acidified with dilute HCl and treated with sodium thiosulfate until iodine color disappeared. It was extracted with ether, and the extract was washed with saturated sodium chloride (NaCl) solution and dried.

Removal of the solvent gave a solid which was recrystallized from benzene to yield 1.8 g of exo-9-iodo-5-oxa-4-oxo-3-carboxy-brendane (Compound No. 3-1), M.P., 171°-172° C. IR$\nu_{max}^{KBr}$(cm$^{-1}$): 2950, 1780, 1740, 1480.

According to the same procedure, there were obtained the following compounds, for which the starting materials were obtained by the method of Example 2:

Exo-10-iodo-5-oxa-4-oxo-3-carboxy-isotwistane (Compound No. 3-2), solid substance, M.P., 198°-200° C. (recrystallization from benzene). IR$\nu_{max}^{KBr}$ (cm$^{-1}$): 2950, 1780, 1710, 1380;

Exo-9-iodo-5-oxa-4-oxo-3-cyano-brenedane (Compound No. 3-3), solid substance, M.P., 192°-193.5° C. (recrystallization from benzene). IR$\nu_{max}^{Nujol}$ (cm$^{-1}$): 2250, 1780, 1100.

According to the same procedure, there was obtained the following compound, for which the starting material was obtained by the method of Example 1:

Exo-11-iodo-6-oxa-5-oxo-3-carboxy-homoisotwistane (Compound No. 3-4), solid substance, M.P., 205°-210° C. recrystallization from ether). IR$\nu_{max}^{film}$ (cm$^{-1}$): 1720, 1340, 1300.

According to the same procedure, there was obtained the following compound:

Exo-10-iodo-5-oxa-4-oxo-endo-2-carboxy-isotwistane (Compound No. 3-5), solid substance, M.P., 191°-193° C. IR$\nu_{max}^{Nujol}$ (cm$^{-1}$): 1790, 1780, 1730, 1710.

According to the same procedure, there was obtained the following compound, for which the starting material was obtained by the method of Example 1-6:

Exo-10-iodo-5-oxa-4-oxo-exo-2-carboxy-isotwistane (Compound No. 3-6), solid substance, M.P., 182°-185° C. (recrystallization from ethyl acetate). IR$\nu_{max}^{Nujol}$ (cm$^{-1}$): 2000, 1990, 1710, 1690, 980.

EXAMPLE 4

A mixture of exo-9-iodo-5-oxa-4-oxo-3-carboxybrendane (1.0 g) and thionyl chloride (20 ml) was refluxed for 3 hours. The reaction mixture was evaporated to dryness, benzene (20 ml) was added thereto and evaporation was effected to remove thionyl chloride. Into a solution of thus obtained acid chloride in acetone (20 ml) was added sodium azide (NaN$_3$, 0.232 g) under cooling. The reaction solution was stirred for 24 hours at an ambient temperature. After evaporation of the solvent, the residue was dissolved in dry ethanol (50 ml) and refluxed for 2 hours. After evaporation of the solvent, the residue was extracted with chloroform. The extract was washed with water and dried. Evaporation of the solvent gave a solid, which was recrystallized from benzene to yield 0.85 g of exo-9-iodo-5-oxa-4-oxo-3-ethoxycarbonylamino-brendane (Compound No. 4-1), M.P., 165°-167° C. IR$\nu_{max}^{KBr}$(cm$^{-1}$): 3320, 2990, 1800, 1690.

According to the same procedure, there were obtained the following compounds, for which the starting materials were obtained by the method of Example 3:

Exo-10-iodo-5-oxa-4-oxo-ethoxycarbonylaminoisotwistane (Compound No. 4-2), solid substance. IR$\nu_{max}^{Nujol}$ (cm$^{-1}$): 3350, 1800, 1730-1700, 1540-1510;

Exo-10-iodo-5-oxa-4-oxo-endo-2-ethoxycarbonylamino-isotwistane (Compound No. 4-3), solid substance, M.P., 158°-159° C. (recrystallization from ethyl acetate-n-hexane). IR$\nu_{max}^{Nujol}$ (cm$^{-1}$): 3300, 1800, 1690, 1550; Exo-11-iodo-6-oxa-5-oxo-3-ethoxycarbonylaminohomoisotwistane (Compound No. 4-4) (18.4 g), M.P., 139°-140° C. IR$\nu_{max}^{Nujol}$ (cm$^{-1}$): 3300, 1720, 1530.

According to the same procedure, there was obtained the following compound:

Exo-10-iodo-6-oxa-5-oxo-3-ethoxycarbonylaminohomobrendane (Compound No. 4-5), solid substance, M.P., 112°-114.5° C. IR$\nu_{max}^{Nujol}$ (cm$^{-1}$): 3350, 1730-1700, 1450.

According to the same procedure, there was obtained the following compound, for which the starting material was obtained by the method of Example 3-6:

Exo-10-iodo-5-oxa-4-oxo-exo-2-ethoxycarbonylamino-isotwistane (Compound No. 4-6), solid substance, M.P., 115°-117° C. IR$\nu_{max}^{Nujol}$ (cm$^{-1}$): 3350, 1790, 1680, 1450, 980.

According to the same procedure, there was obtained the following compound, for which the starting material was obtained by the method of Example 2-6:

2-Ethoxycarbonylaminomethyl-4-oxa-isotwistane (Compound No. 4-7), oily substance. IR$\nu_{max}^{film}$ (cm$^{-1}$): 3320, 2930, 2870, 1700, 1540, 1260, 1080, 1040.

EXAMPLE 5

A solution of 5-oxa-4-oxo-endo-2-carboxy-brendane (10 g), N,N-dimethylformamide (2 drops) and thionyl chloride (83 ml) in dry dichloromethane was refluxed for 3 hours. The reaction mixture was evaporated to dryness, benzene (20 ml) was added thereto, and evaporation was effected to remove thionyl chloride. Into a solution of thus obtained acid chloride in acetone (40 ml), NaN$_3$ (3.93 g) was added under cooling. The reaction mixture was stirred for 24 hours at an ambient temperature. After evaporation of the solvent, the residue was dissolved in dry ethanol (100 ml) and refluxed for 2 hours. After evaporation of the solvent, the residue was extracted with chloroform. The extract was washed with water and dried. Evaporation of the solvent gave a solid, which was recrystallized from benzene to yield 6.9 g of 5-oxa-4-oxo-endo-2-ethoxycarbonylamino-brendane (Compound No. 5-1), M.P., 119°-120° C. IR$\nu_{max}^{Nujol}$ (cm$^{-1}$): 3250, 3140, 1780, 1720.

EXAMPLE 6

Into a solution of 5-oxa-3-carboxy-brendane (4.0 g), triethylamine (3.1 g) in dry acetone (50 ml), ethylchlorocarbonate (3.1 g) was added with stirring at −20° C. for 1 hour. Into the reaction mixture, sodium azide (2.02 g) in water (10 ml) was added at −20° C. for 1 hour. After warming to room temperature, the reaction mixture was extracted with benzene and dried. After evaporation of the solvent, the residue was dissolved in dry ethanol (150 ml) and refluxed for 3 hours. After removal of the solvent, chromatography on silica gel using chloroform for elution yielded 5-oxa-3-ethoxycarbonylamino-brendane (Compound No. 6-1) (4.3 g) as an oil. IR$\nu_{max}^{film}$ (cm$^{-1}$): 3300, 2950, 1700, 1530.

According to the same procedure, there was obtained the following compound, for which the starting material was obtained by the method of Example 13-2:

5-Oxa-3-ethoxycarbonylamino-isotwistane (Compound No. 6-2), oily substance. IR$\nu_{max}^{film}$ (cm$^{-1}$): 3300, 2950, 1700, 1530.

According to the same procedure, there was obtained the following compound, for which the starting material was obtained by the method of Example 30-1:

6-Oxa-3-ethoxycarbonylamino-homobrendane (Compound No. 6-3), oily substance. IR$\nu_{max}^{film}$ (cm$^{-1}$): 3330, 2950, 2870, 1700.

According to the same procedure, there were obtained the following compounds, for which the starting materials were obtained by the method of Example 16-1:

6-Oxa-exo-2-ethoxycarbonylamino-homobrendane (Compound No. 6-4), oily substance. IR$\nu_{max}^{film}$ (cm$^{-1}$): 3340, 2960, 1720, 1540;

Endo-2-methoxycarbonyl-endo-3-ethoxycarbonylamino-5-norbornene (Compound No. 6-5), oily substance. IR$\nu_{max}^{film}$ (cm$^{-1}$): 3400, 3000, 1720, 1520;

Endo-2-methoxycarbonyl-endo-3-ethoxycarbonylaminobicyclo[2,2,2]oct-5-ene (Compound No. 6—6), solid substance, M.P., 63°-64° C. IR$\nu_{max}^{Nujol}$ (cm$^{-1}$): 3370, 1730, 1710, 1520;

Endo-8-ethoxycarbonylamino-endo-9-ethoxycarbonyltricyclo[3,2,2,0$^{2,4}$]non-6-ene (Compound No. 6-7), oily substance. IR$\nu_{max}^{Nujol}$ (cm$^{-1}$): 3430, 1730, 1510, 1170.

EXAMPLE 7

Into a solution of exo-9-iodo-5-oxa-4-oxo-3-ethoxycarbonylamino-brendane (4.5 g) and azobisisobutyronitrile (50 mg) in dry tetrahydrofuran (THF, 100 ml) was added tri-n-butyltin hydride (4.5 g) in dry ether (50 ml). The reaction mixture was stirred for 2 hours at room temperature. After evaporation of the solvent, the residue was discharged into n-hexane (100 ml) to precipitate 5-oxa-4-oxo-3-ethoxycarbonylamino-brendane (Compound No. 7-1) (2.8 g) as a solid. M.P., 91°-92° C. (recrystallization from benzene-n-hexane). IR$\nu_{max}^{Nujol}$ (cm$^{-1}$): 3320, 1790, 1690, 1380.

According to the same procedure, there were obtained the following compounds, for which the starting materials were obtained by the method of Example 4:

5-Oxa-4-oxo-3-ethoxycarbonylamino-isotwistane (Compound No. 7-2), solid substance, M.P., 157°-159° C. (recrystallization from isopropyl ether). IR$\nu_{max}^{Nujol}$ (cm$^{-1}$): 3330, 1780, 1710, 1540;

6-Oxa-5-oxo-3-ethoxycarbonylamino-homobrendane (Compound No. 7-3), solid substance, M.P., 90.5°-92.0° C. (recrystallization from benzene-n-hexane). IR$\nu_{max}^{KBr}$ (cm$^{-1}$): 3330, 1730-1700, 1520, 1450;

6-Oxa-5-oxo-3-ethoxycarbonylamino-homoisotwistane (Compound No. 7-4), solid substance, M.P., 118°-120° C. (recrystallization from benzene-n-hexane). IR$\nu_{max}^{Nujol}$ (cm$^{-1}$): 3300, 1730-1700;

5-Oxa-4-oxo-endo-2-ethoxycarbonylamino-isotwistane (Compound No. 7-5), solid substance, M.P., 157°-159° C. (recrystallization from isopropyl ether). IR$\nu_{max}^{Nujol}$ (cm$^{-1}$): 3300, 1780, 1700, 1540.

According to the same procedure, there was obtained the following compound, for which the starting material was obtained by the method of Example 3—3:

5-Oxa-4-oxo-3-cyano-brendane (Compound No. 7-6), solid substance, M.P., 150°-151° C. (recrystallization from benzene-cyclohexane). IR$\nu_{max}^{KBr}$ (cm$^{-1}$): 2950, 2250, 1780, 1000.

According to the same procedure, there was obtained the following compound, for which the starting material was obtained by the method of Example 4-6:

5-Oxa-4-oxo-exo-2-ethoxycarbonylamino-isotwistane (Compound No. 7—7), solid substance, M.P., 156°-159° C. (recrystallization from diisopropyl ether). IR$\nu_{max}^{Nujol}$ (cm$^{-1}$): 3400, 1780, 1680, 1270, 970.

EXAMPLE 8

Into a solution of exo-9-bromo-5-oxa-3-cyanobrendane (15.0 g) and azobisisobutyronitrile (100 mg) in dry tetrahydrofuran (300 ml) was added tri-n-butyltin hydride (11.5 g) in dry ether (100 ml). The reaction mixture was stirred for 5 hours at room temperature. Evaporation of the solvent gave an oily substance, which was chromatographed on silica gel. 5-Oxa-3-cyano-brendane (Compound No. 8-1) (10 g) as an oil was eluted with benzene. IR$\nu_{max}^{film}$ (cm$^{-1}$): 2950, 2870, 2240, 1450, 1100.

According to the same procedure, there were obtained the following compounds, for which the starting materials were obtained by the method of Example 17:

5-Oxa-3-cyano-isotwistane (Compound No. 8-2), solid substance, M.P., 105° C. IR$\nu_{max}^{Nujol}$(cm$^{-1}$): 2250, 1480, 1440, 1340, 1080, 1040;

5-Oxa-3-hydroxymethyl-brendane (Compound No. 8-3), oily substance. IR$\nu_{max}^{film}$ (cm$^{-1}$): 3600-3100, 1450, 1340;

5-Oxa-endo-2-hydroxymethyl-brendane (Compound No. 8-4), oily substance. IR$\nu_{max}^{film}$ (cm$^{-1}$): 3400, 1440, 1360;

5-Oxa-endo-2-hydroxymethyl-isotwistane (Compound No. 8-5), oily substance. IR$\nu_{max}^{film}$ (cm$^{-1}$): 3500, 1100, 1080.

EXAMPLE 9

An ethanol solution containing 5-oxa-4-oxo-3-ethoxycarbonylamino-brendane (1.0 g) was added to calcium borohydride prepared from dry calcium chloride (1.46 g) and sodium borohydride (0.671 g) in dry ethanol, while stirring and cooling at 2°-5° C. Stirring was continued at 5° C. for 5 hours. After consumption of excess calcium borohydride by addition of a saturated NH$_4$Cl solution, the mixture was concentrated to give a syrupy residue, which was extracted with chloroform. The extract was washed with saturated NaCl, dried and concentrated to give as an oily substance endo-5-hydroxy-endo-3-hydroxymethyl-exo-3-ethoxycarbonylamino-norbornane (Compound No. 9-1) (0.9 g). IR$\nu_{max}^{film}$ (cm$^{-1}$): 3400, 3350, 1680, 1540.

According to the same procedure, there were obtained the following compounds:

Endo-5-hydroxy-endo-3-hydroxymethyl-endo-2-ethoxycarbonylamino-norbornane (Compound No. 9-2), solid substance. IR$\nu_{max}^{Nujol}$ (cm$^{-1}$): 3430, 3350, 3250, 1700, 1520;

Endo-5-hydroxy-endo-3-hydroxymethyl-exo-3-ethoxy carbonylamino-bicyclo[2,2,2]octane (Compound No. 9-3), oily substance. IR$\nu_{max}^{film}$ (cm$^{-1}$): 3600-3100, 1700, 1520;

Endo-5-hydroxy-endo-3-hydroxymethyl-endo-2-ethoxycarbonylamino-bicyclo[2,2,2]octane (Compound No. 9-4), solid substance. IR$\nu_{max}^{Nujol}$ (cm$^{-1}$): 3600, 3100, 1720, 1700, 1520;

Endo-5-hydroxy-endo-3-β-hydroxyethyl-exo-3-ethoxycarbonylamino-norbornane (Compound No. 9-5), solid substance. IR$\nu_{max}^{Nujol}$ (cm$^{-1}$): 3330, 1700, 1470, 1070;

Endo-5-hydroxy-endo-3-β-hydroxyethyl-exo-3-ethoxycarbonylamino-bicyclo[2,2,2]octane (Compound No. 9-6), solid substance. IR$\nu_{max}^{Nujol}$ (cm$^{-1}$): 3350, 1700, 1470;

Endo-5-hydroxy-endo-3-hydroxymethyl-endo-2-cyanomethyl-norbornane (Compound No. 9-7), oily substance. IR$\nu_{max}^{film}$ (cm$^{-1}$): 3350, 2250, 1460, 1430, 1140, 1120, 1060.

According to the same procedure, there was obtained the following compound, for which the starting material was obtained by the method of Example 7—7:

Endo-5-hydroxy-endo-3-hydroxymethyl-exo-2-ethoxycarbonylamino-bicyclo[2,2,2]octane (Compound No. 9-8), oily substance. IR$\nu_{max}^{film}$ (cm$^{-1}$): 3300, 2930, 1700, 1520, 1040.

EXAMPLE 10

An ethanol solution (300 ml) containing 5-oxa-4-oxo-3-cyano-brendane (9.8 g) was added to calcium borohydride prepared from dry calcium chloride (20 g) and sodium borohydride (9.12 g) in dry ethanol, while stirring and cooling at 2°-5° C. Stirring was continued at room temperature for 5 hours. After consumption of excess calcium borohydride by addition of 10% HCl solution, the mixture was concentrated to give a syrupy residue. The resulting oily layer was extracted with chloroform. The extract was washed with saturated NaCl, dried and concentrated to give as an oily substance endo-5-hydroxy-endo-3-hydroxymethyl-exo-3-cyano-norbornane (Compound No. 10-1) (9.5 g), M.P., 123°-127° C. IR$\nu_{max}^{Nujol}$ (cm$^{-1}$): 3300, 2230, 1110.

According to the same procedure, there was obtained the following compound:

Endo-5-hydroxy-endo-3-hydroxymethyl-endo-2-N,N-diethylcarbamoyl-norbornane (Compound No. 10-2), oily substance. IR$\nu_{max}^{film}$ (cm$^{-1}$): 3300, 2960, 1620, 1460.

EXAMPLE 11

Into a mixture of dry benzene (10 ml), pyridine (5 ml) and endo-5-hydroxy-endo-3-hydroxymethyl-exo-3-ethoxycarbonylamino-norbornane (0.9 g) was added p-toluenesulfonyl chloride (0.997 g) at 0°-5° C. for 1 hour, and the reaction mixture was stirred at room temperature overnight. The reaction mixture was discharged into a mixture of chloroform (100 ml) and 10% HCl (50 ml), and the organic layer was separated, washed, dried and concentrated under reduced pressure. Chromatography on silica gel using chloroform for elution yielded as an oily substance 5-oxa-3-ethoxycarbonylamino-brendane (Compound No. 11-1) (0.34 g). IR$\nu_{max}^{film}$ (cm$^{-1}$): 3300, 2950, 1700, 1530.

According to the same procedure, there were obtained the following compounds, for which the starting materials were obtained by the method of Examples 9 and 10:

5-Oxa-endo-2-ethoxycarbonylamino-brendane (Compound No. 11-2), oily substance. IR$\nu_{max}^{film}$ (cm$^{-1}$): 3300, 1700, 1540, 1200;

5-Oxa-3-ethoxycarbonylamino-isotwistane (Compound No. 11-3), solid substance, M.P., 73°-74.5° C. IR$\nu_{max}^{film}$ (cm$^{-1}$): 3300, 1700, 1550, 1240;

5-Oxa-endo-2-ethoxycarbonylamino-isotwistane (Compound No. 11-4), solid substance, M.P., 83°-84° C. IR$\nu_{max}^{film}$ (cm$^{-1}$): 3320, 1720, 1540, 1260;

6-Oxa-3-ethoxycarbonylamino-homobrendane (Compound No. 11-5), oily substance. IR$\nu_{max}^{film}$ (cm$^{-1}$): 3330, 2950, 2870, 1700;

6-Oxa-3-ethoxycarbonylamino-homoisotwistane (Compound No. 11-6), oily substance. IR$\nu_{max}^{film}$ (cm$^{-1}$): 3350, 1700, 1540, 1260;

5-Oxa-endo-2-N,N-diethylcarbamoyl-brendane (Compound No. 11-7), solid substance, M.P., 57°-58.5° C. IR$\nu_{max}^{KBr}$ (cm$^{-1}$): 2850, 1640, 1485;

5-Oxa-3-cyano-brendane (Compound No. 11-8), oily substance. IR$\nu_{max}^{film}$ (cm$^{-1}$): 2950, 2870, 2240, 1450;

5-Oxa-endo-2-cyanomethyl-brendane (Compound No. 11-9), oily substance. IR$\nu_{max}^{film}$ (cm$^{-1}$): 2950, 2250, 1060, 1000.

According to the same procedure, there was obtained the following compound, for which the starting material was obtained by the method of Example 9-8:

5-Oxa-exo-2-ethoxycarbonylamino-isotwistane (Compound No. 11-10), solid substance, M.P., 133°–135° C. (recrystallization from diisopropyl ether). IR$\nu_{max}^{KBr}$ (cm$^{-1}$): 3290, 2940, 1710, 1520, 1240, 1070.

EXAMPLE 12

A mixture of 15% aqueous potassium hydroxide (40 ml) and 5-oxa-3-ethoxycarbonylamino-brendane (1 g) was refluxed for 7 hours and extracted with chloroform. The extract was washed with brine, dried and concentrated to give as an oily substance 5-oxa-3-amino-brendane (Compound No. 12-1) (0.83 g). IR$\nu_{max}^{film}$ (cm$^{-1}$): 3350, 3290, 2950, 1600, 1470.

According to the same procedure, there were obtained the following compounds, for which the starting materials were obtained by the method of Example 11:

5-Oxa-endo-2-amino-brendane (Compound No. 12-2), oily substance. IR$\nu_{max}^{film}$ (cm$^{-1}$): 3300, 3250, 1380, 1100;

5-Oxa-3-amino-isotwistane (Compound No. 12-3), oily substance. IR$\nu_{max}^{film}$ (cm$^{-1}$): 3350, 3280, 2930, 1250;

5-Oxa-endo-2-amino-isotwistane (Compound No. 12-4), oily substance. IR$\nu_{max}^{film}$ (cm$^{-1}$): 3350, 3280, 2940, 1590, 1090;

6-Oxa-3-amino-homobrendane (Compound No. 12-5), oily substance. IR$\nu_{max}^{film}$ (cm$^{-1}$): 3350, 3280, 2950, 2870, 1600, 1480;

6-Oxa-exo-2-amino-homobrendane (Compound No. 12-6), oily substance. IR$\nu_{max}^{film}$ (cm$^{-1}$): 3350, 3280, 1590, 1390;

6-Oxa-3-amino-homoisotwistane (Compound No. 12-7), oily substance. IR$\nu_{max}^{film}$ (cm$^{-1}$): 3330, 3270, 2920, 1520, 1250;

5-Oxa-endo-2-amino-tetracyclo[4,4,1$^{1,6}$,0$^{3,7}$,0$^{8,10}$]undecane (Compound No. 12-8), oily substance. IR$\nu_{max}^{film}$ (cm$^{-1}$): 3390, 3250, 2950, 2870, 1120.

According to the same procedure, there was obtained the following compound, for which the starting material was obtained by the method of Example 11-10:

5-Oxa-exo-2-amino-isotwistane (Compound No. 12-9), oily substance. IR$\nu_{max}^{film}$ (cm$^{-1}$): 3360, 3300, 1600.

According to the same procedure, there was obtained the following compound, for which the starting material was obtained by the method of Example 4-7:

2-Aminomethyl-4-oxo-isotwistane (Compound No. 12-10), oily substance. IR$\nu_{max}^{film}$ (cm$^{-1}$): 3350, 3290, 2910, 2850, 1080.

EXAMPLE 13

A mixture of 10% aqueous potassium hydroxide (100 ml) and 5-oxa-3-cyano-brendane (10 g) was refluxed for 15 hours while bubbling N$_2$ gas into the solution. After cooling, the reaction mixture was acidified with 10% HCl solution and extracted with ether. The extract was washed with saturated NaCl solution, dried and concentrated to give as a solid substance 5-oxa-3-carboxy-brendane (Compound No. 13-1) (8 g), M.P., 92°–93° C. (recrystallization from cyclohexane). IR$\nu_{max}^{KBr}$ (cm$^{-1}$): 2950, 2780-2650, 1710, 1270.

According to the same procedure, there was obtained the following compound:

5-Oxa-3-carboxy-isotwistane (Compound No. 13-2), solid substance, M.P., 138°–139° C. (recrystallization from cyclohexane). IR$\nu_{max}^{KBr}$ (cm$^{-1}$): 2950, 2780-2650, 1710, 1270.

EXAMPLE 14

An ethanol solution containing endo-3-ethoxycarbonylamino-endo-2-methoxycarbonyl-5-norbornene (1.8 g) was added to calcium borohydride prepared from dry calcium chloride (3.2 g) and sodium borohydride (1.4 g) in dry ethanol, while stirring and cooling at 2°–5° C. Stirring was continued at room temperature for 5 hours. After consumption of excess calcium borohydride by addition of a saturated NH$_4$Cl solution, the mixture was concentrated to give a syrupy residue, which was extracted with chloroform. The extract was washed with saturated NaCl, dried and concentrated to give as an oily substance endo-3-ethoxycarbonylamino-endo-2-hydroxymethyl-5-norbornene (Compound No. 14-1) (1.5 g). IR$\nu_{max}^{film}$ (cm$^{-1}$): 3500, 2870, 1720, 1520.

According to the same procedure, there were obtained the following compounds:

Exo-2-cyano-endo-2-hydroxymethyl-5-norbornene (Compound No. 14-2), oily substance. IR$\nu_{max}^{film}$ (cm$^{-1}$): 3400, 2230, 1650, 1480, 1440, 1280;

Exo-2-cyano-endo-2-hydroxymethyl-bicyclo[2,2,2]oct-5-ene (Compound No. 14-3), oily substance. IR$\nu_{max}^{film}$ (cm$^{-1}$): 3400, 2240, 1470, 1460, 1380;

Endo-3-ethoxycarbonylamino-endo-2-hydroxymethylbicyclo[2,2,2]oct-5-ene (Compound No. 14-4), oily substance. IR$\nu_{max}^{film}$ (cm$^{-1}$): 3500, 2950, 1710, 1520;

Endo-3-N,N-diethylcarbamoyl-endo-2-hydroxymethyl-5-norbornene (Compound No. 14-5), oily substance. IR$\nu_{max}^{film}$ (cm$^{-1}$): 3400, 2950, 1630, 1270;

Endo-8-ethoxycarbonylamino-endo-9-hydroxymethyltricyclo[3,2,2,0$^{2,4}$]non-6-ene (Compound No. 14-6), oily substance. IR$\nu_{max}^{film}$ (cm$^{-1}$): 3430, 3350, 1700, 1510;

Endo-3-hydroxymethyl-exo-2-β-chloroethyl-5-norbornene (Compound No. 14-7), oily substance. IR$\nu_{max}^{film}$ (cm$^{-1}$): 3400, 2950, 1450, 1340, 1060.

EXAMPLE 15

A solution containing 2,2-bishydroxymethyl-5-norbornene (316 mg) in tetrahydrofuran (10 ml) was added to a mixture of mercuric acetate (637 mg) in water (20 ml) and tetrahydrofuran (20 ml) while stirring at room temperature for 3 hours. To the reaction mixture, sodium hydroxide (5.6 g) and then sodium borohydride (380 mg) were added while stirring in 2 hours so that the mercury had coagulated and settled. After decantation to remove the mercury, the solvent was concentrated, and the residue was extracted with chloroform. The extract was washed with water, dried and evaporated to dryness to yield 300 mg of 5-oxa-3-hydroxymethyl-brendane (Compound No. 15-1) as an oily substance. This compound was identified with the compound obtained in Example 8 in IR spectrum.

According to the same procedure, there were obtained the following compounds:

5-Oxa-3-hydroxymethyl-isotwistane (Compound No. 15-2), oily substance;

5-Oxa-endo-2-hydroxymethyl-brendane (Compound No. 15-3), oily substance;

5-Oxa-endo-2-hydroxymethyl-isotwistane (Compound No. 15-4), oily substance;

5-Oxa-3-cyano-brendane (Compound No. 15-5), oily substance;

5-Oxa-3-cyano-isotwistane (Compound No. 15-6), solid substance.

5-Oxa-endo-2-ethoxycarbonylamino-brendane (Compound No. 15-7), oily substance;

5-Oxa-endo-2-ethoxycarbonylamino-isotwistane (Compound No. 15-8), solid substance;

5-Oxa-endo-N,N-diethylcarbamoyl-brendane (Compound No. 15-9), solid substance.

5-Oxa-endo-2-ethoxycarbonylamino-tetracyclic[4,4,1$^{1,6}$,0$^{3,7}$,0$^{8,10}$]undecane (Compound No. 15-10), solid substance, M.P., 100°–102.5° C. IR$\nu_{max}^{Nujol}$ (cm$^{-1}$): 3300, 1710, 1530;

5-Oxa-exo-2-(β-chloroethyl)-brendane (Compound No. 15-11), oily substance. IR$\nu_{max}^{film}$ (cm$^{-1}$): 2950, 1470, 1360, 1280, 1120.

According to the same procedure, there was obtained the following compound, for which the starting material was obtained by the method of Example 21-7:

Exo-2-hydroxymethyl-5-oxa-isotwistane (Compound No. 15-12), oily substance, IR$\nu_{max}^{film}$ (cm$^{-1}$): 3400, 2940, 2860, 1060, 1010.

EXAMPLE 16

A solution containing endo-3-β-hydroxyethyl-exo-2-methoxycarbonyl-5-norbornene (1.96 g) in tetrahydrofuran (20 ml) was added to a mixture of mercuric trichloroacetate prepared from mercuric oxide (2.6 g) and trichloroacetic acid (4.02 g) in water (50 ml) while stirring at room temperature for 24 hours. The reaction mixture was added to sodium borohydride (1.0 g) in 3 N sodium hydroxide (80 ml) with stirring for 3 hours. After decantation to remove the mercury, the solvent was concentrated and acidified with 10% HCl. The acidified mixture was extracted with chloroform, and the chloroform extract was washed with water, dried and concentrated. The residue was treated with an ethereal diazomethane solution and evaporated to afford as an oily substance 6-oxa-exo-2-methoxycarbonyl-homobrendane (Compound No. 16-1). IR$\nu_{max}^{film}$ (cm$^{-1}$): 2980, 1730, 1440.

According to the same procedure, there was obtained the following compound:

6-Oxa-3-hydroxymethyl-homobrendane (Compound No. 16-2), oily substance. IR$\nu_{max}^{film}$ (cm$^{-1}$): 3300, 2980, 1440.

EXAMPLE 17

To a mixture of dry chloroform (93 ml), dry tetrahydrofuran (62 ml) and 2,2-bishydroxymethyl-5-norbornene (5.5 g) was added N-bromosuccinimide (NBS, 7.0 g) at room temperature with stirring for 1 hour. After consumption of excess NBS by addition of 10% sodium thiosulfate solution, the reaction mixture was concentrated. The resulting oily layer was extracted with chloroform, and the chloroform layer was washed with a saturated NaCl solution, dried and concentrated to give as a solid substance exo-9-bromo-5-oxa-3-hydroxymethyl-brendane (Compound No. 17-1), (7.19 g), M.P., 72°–73° C. (recrystallization from ether-n-hexane). IR$\nu_{max}^{Nujol}$ (cm$^{-1}$): 3450, 1310, 1280.

According to the same procedure, there were obtained the following compounds:

Exo-9-bromo-5-oxa-endo-2-hydroxymethyl-brendane (Compound No. 17-2), oily substance. IR$\nu_{max}^{film}$ (cm$^{-1}$): 3400, 1460, 1220, 1100;

Exo-10-bromo-5-oxa-endo-2-hydroxymethyl-isotwistane (Compound No. 17-3), oily substance. IR$\nu_{max}^{film}$ (cm$^{-1}$): 3450, 1460, 1210, 1100;

Exo-9-bromo-5-oxa-3-cyano-brendane (Compound No. 17-4), solid substance, M.P., 45°–46.5° C. IR$\nu_{max}^{Nujol}$ (cm$^{-1}$): 2230, 1290, 1270, 1200, 1160;

Exo-10-bromo-5-oxa-3-cyano-isotwistane (Compound No. 17-5), solid substance, M.P., 108.5°–109° C. IR$\nu_{max}^{Nujol}$ (cm$^{-1}$): 2250, 1020.

EXAMPLE 18

A solution containing 5-oxa-3-ethoxycarbonylamino-brendane (4.3 g) in dry tetrahydrofuran, (THF, 20 ml) was added to a mixture of lithium aluminum hydride (LiAlH$_4$, 2.8 g) in dry THF (100 ml) with refluxing for 6 hours. After consumption of excess LiAlH$_4$ by addition of water, the reaction mixture was concentrated to give a residue, which was extracted with chloroform. The extract was washed with a saturated NaCl solution, dried and concentrated to give an oily 5-oxa-3-N-methylamino-brendane (Compound No. 18-1) (2.8 g). IR$\nu_{max}^{film}$ (cm$^{-1}$): 3380, 2950, 1450, 1080.

According to the same procedure, there was obtained the following compounds:

5-Oxa-3-N-methylamino-isotwistane (Compound No. 18-2), oily substance. IR$\nu_{max}^{film}$ (cm$^{-1}$): 3300, 2950, 1450, 1080;

5-Oxa-endo-2-N-methylamino-isotwistane (Compound No. 18-3), oily substance. IR$\nu_{max}^{film}$ (cm$^{-1}$): 3200, 2930, 1470, 1450;

5-Oxa-3-N,N-dimethylamino-brendane (Compound No. 18-4), oily substance. IR$\nu_{max}^{film}$ (cm$^{-1}$): 2950, 2870, 1460;

5-Oxa-3-N,N-dimethylamino-isotwistane (Compound No. 18-5), oily substance. IR$\nu_{max}^{film}$ (cm$^{-1}$): 2950, 2870, 1460.

EXAMPLE 19

Into a solution containing 5-oxa-3-N-methylamino-brendane (850 mg) and triethylamine (1.2 g) in dry ether (20 ml) was added a solution of ethyl chlorocarbonate (1.2 g) in dry ether (5 ml) with stirring at 0°–5° C. overnight. The mixture was filtered, and the filtrate was washed with 5% HCl solution and saturated NaCl solution in order, dried and concentrated to afford as an oily substance 5-oxa-3-N-methyl-N-ethoxycarbonylamino-brendane (Compound No. 19-1) (900 mg). IR$\nu_{max}^{film}$ (cm$^{-1}$): 3050-2800, 1720-1680, 1440.

According to the same procedure, there were obtained the following compounds, for which the starting materials were obtained by the method of Example 19:

5-Oxa-3-N-methyl-N-ethoxycarbonylamino-isotwistane (Compound No. 19-2), oily substance. IR$\nu_{max}^{film}$ (cm$^{-1}$): 3050-2800, 1720, 1440;

5-Oxa-3-benzyloxycarbonylaminomethyl-isotwistane (Compound No. 19-3), oily substance. IR$\nu_{max}^{film}$ (cm$^{-1}$): 3300, 2930, 1720, 1540, 1250, 700.

EXAMPLE 20

To a 4 g of 5-oxa-3-cyano-brendane in 20 ml of ethanol were added 2.8 ml of 6 N sodium hydroxide and 50 ml of 10% hydrogen peroxide. The mixture was heated cautiously for 30 minutes at 40°–50° C. and refluxed for 2 hours. Then, the reaction system was evaporated to dryness. The residue was extracted with ethyl acetate, the ethyl acetate solution was then evaporated to dryness. The new compound was 5-oxa-3-carbamoyl-brendane (Compound No. 20-1) (3.8 g), M.P., 138°–139.5° C. (recrystallized from benzene). IR$\nu_{max}^{film}$ (cm$^{-1}$): 3400, 3200, 2970, 2800, 1650.

According to the same procedure, there was obtained the following compound, for which the starting material was obtained by the method of Example 8:

5-Oxa-3-carbamoyl-isotwistane (Compound No. 20-2), solid substance, M.P., 166.5°–167.5° C. IR$\nu_{max}^{Nujol}$ (cm$^{-1}$): 3400, 3150, 1680, 1630.

EXAMPLE 21

Into a solution containing 2,2-bisethoxycarbonyl-5-norbornene (10 g) in dry tetrahydrofuran (100 ml) was added a mixture of lithium aluminum hydride (4.3 g) and dry tetrahydrofuran (100 ml) with stirring at room temperature. The reaction mixture was refluxed for 2 hours. After consumption of excess LiAlH$_4$ by addition of water, the reaction mixture was concentrated to give a residue, which was extracted with chloroform. The extract was washed with a saturated NaCl solution, dried and concentrated to give as a solid substance 2,2-bishydroxymethyl-5-norbornene (Compound No. 21-1) (9.1 g), M.P., 108°–110° C. (recrystallization from isopropanol). IR$\nu_{max}^{Nujol}$ (cm$^{-1}$): 3300, 2950, 1020.

According to the same procedure, there were obtained the following compounds:

Endo-2,3-bishydroxymethyl-5-norbornene (Compound No. 21-2), solid substance, M.P., 82°–83° C. IR$\nu_{max}^{Nujol}$ (cm$^{-1}$): 3300-3200, 1220, 1030;

Endo-2,3-bishydroxymethyl-bycyclo[2,2,2]oct-5-ene (Compound No. 21-3), solid substance, M.P., 94.5°–95° C. (recrystallization from benzene-n-hexane). IR$\nu_{max}^{Nujol}$ (cm$^{-1}$): 3300-3200, 1210, 1030, 1020;

Exo-2-hydroxymethyl-endo-2-β-hydroxyethyl-5-norbornene (Compound No. 21-4), oily substance. IR$\nu_{max}^{Nujol}$ (cm$^{-1}$): 3300, 1570, 1450, 1340, 1250, 1050;

5-Oxa-3-hydroxymethyl-isotwistane (Compound No. 21-5), oily substance IR$\nu_{max}^{film}$ (cm$^{-1}$): 3300, 2950, 2870, 1450;

According to the same procedure, there was obtained the following compound, for which the starting material was obtained by the method of Example 1-2:

2,2-Bishydroxymethyl-bicyclo[2,2,2]oct-5-ene (Compound No. 21-6), solid substance. IR$\nu_{max}^{Nujol}$ (cm$^{-1}$): 3300, 1020.

According to the same procedure, there was obtained the following compound, for which the starting material was obtained by the method of Example 65-1:

Endo-2-hydroxymethyl-exo-3-hydroxymethyl-bicyclo[2,2,2]oct-5-ene (Compound No. 21-7), solid substance, M.P., 53°–59° C. IR$\nu_{max}^{film}$ (cm$^{-1}$): 3300, 3050, 2950, 2880, 1485, 1380.

EXAMPLE 22

Into a mixture of dry benzene (30 ml), pyridine (13 ml) and 5-oxa-3-hydroxymethyl-brendane (5.0 g) was added p-toluenesulfonyl chloride (7.4 g) at 0°–5° C., and the reaction mixture was stirred at room temperature overnight. The reaction mixture was discharged into a mixture of ethyl acetate (200 ml) and 10% HCl (50 ml), and the organic layer was separated, washed with a saturated NaHCO$_3$ solution, dried and concentrated under reduced pressure to afford as a solid substance 5-oxa-3-p-toluenesulfonyloxymethyl-brendane (Compound No. 22-1) (6.6 g). IR$\nu_{max}^{Nujol}$(cm$^{-1}$): 1600, 1480, 1360, 960, 860.

According to the same procedure, there were obtained the following compounds:

5-Oxa-endo-2-p-toluenesulfonyloxymethyl-brendane (Compound No. 22-2), solid substance. IR$\nu_{max}^{Nujol}$ (cm$^{-1}$): 1600, 960, 860;

5-Oxa-endo-2-p-toluenesulfonyloxymethyl-isotwistane (Compound No. 22-3), solid substance. IR$\nu_{max}^{Nujol}$ (cm$^{-1}$): 1600, 960, 860.

According to the same procedure, there was obtained the following compound, for which the starting material is commercially available:

Endo-2-p-toluenesulfonyloxymethyl-5-norbornene (Compound No. 22-4), solid substance. IR$\nu_{max}^{Nujol}$ (cm$^{-1}$): 1600, 950, 870.

EXAMPLE 23

A mixture of methyl ethyl ketone (20 ml), 5-oxa-3-p-toluenesulfonyloxymethyl-brendane (430 mg) and lithium bromide monohydrate (400 mg) was refluxed for 3 hours and concentrated under reduced pressure. The residue was extracted with chloroform, and the chloroform layer was washed, dried and concentrated to give as an oily substance 5-oxa-3-bromomethyl-brendane (Compound No. 23-1) (300 mg). IR $\nu_{max}^{film}$ (cm$^{-1}$): 1400, 1240, 1100, 1040.

According to the same procedure, there were obtained the following compounds, for which the starting materials were obtained by the method of Example 22:

5-Oxa-endo-2-bromomethyl-brendane (Compound No. 23-2), oily substance. IR$\nu_{max}^{film}$ (cm$^{-1}$): 2950, 1220, 1050, 800;

5-Oxa-endo-2-bromomethyl-isotwistane (Compound No. 23-3), oily substance. IR$\nu_{max}^{film}$ (cm$^{-1}$): 2950, 1230, 1040;

Endo-2-bromomethyl-5-norbornene (Compound No. 23-4), B.P., 90° C./30 mmHg. IR$\nu_{max}^{film}$ (cm$^{-1}$): 3050, 2950, 1450, 1430, 1330, 1250, 1220.

EXAMPLE 24

A mixture of dimethylformamide (DMF, 20 ml), 5-oxa-3-bromomethyl-brendane (300 mg) and potassium phthalimide (250 mg) was stirred at 150° C. for 2.5 hours. After cooling, the reaction mixture was discharged into a mixture of chloroform (50 ml) and water (200 ml), and the organic layer was separated and washed with 5% Na$_2$CO$_3$ solution and then water. The solvent was concentrated to give as a solid substance 5-oxa-3-phthalimidomethyl-brendane (Compound No. 24-1) (300 mg), M.P., 135°–137° C. (recrystallization from isopropanol). Ir$\nu_{max}^{Nujol}$(cm$^{-1}$): 1770, 1730, 1610, 1430, 1400.

According to the same procedure, there were obtained the following compounds, for which the starting materials were obtained by the method of Example 23:

5-Oxa-endo-2-phthalimidomethyl-brendane (Compound No. 24-2), solid substance, M.P., 123°–124° C. (recrystallization from isopropanol). IR$\nu_{max}^{Nujol}$ (cm$^{-1}$): 1780, 1720, 1700, 1470, 1440;

5-Oxa-endo-2-phthalimidomethyl-isotwistane (Compound No. 24-3), solid substance. IR$\nu_{max}^{Nujol}$ (cm$^{-1}$): 1780, 1720, 1470.

EXAMPLE 25

A mixture of 300 mg of 5-oxa-3-phthalimidomethyl-brendane, 2 ml of ethanol and 100 mg of hydrazine monohydrate was heated under reflux for 10 minutes. After cooling, 2 ml of 10% HCl solution was added and heated for 10 minutes. The mixture was filtered to remove the precipitated substance, and the filtrate was basified with 10% NaOH and extracted with chloroform. The extract was washed with water, dried and concentrated to give as an oily substance 5-oxa-3-aminomethyl-brendane (Compound No. 25-1) (100 mg). IR$\nu_{max}^{film}$ (cm$^{-1}$): 3350, 3300, 1450, 1020.

According to the same procedure, there was obtained the following compounds, for which the starting materials were obtained by the method of Example 24:

5-Oxa-endo-2-aminomethyl-brendane (Compound No. 25-2), oily substance. $IR\nu_{max}^{film}$ (cm$^{-1}$): 3300, 3250, 2950, 1100;

5-Oxa-endo-2-aminomethyl-isotwistane (Compound No. 25-3), oily substance. $IR\nu_{max}^{film}$ (cm$^{-1}$): 3350, 3280, 2950, 1460.

EXAMPLE 26

Into a mixture of sodium metal (4 g), 5-oxa-3-carbamoyl-brendane (14.5 g) and dry ethanol (240 ml) was added bromine (15.2 g) at room temperature, and the resulting mixture was stirred for 1 hour and refluxed for 10 minutes. After evaporation of the solvent, the residue was extracted with chloroform, washed with saturated NaCl and dried. The extract was concentrated to give as an oily substance 5-oxa-3-ethoxycarbonylaminobrendane (Compound No. 26-1) (15.1 g). This compound was identified with the compound obtained in Example 11 in IR spectrum.

According the same procedure but replacing ethanolsodium ethoxide by water-sodium hydroxide, there was obtained the following compound:

5-Oxa-3-amino-brendane (Compound No. 26-2), oily substance.

EXAMPLE 27

Into a solution containing 5-oxa-3-cyano-brendane (1 g) in dry tetrahydrofuran (THF, 10 ml) was added a mixture of lithium aluminum hydride (LiAlH$_4$, 0.3 g) in dry THF (10 ml) with stirring at room temperature for 2 hours. After consumption of excess LiAlH$_4$ by addition of water, the reaction mixture was concentrated to give a residue, which was extracted with ether. The extract was washed with a saturated NaCl solution, dried and concentrated to give as an oily substance 5-oxa-3-aminomethyl-brendane (Compound No. 27-1) (0.8 g). This compound was identified with the compound obtained in Example 25 in IR spectrum.

According to the same procedure, there were obtained the following compounds:

5-Oxa-3-aminomethyl-isotwistane (Compound No. 27-2), oily substance. $IR\nu_{max}^{film}$ (cm$^{-1}$): 3400, 3300, 1030, 1010;

5-Oxa-endo-2-$\beta$-aminoethyl-brendane (Compound No. 27-3), oily substance. $IR\nu_{max}^{film}$ (cm$^{-1}$): 3400, 3320, 1040;

5-Oxa-3-($\omega$-amino-n-propyl)-isotwistane (Compound No. 27-4), oily substance. $IR\nu_{max}^{film}$ (cm$^{-1}$): 3390, 3320, 1030, 1010;

5-Oxa-exo-3-($\omega$-amino-n-propyl)-brendane (Compound No. 27-5), oily substance. $IR\nu_{max}^{film}$ (cm$^{-1}$): 3400, 3320, 1040.

EXAMPLE 28

A mixture of 5-oxa-4-oxo-endo-2-carboxy-brendane (10 g), thionyl chloride (20 ml) and methylene dichloride (60 ml) was refluxed for 6 hours. Removal of the solvent gave the corresponding acid chloride. A solution of such acid chloride in dry chloroform (50 ml) was added to a solution of diethylamine (11.8 g) in dry ether (100 ml) with stirring at 0°-5° C. The mixture was stirred at room temperature for 2 hours, and 5% HCl solution (100 ml) was added thereto. The mixture was extracted with chloroform, and the extract was washed with a saturated NaCl solution, dried and concentrated to give as a solid substance 5-oxa-4-oxo-endo-2-N,N-diethylcarbamoyl-brendane (Compound No. 28-1) (14.4 g), M.P., 78°-81° C. $IR\nu_{max}^{KBr}$ (cm$^{-1}$): 2980, 1780, 1650, 1440.

According to the same procedure, there were obtained the following compounds:

Endo-3-N,N-diethylcarbamoyl-endo-2-methoxycarbonyl-5-norbornene (Compound No. 28-2), solid substance, M.P., 167°-169° C. $IR\nu_{max}^{KBr}$ (cm$^{-1}$): 2980, 1730, 1640, 1460;

5-Oxa-3-N,N-diallylcarbamoyl-brendane (Compound No. 28-3), oily substance. $IR\nu_{max}^{film}$ (cm$^{-1}$): 2950, 1640, 1410, 1240, 1040, 930;

5-Oxa-3-pyrrolidinocarbonyl-brendane (Compound No. 28-4), solid substance, M.P., 114.5°-115.5° C. $IR\nu_{max}^{Nujol}$ (cm$^{-1}$): 1610, 1260, 1040, 1020, 800;

5-Oxa-3-morpholinocarbonyl-brendane (Compound No. 28-5), solid substance, M.P., 128.5°-131° C. $IR\nu_{max}^{Nujol}$ (cm$^{-1}$): 1620, 1280, 1250, 1110, 1020, 860.

According to the same procedure, there was obtained the following compound, for which the starting material was obtained by the method of Example 13-2:

5-Oxa-3-N,N-dimethylcarbamoyl-isotwistane (Compound No. 28-6), oily substance. $IR\nu_{max}^{Nujol}$ (cm$^{-1}$): 2930, 2850, 1630, 1390, 1160, 1020.

EXAMPLE 29

A mixture of 5-oxa-3-carboxy-brendane (1.0 g), sodium hydroxide (360 mg), water (1.4 ml) and hexamethyl phosphoramide (20 ml) was stirred at room temperature for 1 hour. Into such solution was added methyl iodide (3.4 g) with stirring at the same temperature for 1 hour. The reaction mixture was discharged into a mixture of ether and 10% HCl (50 ml) and the organic layer was separated, washed, dried and concentrated to afford an oily substance. Chromatography on silica gel using benzene for elution yielded as a solid substance 5-oxa-3-methoxycarbonyl-brendane (Compound No. 29-1) (1.2 g). $IR\nu_{max}^{film}$ (cm$^{-1}$): 2950, 1730, 1440.

According to the same procedure, there was obtained the following compound, for which the starting material was obtained by the method of Example 30:

6-Oxa-3-methoxycarbonyl-homobrendane (Compound No. 29-2), oily substance. $IR\nu_{max}^{film}$ (cm$^{-1}$): 2950, 2870, 1730, 1270.

EXAMPLE 30

Into a solution of 0.79 g of potassium hydroxide in 140 ml of water was suspended 5 g of 6-oxa-3-hydroxymethyl-homobrendane. To this solution, 6.9 g of potassium permanganate was added at such a rate that the temperature did not exceed 40° C. After 2 hours, manganese dioxide was filtered off, and excess of permanganate was reduced with a saturated sodium bisulfite solution. The mixture was again filtered, acidified with concentrated hydrochloric acid and extracted with chloroform. The extract was washed with saturated NaCl, dried and concentrated to give as a white solid 6-oxa-3-carboxyl-homobrendane (Compound No. 30-1) (4.2 g), M.P., 78.5°-80.5° C. (recrystallization from cyclohexane). $IR\nu_{max}^{KBr}$ (cm$^{-1}$): 2960, 2650, 1700, 1220, 1100.

EXAMPLE 31

To a stirred solution of 5-oxa-3-hydroxymethylisotwistane (0.5 g) in benzene (0.8 ml) and dimethyl sulfoxide (2.7 ml) were added pyridine (0.16 ml) and orthophosphoric acid (0.08 ml), and dicyclohexylcarbodiimide (1.8 g) was added portionwise thereto while cooling. The temperature was kept at a temperature of 25° to 30° C. for 6 hours. The mixture was filtered, and the insoluble bicyclohexylurea was washed with a small amount of benzene. The filtrate and the washing were combined together, washed with 10% HCl, dried and concentrated to give as an oily substance 5-oxa-3-formyl-isotwistane (Compound No. 31-1) (370 mg). IR$\nu_{max}^{film}$ (cm$^{-1}$): 2930, 2860, 1720, 1010.

According to the same procedure, there was obtained the following compound, for which the starting material was obtained by the method of Example 2-4:

2-Oxo-4-oxa-brendane (Compound No. 31-2), oily substance. IR$\nu_{max}^{film}$ (cm$^{-1}$): 2950, 2850, 1750, 1060.

According to the same procedure, there was obtained the following compound, for which the starting material was obtained by the method of Example 2-5:

2-Oxo-4-oxa-isotwistane (Compound No. 31-3), oily substance. IR$\nu_{max}^{film}$ (cm$^{-1}$): 2950, 1730, 1465, 1380.

EXAMPLE 32

Into a solution of 5-oxa-4-oxo-endo-2-carboxybrendane (5.8 g) in dry tetrahydrofuran (THF, 110 ml) was added a solution of diborane in THF at 0° C. The mixture was stirred at the same temperature for 2 hours, and excess diborane was quenched with water. The reaction mixture was concentrated under reduced pressure. This residue was diluted with chloroform, washed with water, dried and then evaporated to afford as an oily substance 5-oxa-4-oxo-endo-2-hydroxymethyl-brendane (Compound No. 32-1) (4.8 g). IR$\nu_{max}^{film}$ (cm$^{-1}$): 3450, 2960, 2880, 1780, 1360, 1170, 1040, 1020.

EXAMPLE 33

Into a solution of 5-oxa-4-oxo-endo-2-hydroxymethyl-brendane (4 g) in pyridine was added a solution of mesyl chloride (2.85 g) in dry benzene (5 ml) under cooling. After stirring for several hours, the reaction mixture was diluted with benzene and washed with 10% hydrochloric acid, aqueous sodium bicarbonate and aqueous sodium chloride in order. The organic layer was dried and evaporated. The thus obtained mesylate was dissolved in dimethylsulfoxide (DMSO, 25 ml) and treated with sodium cyanide (2 g) at 90°–105° C. for 2 hours to afford as an oily substance 5-oxa-4-oxo-endo-2-cyanomethyl-brendane (Compound No. 33-1) (3.6 g). IR$_{max}^{film}\nu$(cm$^{-1}$): 2250, 1780, 1360, 1170, 1040.

EXAMPLE 34

A mixture of 5-oxa-3-formyl-isotwistane (1.2 g), triphenyl cyanomethylidene phosphorane (2.2 g) and tetrahydrofuran (THF, 50 ml) was heated under reflux for 4 hours. Water was added thereto and the solvent was distilled off under reduced pressure. The residue was dissolved in ether, and the solution was washed with brine, dried and concentrated under reduced pressure. Chromatography on silica gel using hexane-isopropyl ether for elution yielded as an oily substance 5-oxa-3-($\beta$-cyanoethylene)-isotwistane (Compound No. 34-1) (800 mg). IR$\nu_{max}^{film}$ (cm$^{-1}$): 2960, 2220, 1630.

EXAMPLE 35

5-Oxa-3-($\beta$-cyanoethylene)-isotwistane (800 mg) was hydrogenated with 5% Pd-C (160 mg) in ethanol under atmospheric pressure. The ethanolic solution thus obtained was filtered to remove the catalyst, and the filtrate was concentrated to afford an oily substance. Chromatography on silica gel using benzene for elution yielded as a solid substance 5-oxa-3-($\beta$-cyanoethyl)-isotwistane (Compound No. 35-1) (800 mg), M.P., 53°–55° C. (recrystallization from isopropyl ether). IR$\nu_{max}^{Nujol}$ (cm$^{-1}$): 2240, 1080, 1030, 1010.

According to the same procedure, there was obtained the following compound, for which the starting material was obtained by the method of Example 7-1:

2-Ethoxycarbonylmethyl-4-oxo-isotwistane (Compound No. 35-2), oily substance. IR$\nu_{max}^{film}$ (cm$^{-1}$): 2930, 2860, 1730, 1300, 1150, 1070, 1030.

EXAMPLE 36

5-Oxa-3-N-ethyl-N-benzyloxycarbonylaminomethylisotwistane (3.3 g) was hydrogenolyzed with 10% Pd-c (0.25 g) in ethanol (100 ml) under atmospheric pressure. The ethanolic solution thus obtained was filtered to remove the catalyst, and the filtrate was concentrated to afford as an oily substance 5-oxa-3-N-ethylaminomethyi-isotwistane (Compound No. 36-1). IR$\nu_{max}^{film}$ (cm$^{-1}$): 332, 2960, 1450, 1370, 1220.

EXAMPLE 37

A mixture of endo-3-($\beta$-chloroethyl)-exo-3-methoxycarbonyl-5-norbornene (1 g), potassium acetate (5 g), acetic acid (1 ml) and N,N-dimethylformamide (DMF, 5 ml) was heated at 120° C. for 3 hours. The mixture was discharged into a mixture of benzene (50 ml) and water (50 ml), and the organic layer was separated, washed, dried and concentrated under reduced pressure to afford as an oily substance endo-3-($\beta$-acetoxyethyl)-exo-2-methoxycarbonyl-5-norbornene (Compound No. 37-1) (1 g). IR$\nu_{max}^{film}$ (cm$^{-1}$): 1740, 1430, 1360.

EXAMPLE 38

A mixture of endo-3-($\beta$-acetoxyethyl)-exo-2-methoxycarbonyl-5-norbornene (1 g), conc. H$_2$SO$_4$ (several drops) and methanol (100 ml) was stirred at room temperature for 3 hours and concentrated under reduced pressure. The residue was diluted with water and extracted with ether. The extract was washed with water and dried. Removal of the solvent gave as an oily substance endo-3-($\beta$-hydroxyethyl)-exo-2-methoxycarbonyl-5-norbornene (Compound No. 38-1) (850 mg). IR$\nu_{max}^{film}$ (cm$^{-1}$): 3400, 1730, 1430, 1240.

EXAMPLE 39

Into a solution of sodium metal (0.133 g) in dry ethanol (8.6 ml) was added a solution of tricyclo[3,2,2,0$^{2,4}$]-nonene-(6)-endo-8,9-dicarboxylic acid anhydride (1.0 g) in dry ethanol (5.8 ml) with stirring at room temperature for 2 hours and concentrated under reduced pressure. The residue was diluted with water, made acidic with 10% HCl and extracted with chloroform. The extract was washed with water and dried. Removal of the solvent gave a solid endo-8-carboxy-endo-9-ethoxycarbonyltricyclo[3,2,2,0$^{2,4}$]nonene-(6) (Compound No. 39-1), M.P., 85°–87° C. IR$\nu_{max}^{KBr}$ (cm$^{-1}$): 2735, 2650, 1735, 1700, 1185.

EXAMPLE 40

Into a solution of 5-oxa-3-aminomethyl-isotwistane (1.0 g) in dry dichloromethane (10 ml) was added trifluoroacetic anhydride (960 mg) with stirring at room temperature for 3 hours. The mixture was discharged into a mixture of 5% aqueous sodium bicarbonate and chloroform, and the organic layer was washed with water and dried. Removal of the solvent gave as a solid substance 5-oxa-3-N-trifluoroacetylaminomethyl-isotwistane (Compound No. 40-1) (0.9 g), M.P., 81.5°–84° C. IR$\nu_{max}^{Nujol}$ (cm$^{-1}$): 3350-3050, 1700.

According to the same procedure, using 5-oxa-3-amino-isotwistane (1.52 g), triethylamine (2 g) and acetyl chloride (0.86 g), there was obtained as an oily substance 5-oxa-3-N-acetylamino-isotwistane (Compound No. 40-2) (800 mg). IR$\nu_{max}^{Nujol}$ (cm$^{-1}$): 3400, 2960, 1660, 1560.

EXAMPLE 41

Into a solution containing 5-oxa-3-N-acetylaminomethyl-isotwistane (600 mg) in dry tetrahydrofuran (THF, 10 ml) was added a mixture of lithium aluminum hydride (LiAlH$_4$, 218 mg) in dry tetrahydrofuran (10 ml) with refluxing for 6 hours. After consumption of excess LiAlH$_4$ by addition of water, the reaction mixture was concentrated to give a residue, which was extracted with chloroform. The extract was washed with a saturated NaCl solution, dried and concentrated to give as an oily substance 5-oxa-3-N-ethylaminomethyl-isotwistane (Compound No. 41-1) (420 mg).

According to the same procedure, there were obtained the following compounds, for which the starting materials were obtained by the method of Example 28:

5-Oxa-3-N,N-diallylaminomethyl-brendane (Compound No. 41-2), oily substance. IR$\nu_{max}^{film}$ (cm$^{-1}$): 2950, 1470, 1380, 1040;

5-Oxa-3-pyrrolidinomethyl-brendane (Compound No. 41-3), oily substance. IR$\nu_{max}^{film}$ (cm$^{-1}$): 2950, 1470, 1360, 1040;

5-Oxa-3-morpholinomethyl-brendane (Compound No. 41-4), oily substance. IR$\nu_{max}^{film}$ (cm$^{-1}$): 2950, 1470, 1360, 1040.

According to the same procedure, there was obtained the following compound, for which the starting material was obtained by the method of Example 28-6:

5-Oxa-3-N,N-dimethylaminomethyl-isotwistane (Compound No. 41-5), oily substance. IR$\nu_{max}^{Nujol}$ (cm$^{-1}$): 2930, 2860, 2760, 1570, 1550, 1010.

EXAMPLE 42

Into a solution of 5-oxa-3-N-trifluoroacetylaminomethyl-isotwistane (1.0 g) and propargyl bromide (1.8 g) in dry acetone (45 ml) was added potassium hydroxide (709 mg) with stirring at 60° C. The reaction mixture was refluxed for 1 hour and concentrated under reduced pressure. A solution containing potassium hydroxide (709 mg) in water (10 ml) was added to a residue with refluxing for 15 minutes. After cooling, the mixture was extracted with chloroform, and the extract was washed with water and dried. Removal of the solvent gave as an oily substance 5-oxa-3-N-propargylaminomethyl-isotwistane (Compound No. 42-1) (200 mg). IR$\nu_{max}^{film}$ (cm$^{-1}$): 3400-3100, 2950, 1520.

According to the same procedure, but replacing propargyl bromide by allyl bromide, there was obtained as an oily substance 5-oxa-3-N-allylaminomethyl-isotwistane (Compound No. 42-2). IR$\nu_{max}^{film}$ (cm$^{-1}$): 3300, 2950, 1450, 1380.

EXAMPLE 43

A solution of methyl lithium (1% in ether, ca. 20 mmole) was added dropwise to 5-oxa-3-cyano-isotwistane (2.2 g) in dry ether (10 ml) at room temperature under nitrogen. After stirring at room temperature for 6 hours, 50 ml of 10% HCl solution was added cautiously. The mixture was extracted with benzene, dried and concentrated to give as an oily substance 5-oxa-3-acetyl-isotwistane (Compound No. 43-1). IR$\nu_{max}^{film}$ (cm$^{-1}$): 2950, 1700, 1440, 1360, 1280.

5-Oxa-3-acetyl-isotwistane oxime (Compound No. 43-2) was obtained by the usual method, M.P., 87°–90° C. IR$\nu_{max}^{Nujol}$ (cm$^{-1}$): 3300, 1280, 1000, 890.

EXAMPLE 44

A solution containing 5-oxa-3-acetyl-isotwistane oxime (900 mg) in dry tetrahydrofuran (20 ml) was added to a mixture of lithium aluminum hydride (LiAlH$_4$, 700 mg) in dry tetrahydrofuran (10 ml) with refluxing for 8 hours. After consumption of excess LiAlH$_4$ by addition of water, the reaction mixture was concentrated to give a residue, which was extracted with chloroform. The extract was washed with a saturated NaCl solution, dried and concentrated to give as an oily substance 5-oxa-3-(α-aminoethyl)-isotwistane (Compound No. 44-1) (750 mg). IR$\nu_{max}^{film}$ (cm$^{-1}$): 3450, 3300, 2950, 1470, 1440, 1370.

According to the same procedure, there was obtained the following compound, for which the starting material was obtained by the method of Example 68-1:

2-Amino-4-thia-brendane (Compound No. 44-2), oily substance. IR$\nu_{max}^{film}$ (cm$^{-1}$): 3200, 3250, 2950, 1580.

According to the same procedure, there was obtained the following compound, for which the starting material was obtained by the method of Example 68-2:

2-Amino-4-oxa-brendane (Compound No. 44-3), oily substance. IR$\nu_{max}^{film}$ (cm$^{-1}$): 3380, 3300, 2950, 2870, 1600, 1360.

According to the same procedure, there was obtained the following compound, for which the starting material was obtained by the method of Example 68-3:

2-Amino-4-oxa-isotwistane (Compound No. 44-4), oily substance. IR$\nu_{max}^{film}$ (cm$^{-1}$): 3370, 3300, 2930, 2870, 1480, 1070, 680.

EXAMPLE 45

Into a mixture of dry benzene (30 ml), pyridine (30 ml) and exo-3-cyano-endo-3-hydroxymethyl-5-norbornene (10 g) was added methanesulfonyl chloride (9.20 g) at 0°–5° C., and the mixture was stirred at room temperature overnight. The reaction mixture was discharged into a mixture of ethyl acetate and 10% HCl, and the organic layer was separated, washed, dried and concentrated under reduced pressure to afford as an oily substance exo-3-cyano-endo-3-mesyloxymethyl-5-norbornene (Compound No. 45-1). IR$\nu_{max}^{film}$ (cm$^{-1}$): 2980, 2870, 2230, 1460, 1360.

According to the same procedure but replacing methanesulfonyl chloride with p-toluenesulfonyl chloride, there was obtained the following compound:

Exo-3-cyano-endo-3-p-toluenesulfonyloxymethyl-bicyclo[2,2,2]oct-5-ene (Compound No. 45-2), solid substance, M.P., 95°–96.5° C. IR$\nu_{max}^{Nujol}$ (cm$^{-1}$): 2250, 1600, 1180, 860.

EXAMPLE 46

A mixture of exo-3-cyano-endo-3-mesyloxymethyl-5-norbornene (15 g), potassium thioacetate (16.3 g) and dry acetone (300 ml) was refluxed for 12 hours. After evaporation of the solvent, the residue was extracted with ether. The extract was washed with a saturated NaCl solution, dried and evaporated to give an oily substance, which was chromatographed on silica gel.

Exo-3-cyano-endo-3-acetylthiomethyl-5-norbornene (Compound No. 46-1) (4.5 g) as an oily substance was eluted with benzene. IR$\nu_{max}^{film}$ (cm$^{-1}$): 2970, 2230, 1700, 1340, 1130.

According to the same procedure, there was obtained the following compound, for which the starting material was obtained by the method of Example 24-4:

Endo-2-acetylthiomethyl-5-norbornene (Compound No. 46-2), oily substance. IR$\nu_{max}^{film}$ (cm$^{-1}$): 3000, 1340, 1220.

EXAMPLE 47

A mixture of exo-3-cyano-endo-3-acetylthiomethyl-5-norbornene (4.5 g), sodium carbonate (3.0 g) and dry methanol (50 ml) was stirred at room temperature for 24 hours. After evaporation of the solvent, the residue was acidified with dilute HCl solution and extracted with ether. The extract was washed with a saturated NaCl solution, dried and concentrated to give as an oily substance exo-3-cyano-endo-3-mercaptomethyl-5-norbornene (Compound No. 47-1) (2.5 g). IR$\nu_{max}^{film}$ (cm$^{-1}$): 2970, 2230, 1360, 1180, 960.

According to the same procedure, there was obtained the following compound, for which the starting material was obtained by the method of Example 46-2:

Endo-2-mercaptomethyl-5-norbornene (Compound No. 47-2), oily substance. IR$\nu_{max}^{film}$ (cm$^{-1}$): 3000, 1340, 1220.

EXAMPLE 48

Into a solution of exo-3-cyano-endo-3-mercaptomethyl-5-norbornene (2.5 g) in dry chloroform (10 ml) was added bromine (Br$_2$, 2.9 g) with stirring at 0° C. for 1 hour. After consumption of excess Br$_2$ by addition of a dilute sodium thiosulfate solution, the mixture was extracted with chloroform. The extract was washed with a saturated NaCl solution, dried and concentrated to give a solid substance, which was chromatographed on silica gel to give exo-9-bromo-5-thia-3-cyano-brendane (Compound No. 48-1) (1.0 g), M.P., 106°–108° C. IR$\nu_{max}^{KBr}$ (cm$^{-1}$): 2930, 2230, 1450, 1270, 700.

According to the same procedure, there was obtained the following compound, for which the starting material was obtained by the method of Example 47-2:

Exo-2-bromo-4-thia-brendane (Compound No. 48-2), oily substance. IR$\nu_{max}^{film}$ (cm$^{-1}$): 2950, 2870, 1450, 1230.

EXAMPLE 49

A solution containing exo-9-bromo-5-thia-3-cyano-brendane (0.9 g) in dry tetrahydrofuran (20 ml) was added to a mixture of lithium aluminum hydride (LiAlH$_4$, 1.05 g) in dry tetrahydrofuran (40 ml) with refluxing for 15 hours. After consumption of excess LiAlH$_4$ by addition of water, the reaction mixture was concentrated to give a residue, which was extracted with chloroform. The extract was washed, dried and concentrated to give as an oily substance 5-thia-3-aminomethyl-brendane (Compound No. 49-1). IR$\nu_{max}^{film}$ (cm$^{-1}$): 3380, 3330, 2950, 1580, 1440.

EXAMPLE 50

Into a solution of 5-oxa-3-aminomethyl-isotwistane (1.5 g) in N,N-dimethylformamide (20 ml) was added benzyl chloride (2.5 g) with stirring at 80° C. for 5 hours. After cooling, the solution was discharged into a mixture of water and ether, and the organic layer was separated, washed, dried and concentrated under reduced pressure to afford as an oily substance 5-oxa-3-N-benzylaminomethyl-isotwistane (Compound No. 50-1) (1.2 g). IR$\nu_{max}^{film}$ (cm$^{-1}$): 3300, 2950, 1320, 700.

EXAMPLE 51

A mixture of exo-2-cyano-endo-2-toluenesulfonyloxymethyl-bicyclo[2,2,2]oct-5-ene (5.0 g), lithium bromide monohydrate (8.24 g), N,N-dimethylformamide (50 ml) and dimethylsulfoxide (50 ml) was heated at 100° C. for 3 hours. After cooling, the reaction mixture was discharged into a mixture of water and ether, and the organic layer was separated, washed, dried and concentrated under reduced pressure to afford as an oily substance exo-2-cyano-endo-2-bromomethyl-bicyclo[2,2,2]oct-5-ene (Compound No. 51-1) (3.4 g). IR$\nu_{max}^{film}$ (cm$^{-1}$): 3050, 2950, 2240, 1460, 1380, 1250.

EXAMPLE 52

A mixture of exo-2-cyano-endo-2-bromomethylbicyclo[2,2,2]oct-5-ene (5.0 g), sodium hydrosulfide (4.4 g), N,N-dimethylformamide (20 ml) and dimethylsulfoxide (20 ml) was stirred at room temperature for 5 hours. The mixture was discharged into a mixture of water and ether, and the organic layer was separated, washed, dried and concentrated under reduced pressure to afford an oily substance. Chromatography on silica gel using benzene for elution yielded as an oily substance 5-thia-3-cyano-isotwistane (Compound No. 52-1) (1.5 g). IR$\nu_{max}^{film}$ (cm$^{-1}$): 2950, 2870, 2230, 1450, 1190.

EXAMPLE 53

A solution of 5-thia-3-cyano-isotwistane (500 mg) in dry ether (10 ml) was added to a mixture of lithium aluminum hydride (LiAlH$_4$, 265 mg) in dry ether (10 ml) and stirred at 0°–5° C. for 2 hours. After consumption of excess LiAlH$_4$ by addition of water, the reaction mixture was extracted with ether. The extract was washed with a saturated NaCl solution, dried and concentrated to give a solid 5-thia-3-aminoethyl-isotwistane (Compound No. 53-1) (430 mg), M.P., 75°–77° C. IR$\nu_{max}^{film}$ (cm$^{-1}$): 3360, 3300, 2950, 1600, 1470, 1450.

EXAMPLE 54

A mixture of 5-thia-3-aminomethyl-isotwistane (250 mg), potassium metaperiodate (296 mg) in water (25 ml) and methanol (25 ml) was stirred at room temperature for 1 hour. After removal of methanol, the mixture was extracted with chloroform. The extract was washed, dried and concentrated to give as an oily substance 5-thia-5-oxo-3-aminomethylisotwistane (Compound No. 54-1) (160 mg). IR$\nu_{max}^{film}$ (cm$^{-1}$): 3370, 3300, 2930, 1450, 1040, 1020.

According to the same procedure, there was obtained the following compound, for which the starting material was obtained by the method of Example 62:

5-Thia-5-oxo-3-amino-isotwistane (Compound No. 54-2), oily substance. IR$\nu_{max}^{film}$ (cm$^{-1}$): 3370, 3320, 2940, 1450, 1040, 1020.

EXAMPLE 55

5-Thia-3-aminomethyl-isotwistane (300 mg) was dissolved in acetic acid (8 N, 6 ml), and a solution of potassium permanganate (0.41 g) in water (3.4 ml) was added thereto with stirring at 25° C. in 0.5 hour. This mixture was cooled in ice, decolorised by passing in sulfur dioxide, adjusted to pH 12 with sodium hydroxide and extracted with chloroform. The extract was washed, dried and concentrated to give as an oily substance 5-thia-5,5- dioxo-3-aminomethylisotwistane (Compound No. 55-1) (220 mg). IR$\nu_{max}^{film}$ (cm$^{-1}$): 3400, 3330, 2930, 1295, 1220, 1110, 760.

According to the same procedure, there was obtained the following compound, for which the starting material was obtained by the method of Example 62:

5-Thia-5,5-dioxo-3-amino-isotwistane (Compound No. 55-2), oily substance. IR$\nu_{max}^{film}$ (cm$^{-1}$): 3370, 3310, 2940, 1290, 1220. 1110.

EXAMPLE 56

A mixture of endo-2-ethoxycarbonylamino-endo-3-hydroxymethyl-brendane (500 mg), 50% H$_2$SO$_4$ solution (10 ml) and ethanol (20 ml) was heated at 70° C. for 2 hours. After cooling, the reaction mixture was discharged into a sodium bicarbonate solution (200 ml) and extracted with chloroform. The extract was washed with a saturated NaCl solution, dried and concentrated to give as an oily substance 5-oxa-endo-2-ethoxycarbonylamino-brendane (Compound No. 56-1) (500 mg). This compound was identified with the compound obtained in Example 11 in IR spectrum.

According to the same procedure, there was obtained the following compound:

5-Oxa-3-ethoxycarbonyl-isotwistane (Compound No. 56-2), oily substance. IR$\nu_{max}^{film}$ (cm$^{-1}$): 2950, 2860, 1730, 1460, 1330.

EXAMPLE 57

A mixture of 5-oxa-exo-2-($\beta$-chloroethyl)-brendane (1.86 g), sodium cyanide (1.47 g) and dimethyl sulfoxide (DMSO, 20 ml) was heated at 90°-100° C. for 5 hours. After cooling, the reaction mixture was discharged into a mixture of water and ether, and the organic layer was separated, washed, dried and concentrated under reduced pressure to afford an oily substance. Chromatography on silica gel using benzene for elution yielded as an oily substance 5-oxa-exo-2-($\beta$-cyanoethyl)-brendane (Compound No. 57-1) (1.2 g). IR$\nu_{max}^{film}$ (cm$^{-1}$): 2950, 2230, 1450, 1120.

According to the same procedure, there was obtained the following compound:

5-Oxa-endo-2-cyanomethyl-isotwistane (Compound No. 57-2), oily substance IR$\nu_{max}^{film}$ (cm$^{-1}$): 2950, 2240, 1450, 1040.

EXAMPLE 58

A mixture of 5-oxa-endo-2-($\beta$-chloroethyl)-brendane (1.9 g), benzylamine (1.56 g), potassium carbonate (1.4 g) and dry N,N-dimethylformamide (19 ml) was heated at 100° C. for 2.5 hours. After cooling, the solution was discharged into a mixture of water and ether, and the organic layer was separated, washed, dried and concentrated under reduced pressure to afford as an oily substance 5-oxa-2-[$\beta$-(benzylamino)ethyl]-brendane (Compound No. 58-1). IR$\nu_{max}^{film}$ (cm$^{-1}$): 3300, 2950, 2850, 1480, 1350, 760.

EXAMPLE 59

Into a solution of 5-oxa-3-benzyloxycarbonylaminomethyl-isotwistane (300 mg) in dry dimethyl sulfoxide (5 ml) was added sodium hydride (65%, 123 mg) with stirring at 120°-130° C. for 1.5 hours. After cooling, a solution of ethyl iodide (518 mg) in dry dimethylformamide (5 ml) was added to the resulting mixture and stirred at 9° C. for 10 hours. The mixture was discharged into a mixture of benzene and water and extracted with benzene. The extract was washed, dried and concentrated to afford an oily substance. Chromatography on silica gel using chloroform for elution yielded as an oily substance 5-oxa-3-(N-ethyl-N-benzyloxycarbonyl)aminomethyl-isotwistane (Compound No. 59-1) (450 mg). IR$\nu_{max}^{film}$ (cm$^{-1}$): 2930, 2860, 1700, 1460, 1250, 700.

EXAMPLE 60

A mixture of 5-thia-3-cyano-isotwistane (1 g), potassium hydroxide (85%, 1.25 g) and ethylene glycol (4.5 ml) was refluxed for 15 minutes. After cooling, the mixture was discharged into a mixture of 10% HCl (20 ml) and benzene and extracted with benzene. The extract was washed, dried and concentrated to give as a solid substance 5-thia-3-carboxy-isotwistane (Compound No. 60-1) (650 mg), M.P., 108°-113° C. IR$\nu_{max}^{KBr}$ (cm$^{-1}$): 2950, 1700, 1410, 1290, 920.

EXAMPLE 61

Into a solution of 5-thia-3-carboxy-isotwistane (640 mg), triethylamine (327 mg) in dry acetone (14 ml) was added ethyl chlorocarbonate (421 mg) with stirring at $-20°$ C. for 1 hour. Into a reaction mixture was added sodium azide (273 mg) in water (2 ml) at $-20°$ C. for 1 hour. After heating to room temperature, the reaction mixture was extracted with benzene and dried. After evaporation of the solvent, the residue was dissolved in dry ethanol (100 ml) and refluxed for 2 hours.

After removal of the solvent, chromatography on silica gel using chloroform for elution yielded as a solid substance 5-thia-3-ethoxycarbonylamino-isotwistane (Compound No. 61-1) (620 mg), M.P., 73°-76° C. IR$\nu_{max}^{film}$ (cm$^{-1}$): 3330, 2940, 2870, 1700, 1520, 1270, 1060.

EXAMPLE 62

A mixture of 5-thia-3-ethoxycarbonylamino-isotwistane (283 mg), potassium hydroxide (85%, 309 mg) and ethylene glycol (1.2 ml) was refluxed for 15 minutes. After cooling, the mixture was discharged into a mixture of water and chloroform and extracted with chloroform.

The extract was washed, dried and concentrated to give as an oily substance 5-thia-3-amino-isotwistane (Compound No. 62-1) (155 mg). IR$\nu_{max}^{KBr}$ (cm$^{-1}$): 3330, 3250, 2930, 2850, 1450, 1110.

EXAMPLE 63

Into a solution of 1.0 g of dimethylamine hydrochloride in 8 ml of methanol was added potassium hydroxide (0.5 g), and 1.8 g of 5-oxa-3-acetyl-isotwistane (1.8 g) was added thereto in one portion. The resulting suspension was stirred at room temperature for 15 minutes, and then a solution of sodium cyanoborohydride (0.25 g) in 5 ml of methanol was added dropwise over 30 minutes. The suspension was stirred for 30 minutes. Potassium hydroxide (0.72 g) was then added, and stirring was continued.

The reaction mixture was filtered with suction, and the filtrate was extracted with benzene. The extract was washed, dried and concentrated to give as an oily substance 5-oxa-3-($\alpha$-N,N-dimethylamino)ethyl-isotwistane (Compound No. 63-1). IR$\nu_{max}^{film}$ (cm$^{-1}$): 2950, 2870, 1460.

According to the same procedure, there were obtained the following compounds, for which the starting materials were obtained by the method of Example 31-3:

4-Oxa-2-N,N-dimethylamino-isotwistane (Compound No. 63-2), oily substance IR$\nu_{max}^{film}$ (cm$^{-1}$): 2950, 2860, 1460, 1060;

4-Oxa-2-morpholino-isotwistane (Compound No. 63-3), oily substance. IR$\nu_{max}^{film}$ (cm$^{-1}$): 2820, 1950, 1430, 1050.

EXAMPLE 64

A solution of 5-oxa-3-carboxy-brendane (2.0 g), thionyl chloride (20 ml) and methylene dichloride (20 ml) was refluxed for 3 hours. The reaction mixture was evaporated to dryness, benzene (20 ml) was added thereto, and the resulting mixture was evaporated to remove thionyl chloride. A solution of thus obtained acid chloride in tetrahydrofuran (6.5 ml) was added to a solution of hydroxylamine hydrochloride (3.3 g) and sodium hydroxide (1.9 g) in water (15 ml) at 0° C. The reaction mixture was stirred for 2 hours at the same temperature. The mixture was extracted with chloroform, washed, dried and concentrated to give as an oily substance 5-oxa-3-(N-hydroxycarbamoyl)-brendane (Compound No. 64-1) (2.0 g). IR$\nu_{max}^{film}$ (cm$^{-1}$): 3300, 3250, 2950, 1650, 1480, 1020.

To a solution of sodium ethoxide (0.25 g) in dry toluene (5 ml) was added a solution of 5-oxa-3-(N-hydroxycarbamoyl)-brendane (1.0 g) in dry toluene (5 ml) with stirring at room temperature. The reaction mixture was refluxed for 2 hours, ethanol (10 ml) was added thereto and then refluxing was made for 2 hours. After evaporation of the solvent, the residue was discharged into a mixture of 10% HCl solution and chloroform. The organic layer was separated, washed, dried and concentrated to give an oily residue. Chromatography on silica gel using chloroform for elution yielded as an oily substance 5-oxa-3-ethoxycarbonylamino-brendane (Compound No. 64-2) (0.20 g). This compound was identified with the compound obtained in Example 11 in IR spectrum.

EXAMPLE 65

Into a mixture of methanol (6.4 g), triethylamine (10.1 g) and dry benzene (50 ml) was added endo-2-chlorocarbonyl-exo-3-chlorocarbonyl-bicyclo[2,2,2]oct-5-ene (7.3 g) obtained in Example 1-6 at 0°-5° C. and the the reaction mixture was stirred at room temperature for 1 hour. The reaction mixture was discharged into a water, and the organic layer was separated, washed with a saturated NaHCO$_3$ solution, dried and concentrated under reduced pressure to afford as an oily substance endo-2-methoxycarbonyl-exo-3-methoxycarbonyl-bicyclo[2,2,2]oct-5-ene (Compound No. 65-1) (8.2 g). IR$\nu_{max}^{film}$ (cm$^{-1}$): 2955, 1740, 1400, 1290, 1200.

EXAMPLE 66

According to the same method of T. Mukaiyama et al. [Chem. Lett., 635 (1977)], to a stirred suspension of 1-methyl-2-fluoropyridinium tosylate (3.6 g) in dry CHCl$_3$ (69 ml) were added exo-2-hydroxymethyl-5-oxa-isotwistane (2 g) and triethylamine (1.3 g) in CHCl$_3$ (69 ml).

A homogeneous solution was stirred at room temperature for 30 minutes under nitrogen atmosphere. Chloroform was evaporated in vacuo and to the residual solid were added by HMPA (57 ml) and NaN$_3$ (1.5 g). The solution was kept at 80° C. for 1 hour with stirring. The reaction mixture was cooled and poured to water, and exo-2-azidemethyl-5-oxa-isotwistane was extracted with ether.

The extract was washed with brine to remove 1-methyl-2-pyridone and HMPA, dried and concentrated in vacuo to give as an oily substance exo-2-azidemethyl-5-oxa-isotwistane (Compound No. 66-1). IR$\nu_{max}^{film}$ (cm$^{-1}$): 2950, 2870, 2100, 1480, 1270, 1050.

EXAMPLE 67

Into a solution containing exo-2-azidemethyl-5-oxa-isotwistane (1.5 g) in dry ether (20 ml) was added a mixture of LiAlH$_4$ (678 mg) and dry ether (6.8 ml) with stirring at room temperature. The reaction mixture was refluxed for 2 hours. After consumption of excess LiAlH$_4$ by addition of water, the reaction mixture was extracted with ether. The extract was washed with a saturated NaCl solution and dried. After removal of the solvent, exo-2-aminomethyl-5-oxa-isotwistane (Compound No. 67-1) (700 mg) was obtained as an oily substance. IR$\nu_{max}^{film}$ (cm$^{-1}$): 3320, 3280, 1060, 1040, 950.

According to the same procedure, there was obtained the following compound, for which the starting material was obtained by the method of Example 69-1:

2-Amino-4-thia-brendane (Compound No. 67-2), oily substance.

EXAMPLE 68

A mixture of 2-oxo-4-thia-brendane (10 g) (known compound, cf. J.C.S., 38, 1803 (1973)), hydroxylamine hydrochloride (10.84 g), ethanol (200 ml), water (80 ml) and sodium carbonate (44.4 g) was refluxed for 6 hours. After cooling, the reaction mixture was extracted with ethyl acetate. The extract was washed with a saturated NaCl solution, dried and concentrated to give an oily residue. Chromatography on silica gel using chloroform for elution yielded as a solid substance, 2-hydroxyimino-4-thia-brendane (Compound No. 68-1). IR$\nu_{max\text{-}Nujol}$ (cm$^{-1}$): 3250, 3130, 1690, 1620, 1580.

According to the same procedure, there was obtained the following compound, for which the starting material was obtained by the method of Example 32-2:

2-Hydroxyimino-4-oxa-brendane (Compound No. 68-2), oily substance. IR$\nu_{max}^{film}$ (cm$^{-1}$): 3300, 2950, 2870, 1240, 1060.

According to the same procedure, there was obtained the following compound, for which the starting material was obtained by the method of Example 32-3:

2-Hydroxyimino-4-oxa-isotwistane (Compound No. 68-3), solid substance, M.P., 107°–109° C. IR$\nu_{max}^{film}$ (cm$^{-1}$): 3220, 3100, 2930, 2860, 1085, 1065, 980.

EXAMPLE 69

A mixture of sodium azide (200 mg), exo-2-bromo-4-thia-brendane (150 mg) and 95% ethanol (2 ml) was refluxed for 7 hours. After evaporation of the solvent, the residue was discharged into a mixture of water and ether. The organic layer was separated, washed with a saturated NaCl solution and dried.

The evaporation of the solvent gave 2-azide-4-thia-brendane (Compound No. 69-1) (100mg), oily substance. IR$\nu_{max}^{film}$ (cm$^{-1}$): 2950, 2850, 2100, 1480, 1440, 1320, 1240, 680.

EXAMPLE 70

A mixture of lead tetraacetate (44 g), calcium carbonate (5 g), endo-2-hydroxymethyl-bicyclo[2,2,2]oct-5-ene (14.2 g) and benzene (250 ml) was refluxed for 12 hours. The reaction mixture was filtered to remove the precipitate, and the filtrate was concentrated to afford an oily substance. Chromatography on silica gel using chloroform for elution yielded as an oily substance exo-2-acetoxy-4-oxa-isotwistane (Compound No. 70-1) (11.6 g). IR$\nu_{max}^{film}$ (cm$^{-1}$): 2950, 2870, 1735, 1370, 1250, 1220, 1100, 1025, 1000.

EXAMPLE 71

A solution of ethoxycarbonylmethyl diethylphosphonate (2.65 g) in 5 ml of THF was added dropwise to a stirred suspension of 0.44 g of NaH (65% mineral oil dispersion) in 15 ml of anhydrous THF.

Stirring was continued until hydrogen evolution ceased, and then a solution of 0.90 g of 4-oxa-2-oxo-isotwistane in 5 ml of THF was added. After 2 hours of stirring at room temperature, water was added. The mixture was extracted with ethyl acetate, and the organic extract was dried over MgSO$_4$ and evaporated. The residue was chromatographed on silica gel as eluent with benzene and ethyl acetate to afford 0.86 g of an oily objective product. IR$\nu_{max}^{film}$ (cm$^{-1}$): 2940, 2860, 1715, 1650, 1480, 1450, 1380, 1240, 1200.

EXAMPLE 72

A mixture of sucrose (22 g), magnesium stearate (0.25 g), gum acacia (0.75 g), water (0.75 ml) and 5-oxa-3-aminomethyl-isotwistane hydrochloride (1.25 g) was blended and then compressed into hard lozenges, such that each lozenge weighed 1.0 g. Such a lozenge contained 50 mg of 5-oxa-3-aminomethyl-isotwistane hydrochloride.

EXAMPLE 73

A solution of 5-oxa-3-aminomethyl-isotwistane hydrochloride (1.0 g) in sterile distilled water (99 g) containing chlorobuthanol (0.58% w/w) was filled into squeezable plastic containers which were each closed with a nozzle suitable for producing a coarse spray when the container was squeezed. There was thus obtained a spray composition suitable for administration by inhalation.

EXAMPLE 74

An intimate mixture of 5-oxa-3-aminomethyl-isotwistane hydrochloride (16.5 g), maize starch (11.2 g), calcium phosphate (22 g) and magnesium stearate (0.25 g) was compressed, and the compressed mixture was then broken down into granules by passage through a 16-mesh screen.

The resultant granules were compressed into tablets, each of which contained 50 mg of active ingredient.

EXAMPLE 75

Acute toxicity:

Six male dd-strain mice, weighing 25±3 g, were used in each group. Test drugs were injected subcutaneously (0.2 ml/10 g). Mortality was observed for three days.

The results are shown in Table I.

TABLE I

| Mortality at the 3rd day after subcutaneous injection:- | | |
|---|---|---|
| Compound No. (hydrochloride) | Dose (mg/kg) | Mortality rate[*1] |
| Amantadine | 300 | 6/6 |
| 29-1 (not hydrochloride) | 1000 | 0/6 |
| 12-4 | 2000 | 0/6 (±) |
| 12-3 | 705 | 0/6 (±) |
| 27-2 | 1190 | 0/6 (±) |

TABLE I-continued

| Mortality at the 3rd day after subcutaneous injection:- | | |
|---|---|---|
| Compound No. (hydrochloride) | Dose (mg/kg) | Mortality rate[*1] |
| 18-3 | 1000 | 0/6 (±) |
| 18-2 | 500 | 0/6 (±) |
| 44-1 | 1000 | 0/6 (±) |
| 27-4 | 250 | 1/6 |
| 27-4 | 500 | 6/6 |
| 49-1 | 250 | 0/6 (+) |
| 53-1 | 500 | 3/6 |
| 25-3 | 1000 | 0/6 |
| 44-4 | 1000 | 0/6 |

Note:
[*1] Number of deaths/Number of animals used.
(±): appearance of hyperactivity
(+): appearance of clonic convulsion

EXAMPLE 76

Effects on the catalepsy induced by haloperidol:

Six male dd-strain mice, weighing 25±3 g, were used in each group. Test drugs were injected intraperitoneally or subcutaneously 3.5 hours after the injection of haloperidol (7 mg/kg, s.c.).

The catalepsy was measured at 0.5 hour after injection of test drugs according to the method of Wirth et al. with slight modification [cf. Wirth, R., Gösswald, R., Hörlein, V., Risse, K. H. and Kreiskott, H. Archs int. Pharmacodyn., Ther., 115, 1–31 (1958)].

The results are shown in Table II.

TABLE II

| Compound No. (hydrochloride) | Dose (mg/kg) | Route | Number of showing anti-catalepty activity/ Number of total animal |
|---|---|---|---|
| Amantadine | 50 | s.c. | 3/6, 2/6 |
| 12-4 | 500 | s.c. | 0/6 |
| 12-3 | 500 | s.c. | 2/6 |
| 27-2 | 500 | s.c. | 1/6 |
| 18-3 | 500 | s.c. | 1/6 |
| 18-2 | 250 | s.c. | 3/6 |
| 44-1 | 250 | s.c. | 1/6 |
| 49-1 | 125 | s.c. | 1/6 |
| 25-3 | 500 | s.c. | 0/6 |
| 44-4 | 500 | s.c. | 0/6 |

EXAMPLE 77

Effects on Influenza virus infection:

The antiviral activities were determined by the modified Horsfall's method [cf. Tani et al., Fukuoka Igaku Zasshi, 58, 9 (1967)].

(1) Drug preparation

The compounds to be tested were dissolved in sterile physiological saline or suspended in 5% arabia gumsaline solution for injection.

(2) Animals

ICR male mice weighing about 12 g were used in this study. Ten animals were used in each experiment.

(3) Virus

Influenza A/PR/8/34 (HO,N1) strain (4) Drug evaluation

Five LD$_{50}$ of influenza virus was used for infecting mice by the aerosol. Subcutaneous drug treatment using various dosages started at 3 hour pre., 2, 6, 18, 30, 42, 54, 66, 78, 90, 102, 114, 126, 138 and 150 hour post infection in order to determine the efficacy of the compounds. Lung lesion score (LLC) was determined 7 days after infection by sacrificing the animals.

When the mice died with 5 days after infection, LLS determination was also carried out.

To obtain a LLS for each mouse, the following six possible disease categories were defined:

|  | LLS |
|---|---|
| Survival without pulmonary cosolidation | 0 |
| Survival less than 25% of lung cosolidated | 1 |
| Survival 25-50% of lung cosolidated | 2 |
| Survival 50-75% of lung cosolidated | 3 |
| Survival 75-100% of lung cosolidated | 4 |
| Death and 75-100% of lung cosolidated | 5 |

The results are shown in TABLE III.

TABLE III

| Compound No. (hydrochloride) | Dosage (mg/kg) | LLS |
|---|---|---|
| Control | — | 4.7 |
| Amantadine | 50 | 4.3 |
| 29-1 (not hydrochloride) | 25 | 4.3 |
| 12-3 | 25 | 3.6 |

EXAMPLE 78

Virus (Influenza A/PR/8/34 (HO,Nl) strain) and cell culture (MDCK cells) were used in this study and were grown in Earle-based Eagle-MEM containing 2.5 mg/ml of $NaHCO_3$ and 10% fetal calf serum. Maintenance medium was Eagle's MEM containing 2.5 mg/ml $NaHCO_3$, 0.1% bovine serum albumin and 20 μg/ml Tnypsin.

Technique of Virus inoculation and administration of anti-Influenza Compound:

After washing MDCK Cell monolayers with PBS(-), maintenance medium containing $10^3$ TCID50 of virus the drug was added to each culture tube and these tubes were then incubated at 34° C. for 3 days.

Assay of HA-tifer:

After incubation, each cell culture was frozen and thawed, and was centrifuged at 3000 rpm for 15 minutes. Fifty mcl aliquots of the supernatant fraction of each culture were assayed by the microtiter technique.

Drug evaluation

Antiviral effects and cytotoxicities of the test compounds were tested against influenza virus by the tube dilution assay.

Antiviral activity was expressed by minimum effective concentration (MEC, μg/ml) as defined by the minimum dose of the test compound which reduced the HA-titer of influenza virus 4 times or more than that of control.

Cytotoxicity was determined by microscopic examination and retardation of cell growth rate of host cell, and represented by minimum cytotoxicic concentration (MCC, μg/ml).

The results are shown in Table IV.

TABLE IV

| Compound No. (hydrochloride) | MEC (μg/ml) | MCC (μg/ml) | Chemotherapeutic index (MCC/MEC) |
|---|---|---|---|
| Amantadine | 12.5 | 12.5 | 1 |
| 12-4 | 50 | 100 | 2 |
| 12-3 | 50 | 100 | 2 |
| 27-2 | 25 | 200 | 8 |
| 18-3 | 50 | >200 | >4 |
| 18-2 | 50 | >200 | >4 |
| 44-1 | 25 | 50 | 2 |
| 27-4 | 25 | 100 | 4 |
| 49-1 | 25 | 50 | 2 |
| 53-1 | 12.5 | 25 | 2 |
| 25-3 | 25 | 100 | 4 |
| 41-5 | 50 | 100 | 2 |
| 44-3 | 50 | 100 | 2 |
| 44-4 | 100 | 100 | 1 |
| 12-10 | 25 | 100 | 4 |
| 67-1 | 25 | 100 | 4 |
| 12-9 | 50 | 100 | 2 |

What is claimed is:

1. A compound of the formula:

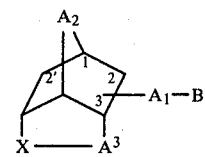

wherein $A_1$ is a single bond or a $C_1-C_5$ alkylene group bonding at the 2-, 2'- or 3-position, $A_2$ is a $C_1-C_3$ alkylene group, $A_3$ is a $C_1-C_4$ alkylene group, X is —O— or —$SO_n$—, wherein n is an integer of 0 to 2 and B is a cyano group; an amino group of the formula:

wherein $R_1$ is a hydrogen atom, a $C_1-C_5$ alkyl group, a $C_3-C_5$ alkenyl group, a $C_3-C_5$ alkynyl group or a $C_7-C_9$ aralkyl group and $R_2$ is a hydrogen atom, a $C_1-C_5$ alkyl group, a $C_3-C_5$ alkenyl group, a $C_3-C_5$ alkynyl group, a $C_7-C_9$ aralkyl group, a $C_2-C_5$ alkoxycarbonyl group, a benzyloxycarbonyl group, a $C_2-C_5$ alkanoyl group or a $C_2-C_4$ haloalkanoyl group; or a carbamoyl group of the formula:

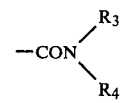

wherein $R_3$ and $R_4$ are each a hydrogen atom, a $C_1-C_5$ alkyl group or a $C_3-C_5$ alkenyl group, or non-toxic salts thereof.

2. A compound of the formula:

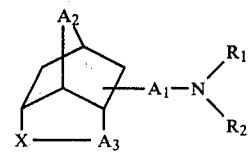

wherein $A_1$ is a single bond or a $C_1$–$C_5$ alkylene group bonding at the 2-, 2'- or 3-position, $A_2$ is a $C_1$–$C_3$ alkylene group, $A_3$ is a $C_1$–$C_4$ alkylene group, X is —O— or —SO$_n$—, wherein n is an integer of 0 to 2, $R_1$ is a hydrogen atom, a $C_1$–$C_5$ alkyl group, a $C_3$–$C_5$ alkenyl group, a $C_3$–$C_5$ alkynyl group or a $C_7$–$C_9$ aralkyl group and $R_2$ is a hydrogen atom, a $C_1$–$C_5$ alkyl group, a $C_3$–$C_5$ alkenyl group, a $C_3$–$C_5$ alkynyl group, a $C_7$–$C_9$ aralkyl group, a $C_2$–$C_5$ alkoxycarbonyl group, a benzyloxycarbonyl group, a $C_2$–$C_5$ alkanoyl group or a $C_2$–$C_4$ haloalkanoyl group or non-toxic salts thereof.

3. A compound of the formula:

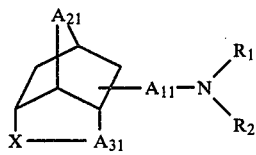

wherein $A_{11}$ is a single bond or a methylene group bonding at the 2-, 2'- or 3-position, $A_{21}$ is a methylene group or an ethylene group, $A_{31}$ is a methylene group or an ethylene group, X is —O— or —SO$_n$—, wherein n is an integer of 0 to 2, $R_1$ is a hydrogen atom, a $C_1$–$C_5$ alkyl group, a $C_3$–$C_5$ alkenyl group, a $C_3$–$C_5$ alkynyl group or a $C_7$–$C_9$ aralkyl group and $R_2$ is a hydrogen atom, a $C_1$–$C_5$ alkyl group, a $C_3$–$C_5$ alkenyl group, a $C_3$–$C_5$ alkynyl group, a $C_7$–$C_9$ aralkyl group, a $C_2$–$C_5$ alkoxycarbonyl group, a benzyloxycarbonyl group, a $C_2$–$C_5$ alkanoyl group or a $C_2$–$C_4$ haloalkanoyl group or non-toxic salts thereof.

4. A compound of the formula:

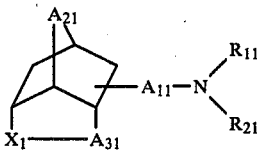

wherein $A_{11}$ is a single bond or a methylene group bonding at the 2-, 2'- or 3-position, $A_{21}$ is a methylene group or an ethylene group, $A_{31}$ is a methylene group or an ethylene group, $R_{11}$ is a hydrogen atom, a $C_1$–$C_5$ alkyl group, a $C_3$–$C_5$ alkenyl group, a $C_3$–$C_5$ alkynyl group or a $C_7$–$C_9$ aralkyl group, $R_{21}$ is a hydrogen atom, a $C_1$–$C_5$ alkyl group or a $C_2$–$C_5$ alkoxycarbonyl group and $X_1$ is —O— or —S—, or non-toxic salt thereof.

5. A compound of the formula:

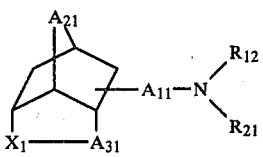

wherein $A_{11}$ is a single bond or a methylene group bonding at the 2-, 2'- or 3-position, $A_{21}$ is a methylene group or an ethylene group, $A_{31}$ is a methylene group or an ethylene group, $R_{12}$ is a hydrogen atom or a $C_1$–$C_5$ alkyl group, $R_{21}$ is a hydrogen atom, a $C_1$–$C_5$ alkyl group or a $C_2$–$C_5$ alkoxycarbonyl group and $X_1$ is —O— or —S—, or non-toxic salt thereof.

6. A compound of the formula:

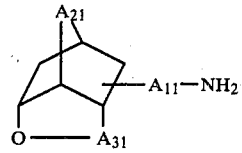

wherein $A_{11}$ is a single bond or methylene group bonding at the 2-, 2'- or 3-position, $A_{21}$ is a methylene group or an ethylene group and $A_{31}$ is a methylene group or an ethylene group, or non-toxic salt thereof.

7. An antiviral composition which comprises as an active ingredient an effective antiviral amount of at least one of the compounds of claim 2, 3, 4, 5 or 6, and at least one pharmaceutically acceptable inert carrier or diluent.

8. A method for inhibiting the growth of virus in mammals which comprises administering orally or parenterally to said mammals an effective antiviral amount of at least one of the compounds of claim 2, 3, 4, 5 or 6 and a pharmaceutically acceptable carrier or diluent.

9. The method of claim 8, wherein said virus is an RNA type virus.

10. The method of claim 8, wherein said virus is a virus of the Myxo group.

11. The method of claim 8, wherein said virus is an influenza virus.

12. The method of claim 8, wherein said compound is administered to said mammal in an amount of 0.5 to 50 mg per kilogram of the body weight of said mammal.

13. A method for inhibiting the growth of virus in mammals which comprises administering orally or parenterally to said mammals an effective antiviral amount of at least one compound of the formula:

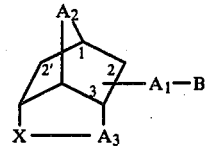

wherein $A_1$ is a single bond or a $C_1$–$C_5$ alkylene group bonding at the 2-, 2'- or 3-position, $A_2$ is a $C_1$–$C_3$ alkylene group, $A_3$ is a $C_1$–$C_4$ alkylene group, X is —O— or —SO$_n$—, wherein n is an integer of 0 to 2 and B is a carboxy group; a $C_2$–$C_5$ alkoxycarbonyl group; a cyano group; an amino group of the formula:

wherein $R_1$ is a hydrogen atom, a $C_1$–$C_5$ alkyl group, a $C_3$–$C_5$ alkenyl group, a $C_3$–$C_5$ alkynyl group or a $C_7$–$C_9$ aralkyl group and $R_2$ is a hydrogen atom, a $C_1$–$C_5$ alkyl group, a $C_3$–$C_5$ alkenyl group, a $C_3$–$C_5$ alkynyl group, a $C_7$–$C_9$ aralkyl group, a $C_2$–$C_5$ alkoxycarbonyl group, a benzyloxycarbonyl group, a $C_2$–$C_5$ alkanoyl group or a $C_2$–$C_4$ haloalkanoyl group; or a carbamoyl group of the formula:

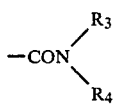

wherein $R_3$ and $R_4$ are each a hydrogen atom, a $C_1$–$C_5$ alkyl group or a $C_3$–$C_5$ alkenyl group, or non-toxic salts thereof; and a pharmaceutically acceptable carrier or diluent.

14. A method for inhibiting the growth of virus in mammals which comprises administering orally or parenterally to said mammals an effective antiviral amount of at least one compound of the formula:

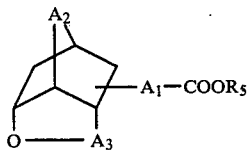

wherein $A_1$ is a single bond or a $C_1$–$C_5$ alkylene group bonding at the 2-, 2'- or 3-position, $A_2$ is a $C_1$–$C_3$ alkylene group, $A_3$ is a $C_1$–$C_4$ alkylene group and $R_5$ is a hydrogen atom or a $C_1$–$C_4$ alkyl group, or non-toxic salts thereof; and a pharmaceutically acceptable carrier or diluent.

15. A method for inhibiting the growth of virus in mammals which comprises administering orally or parenterally to said mammals an effective antiviral amount of at least one compound of the formula:

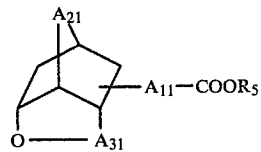

wherein $A_{11}$ is a single bond or a methylene group bonding at the 2-, 2'- or 3-position, $A_{21}$ is a methylene group or an ethylene group, $A_{31}$ is a methylene group or an ethylene group and $R_5$ is a hydrogen atom or a $C_1$–$C_4$ alkyl group, or non-toxic salts thereof; and a pharmaceutically acceptable carrier or diluent.

16. A method for inhibiting the growth of virus in mammals which comprises administering orally or parenterally to said mammals an effective antiviral amount of at least one compound of the formula:

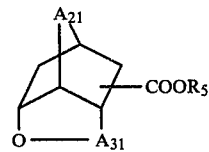

wherein the substituent (—COOR$_5$) is bonded at the 2-, 2'- or 3-position, $A_{21}$ is a methylene group or an ethylene group, $A_{31}$ is a methylene group or an ethylene group and $R_5$ is a hydrogen atom or a $C_1$–$C_4$ alkyl group, or non-toxic salts thereof; and a pharmaceutically acceptable carrier or diluent.

17. The method of claim 13, 14, 15 or 16, wherein said virus is an RNA type virus.

18. The method of claim 13, 14, 15 or 16, wherein said virus is a virus of the Myxo group.

19. The method of claim 13, 14, 15 or 16, wherein said virus is an influenza virus.

20. The method of claim 13, 14, 15 or 16, wherein said compound is administered to said mammal in an amount of 0.5 to 50 mg per kilogram of the body weight of said mammal.

* * * * *